United States Patent
Tang et al.

(10) Patent No.: US 11,737,435 B2
(45) Date of Patent: Aug. 29, 2023

(54) NON-HUMAN ANIMALS COMPRISING A HUMANIZED COAGULATION FACTOR 12 LOCUS

(71) Applicant: Regeneron Pharmaceuticals, Inc., Tarrytown, NY (US)

(72) Inventors: Yajun Tang, White Plains, NY (US); Dan Chalothorn, New York, NY (US); Lyndon Mitnaul, Piscataway, NJ (US); Lori Morton, Chappaqua, NY (US); Daria Zamolodchikov, Hastings-on-Hudson, NY (US); Nicole Alessandri-Haber, Rye Brook, NY (US); Lynn Macdonald, Harrison, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 603 days.

(21) Appl. No.: 16/838,519

(22) Filed: Apr. 2, 2020

(65) Prior Publication Data
US 2020/0315149 A1   Oct. 8, 2020

Related U.S. Application Data

(60) Provisional application No. 62/829,321, filed on Apr. 4, 2019.

(51) Int. Cl.
| | |
|---|---|
| *A01K 67/027* | (2006.01) |
| *C07K 14/745* | (2006.01) |
| *C12Q 1/6876* | (2018.01) |
| *C12N 9/22* | (2006.01) |
| *C12N 15/86* | (2006.01) |

(52) U.S. Cl.
CPC ........ *A01K 67/0278* (2013.01); *C07K 14/745* (2013.01); *C12N 9/22* (2013.01); *C12N 15/86* (2013.01); *C12Q 1/6876* (2013.01); *A01K 2207/15* (2013.01); *A01K 2217/072* (2013.01); *A01K 2217/203* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 5,942,435 | A  | 8/1999  | Wheeler |
| 6,586,251 | B2 | 7/2003  | Economides et al. |
| 7,294,754 | B2 | 11/2007 | Poueymirou et al. |
| 7,576,259 | B2 | 8/2009  | Poueymirou et al. |
| 7,659,442 | B2 | 2/2010  | Poueymirou et al. |
| 10,329,582 | B2 | 6/2019  | Lee et al. |
| 10,385,359 | B2 | 8/2019  | Lee et al. |
| 2008/0078000 | A1 | 3/2008 | Poueymirou et al. |
| 2009/0064350 | A1 | 3/2009 | Dewald |
| 2009/0235369 | A1 | 9/2009 | Sasgary et al. |
| 2011/0154517 | A1 | 6/2011 | Dewald |
| 2011/0200982 | A1 | 8/2011 | Stevens et al. |
| 2012/0082987 | A1* | 4/2012 | Sasgary ............ A01K 67/0275 435/6.12 |
| 2013/0042330 | A1 | 2/2013 | Murphy et al. |
| 2013/0111617 | A1 | 5/2013 | Macdonald et al. |
| 2013/0117873 | A1 | 5/2013 | Wang et al. |
| 2013/0340104 | A1 | 12/2013 | Murphy |
| 2014/0134662 | A1 | 5/2014 | Flavell et al. |
| 2014/0178879 | A1 | 6/2014 | Economides et al. |
| 2014/0235933 | A1 | 8/2014 | Lee et al. |
| 2014/0245467 | A1 | 8/2014 | Macdonald et al. |
| 2014/0310828 | A1 | 10/2014 | Lee et al. |
| 2015/0106961 | A1 | 4/2015 | Rojas et al. |
| 2015/0106962 | A1 | 4/2015 | Sachs et al. |

(Continued)

FOREIGN PATENT DOCUMENTS

| | | |
|---|---|---|
| EP | 0989184 A1 | 3/2000 |
| WO | WO 2001/079228 A2 | 10/2001 |

(Continued)

OTHER PUBLICATIONS

Bork et al., "Characterization of a partial exon 9/intron 9 deletion in the coagulation factor XII gene (F12) detected in two Turkish families with hereditary angioedema and normal C1 inhibitor," Haemophilia, 20(5):e372-e375, (2014).
Devoy et al., "Genomically humanized mice: technologies and promise," Nat. Rev. Genet., 13(1):14-20, (2011).
Renné et al., "Defective thrombus formation in mice lacking coagulation factor XII," J. Exp. Med., 202(2):271-281, (2005).
Zamolodchikov et al., "Activation of the factor XII-driven contact system in Alzheimer's disease patient and mouse model plasma," Proc. Natl. Acad. Sci. U.S.A., 112(13):4068-4073, (2015).
WIPO Application No. PCT/US2020/026413, PCT International Search Report and Written Opinion of the International Searching Authority dated Jun. 17, 2020.

(Continued)

*Primary Examiner* — Allison M Fox
*Assistant Examiner* — Alyssa G Weston
(74) *Attorney, Agent, or Firm* — Yongjin Choi; Alston & Bird LLP

(57) ABSTRACT

Non-human animal genomes, non-human animal cells, and non-human animals comprising a humanized coagulation factor XII (F12) locus and methods of making and using such non-human animal genomes, non-human animal cells, and non-human animals are provided. Non-human animal cells or non-human animals comprising a humanized F12 locus express a human coagulation factor XII protein or a chimeric coagulation factor XII protein, fragments of which are from human coagulation factor XII. Methods are provided for using such non-human animals comprising a humanized F12 locus to assess in vivo efficacy of human-coagulation-factor-XII-targeting reagents such as nuclease agents designed to target human F12. A short isoform of F12 that is produced locally in the brain, and methods of using the short isoform, are also provide.

17 Claims, 16 Drawing Sheets

Specification includes a Sequence Listing.

(56) References Cited

U.S. PATENT DOCUMENTS

| | | |
|---|---|---|
| 2015/0313194 A1 | 11/2015 | Hu et al. |
| 2015/0320021 A1 | 11/2015 | Wang et al. |
| 2015/0327524 A1 | 11/2015 | Murphy et al. |
| 2015/0342163 A1 | 12/2015 | Voronina et al. |
| 2015/0376628 A1 | 12/2015 | Schoenherr et al. |
| 2015/0376651 A1 | 12/2015 | Frendewey et al. |
| 2016/0060358 A1 | 3/2016 | Hay |
| 2016/0145646 A1 | 5/2016 | Frendewey et al. |
| 2017/0245481 A1 | 8/2017 | Gusarova et al. |
| 2018/0139940 A1 | 5/2018 | Macdonald et al. |
| 2018/0243450 A1 | 8/2018 | Devalaraja-Narashimha et al. |
| 2019/0098879 A1 | 4/2019 | Drummond-Samuelson et al. |
| 2019/0290783 A1 | 9/2019 | Voronina et al. |
| 2020/0015462 A1 | 1/2020 | Murphy et al. |
| 2020/0383304 A1 | 12/2020 | Fang et al. |
| 2020/0385760 A1 | 12/2020 | Haines et al. |
| 2020/0392541 A1 | 12/2020 | Zhang et al. |

FOREIGN PATENT DOCUMENTS

| | | |
|---|---|---|
| WO | WO 2009/053050 A1 | 4/2009 |
| WO | WO 2014/130706 A1 | 8/2014 |
| WO | WO 2014/172489 A2 | 10/2014 |
| WO | WO 2015/042557 A1 | 3/2015 |
| WO | WO 2015/088643 A1 | 6/2015 |
| WO | WO 2015/200334 A1 | 12/2015 |
| WO | WO 2015/200805 A2 | 12/2015 |
| WO | WO 2016/044745 A1 | 3/2016 |
| WO | WO 2016/081923 A2 | 5/2016 |
| WO | WO 2017/087780 A1 | 5/2017 |
| WO | WO 2020/206139 A1 | 10/2020 |

OTHER PUBLICATIONS

Ashby et al., "Assessment of activation of the plasma kallikrein-kinin system in frontal and temporal cortex in Alzheimer's disease and vascular dementia," Neurobiology of Aging, 33(7):1345-1355, (2012).
Atanasio et al., "C9orf72 ablation causes immune dysregulation characterized by leukocyte expansion, autoantibody production, and glomerulonephropathy in mice," Scientific Reports, 6:23204, (2016).
Barthold, "Genetically altered mice: phenotypes, no phenotypes, and Faux phenotypes," Genetica, 122(1):75-88, (2004).
Benson et al., "GenBank," Nucleic Acids Research, 41(Database Issue):D36-D42, (2012).
Bergamaschini et al., "Activation of complement and contact system in Alzheimer's disease," Mechanisms of Ageing and Development, 122(16):1971-1983, (2001).
Birling, et al., "Modeling human disease in rodents by CRISPR/Cas9 genome editing," Mamm. Genome, 28(7-8):291-301, (2017).
Brevini, et al., "No shortcuts to pig embryonic stem cells," Theriogenology, 74(4):544-550, (2010).
Brevini, et al., "Porcine embryonic stem cells: Facts, challenges and hopes," Theriogenology, 68 Suppl. 1:S206-S213, (2007).
Burova, et al., "Characterization of the Anti-PD-1 Antibody REGN2810 and Its Antitumor Activity in Human PD-1 Knock-in Mice," Mol. Cancer Ther., 16(5):861-870, (2017).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Cerf et al., "Immunolocalization of Plasma Kaliikrein in Human Brain," Metabolic Brain Disease, 15(4):315-323, (2000).
Clark, et al., "A future for transgenic livestock," Nat. Rev. Genet., 4(10):825-833, (2003).
De Maat et al., "Factor XII truncation accelerates activation in solution," Journal of Thrombosis and Haemostasis,17(1):183-194, (2019).
Deaton et al., "CpG islands and the regulation of transcription," Genes and Development, 25:1010-1022, (2011).
Dechiara, T.M., et al., "VelociMouse: Fully ES Cell-Derived F0-Generation Mice Obtained from the Injection of ES Cells into Eight-Cell-Stage Embryos," Methods in Molecular Biology, 530(16): 311-324, (2009).

Dennis, "Welfare Issues of Genetically Modified Animals," ILAR J., 43(2):100-109, (2002).
Frendewey, et al., "The Loss-of-Allele Assay for ES Cell Screening and Mouse Genotyping," Methods Enzymol., 476:295-307, (2010).
Genoway, "Humanized Mouse Model," retrieved from https://www.genoway.com/services/customized-mouse/knockin-models/humanisation.htm on May 12, 2018.
Ghebrehiwet et al., "Activation of the Classical Pathway of Complement by Hageman Factor Fragment," J. Exp. Med., 153(3):665-676, (1981).
Göbel et al., "Blood coagulation factor XII drives adaptive immunity during neuroinflammation via CD87-mediated modulation of dendritic cells," Nature Communications, 7:11626, pp. 1-16, (2016).
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
GTEX Consortium, "The Genotype-Tissue Expression (GTEx) project," Nature Genetics, 45(6):580-585, (2013).
Hammond et al., "Microglia and the Brain: Complementary Partners in Development and Disease," Annu. Rev. Cell Dev. Biol., 34:523-544, (2018).
Harari et al., "Bridging the species divide: transgenic mice humanized for type-I interferon response," PLoS One 9(1):e84259, (2014).
Herndler-Brandstetter, et al., "Humanized mouse model supports development, function, and tissue residency of human natural killer cells," Proc. Natl. Acad. Sci. U.S.A., 114(45):E9626-E9634, (2017).
Houdebine, "Methods to Generate Transgenic Animals," pp. 31-48 in "Genetic Engineering in Livestock: New Applications and Interdisciplinary Perspectives," Ed. Engelhard et al., (2009).
Jablonska et al., "Transforming Growth Factor-β1 Induces Expression of Human Coagulation Factor XII via Smad3 and JNK Signaling Pathways in Human Lung Fibroblasts," The Journal of Biological Chemistry, 285(15):11638-11651, (2010).
Jean, et al., "Pluripotent genes in avian stem cells," Dev. Growth Differ., 55(1): 41-51, (2013).
Kato et al., "Biological roles of hepatocyte growth factor-Met signaling from genetically modified animals (Review)," Biomedical Reports, 7(6):495-503, (2017).
Kawamata, et al., "Generation of genetically modified rats from embryonic stem cells," Proc. Natl. Acad. Sci. U.S.A., 7(32):14223-14228, (2010).
Kent et al., "The Human Genome Browser at UCSC," Genome Research, 12(6):996-1006, (2002).
Kumar, et al., "Transgenic Mouse Technology: Principles and Methods," Methods Mol. Biol., 590:335-362, (2009).
Lute, et al., "Human CTLA4 knock-in mice unravel the quantitative link between tumor immunity and autoimmunity induced by anti-CTLA-4 antibodies," Blood, 106(9):3127-3133, (2005).
Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).
Neth et al., "The mRNAs of Prekallikrein, Factors XI and XII, and Kininogen, Components of the Contact Phase Cascade Are Differentially Expressed in Multiple Non-hepatic Human Tissues," Thromb. Haemost., 85(6):1043-1047, (2001).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Paris, et al., "Equine embryos and embryonic stem cells: defining reliable markers of pluripotency," Theriogenology, 74(4): 516-524, (2010).
Peek et al., "Unusual Proteolytic Activation of Pro-hepatocyte Growth Factor by Plasma Kallikrein and Coagulation Factor XIa," The Journal of Biological Chemistry, 277(49):47804-47809, (2002).
Poueymirou et al., "F0 generation mice fully derived from gene-targeted embryonic stem cells allowing immediate phenotypic analyses," Nat. Biotechnol., 25(1):91-99, (2007).
Reyes-Haro et al., "Regional density of glial cells in the rat corpus callosum," Biol. Res., 46(1):27-32, (2013).

(56) References Cited

OTHER PUBLICATIONS

Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Shimomura et al., "Activation of hepatocyte growth factor by two homologous proteases, blood-coagulation factor XIIa and hepatocyte growth factor activator," Eur. J. Biochem., 229(1):257-261, (1995).
Sigmund, "Viewpoint: Are Studies in Genetically Altered Mice Out of Control?," Arterioscler. Thromb. Vasc. Biol., 20(6):1425-1429, (2000).
Song et al., "PROSPER: an Integrated Feature-Based Tool for Predicting Protease Substrate Cleavage Sites," PLoS ONE, 7(11):e50300, pp. 1-23, (2012).
Stavrou et al., "Factor XII and uPAR upregulate neutrophil functions to influence wound healing," The Journal of Clinical Investigation, 128(3):944-959, (2018).
Takano et al., "Lipopolysaccharide injection into the cerebral ventricle evokes kininogen induction in the rat brain," Brain Research, 978(1-2):72-82, (2003).
Valenzuela, et al., "High-throughput engineering of the mouse genome coupled with high-resolution expression analysis," Nat. Biotechnol., 21(6):652-659, (2003).
Wakchaure, et al., "Transgenic Animals: a Review on its Various Dimensions and Applications in Animal Biotechnology," International Journal of Emerging Technology and Advanced Engineering, 5(11):210-213, (2015).
Wright et al., "The Brain Hepatocyte Growth Factor/c-Met Receptor System: a New Target for the Treatment of Alzheimer's Disease," Journal of Alzheimer's Disease, 45(4):985-1000, (2015).
Yasuhara et al., "Hageman factor and its binding sites are present in senile plaques of Alzheimer's disease," Brain Research, 654(2):234-240, (1994).
Yin et al., "Brain Endothelial Cells Synthesize Neurotoxic Thrombin in Alzheimer's Disease," The American Journal of Pathology, 176(4):1600-1606, (2010).
Zamolodchikov et al., "A Short Isoform of Coagulation Factor XII mRNA Is Expressed by Neurons in the Human Brain," Neuroscience, 413:294-307, (2019).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Schloesser, et al., "Mutations in the Human Factor XII Gene," Blood, 90(10):3967-3977, (Nov. 1997).
Zhu et al., "Humanising the mouse genome piece by piece," Nat. Commun. 10(1):1845, (Apr. 23, 2019).

* cited by examiner

| | |
|---|---|
| hF12 | MRALLLLGFLIVSLESTLSIPPWEAPKEHKYKAEEHTVVLTVTGEPCHFPFQYHRQL |
| mF12 | MTALLFLGSLLMSLDLTLSAPPWKDSKKFKDAPDGPTVVLTVDGRLCHFPFQYHRQL |
| hF12 | YHKCTHKGRPGPQPWCATTPNFDQDQRWGYCLEPKKVKDHCSKHSPCQKGGTCVNMP |
| mF12 | HHKCIHKRRPGSRPWCATTPNFDEDQQWGYCLEPKKVKDHCSKHNPCHKGGTCINTP |
| hF12 | SGPHCLCPQHLTGNHCQKEKCFEPQLLRFFHKNEIWYRTEQAAVARCQCKGPDAHCQ |
| mF12 | NGPHCLCPEHLTGKHCQKEKCFEPQLLKFFHENELWFRTGPGGVARCECKGSEAHCK |
| hF12 | RLASQACRTNPCLHGGRCLEVEGHRLCHCPVGYTGPFCDVDTKASCYDGRGLSYRGL |
| mF12 | PVASQACSINPCLNGGSCLLVEDHPLCRCPTGYTGYFCDLDLWATCYEGRGLSYRGQ |
| hF12 | ARTTLSGAPCQPWASEATYRNVTAEQARNWGLGGHAFCRNPDNDIRPWCFVLNRDRL |
| mF12 | AGTTQSGAPCQRWTVEATYRNMTEKQALSWGLGHHAFCRNPDNDTRPWCFVWSGDRL |
| hF12 | SWEYCDLAQCQTPTQAAPPTPVSPRLHVPLMPAQPAPPKPQPTTRTPPQSQTPGALP |
| mF12 | SWDYCGLEQCQTPTFAPLVVPES      QEESPSQAPSLSHAPNDST |
| | ... Heavy Chain \| Light Chain ... |
| hF12 | AKREQPPSLTRNGPLSCGQRLRKSLSSMTRVVGGLVALRGAHPYIAALYWGHSFCAG |
| mF12 | DHQTSLSKTNTMGCGQRFRKGLSSFMRVVGGLVALPGSHPYIAALYWGNNFCAG |
| hF12 | SLIAPCWVLTAAHCLQDRPAPEDLTVVLGQERRNHSCEPCQTLAVRSYRLHEAFSPV |
| mF12 | SLIAPCWVLTAAHCLQNRPAPEELTVVLGQDRHNQSCEWCQTLAVRSYRLHEGFSSI |
| hF12 | SYQHDLALLRLQEDADGSCALLSPYVQPVCLPSGAARPSETTLCQVAGWGHQFEGAE |
| mF12 | TYQHDLALLRLQESKTNSCAILSPHVQPVCLPSGAAPPSETVLCEVAGWGHQFEGAE |
| hF12 | EYASFLQEAQVPFLSLERCSAPDVHGSSILPGMLCAGFLEGGTDACQGDSGGPLVCE |
| mF12 | EYSTFLQEAQVPFIALDRCSNSNVHGDAILPGMLCAGFLEGGTDACQGDSGGPLVCE |
| hF12 | DQAAERRLTLQGIISWGSGCGDRNKPGVYTDVAYYLAWIREHTVS (SEQ ID NO: 5) |
| mF12 | EGTAEHQLTLRGVISWGSGCGDRNKPGVYTDVANYLAWIQKHIAS (SEQ ID NO: 1) |

FIG. 3

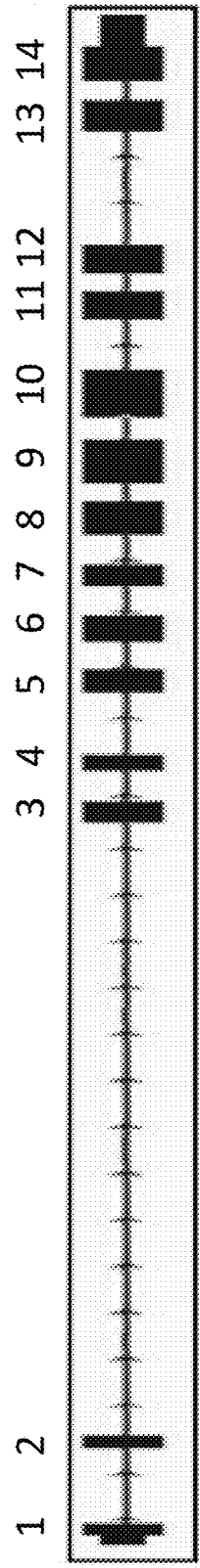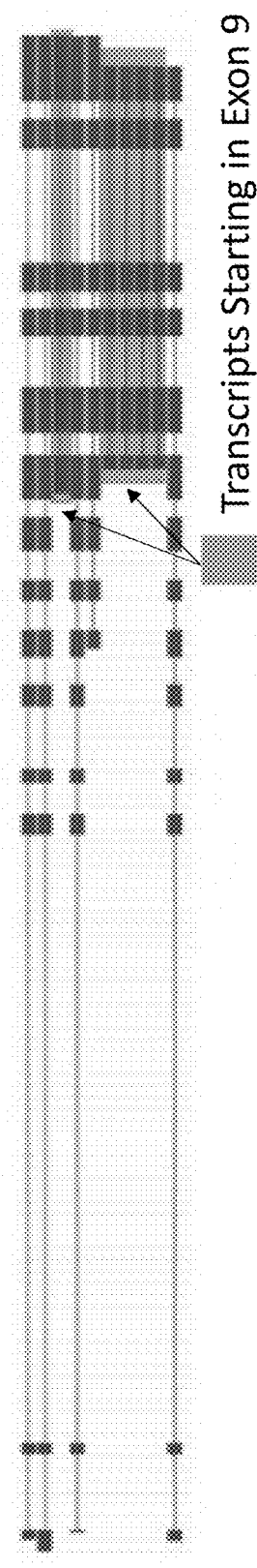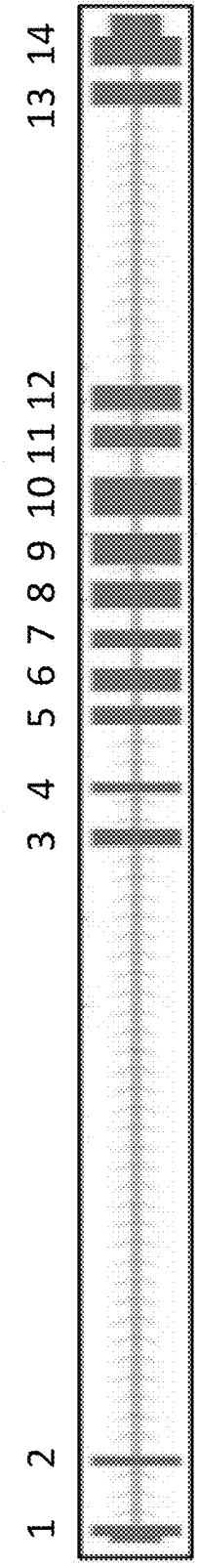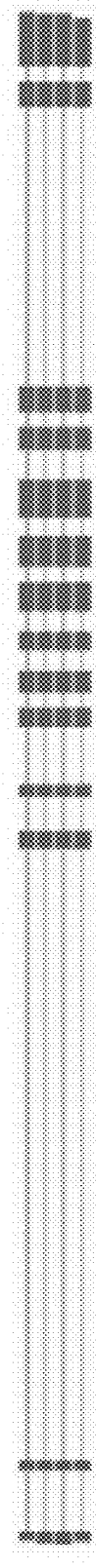
FIG. 8A

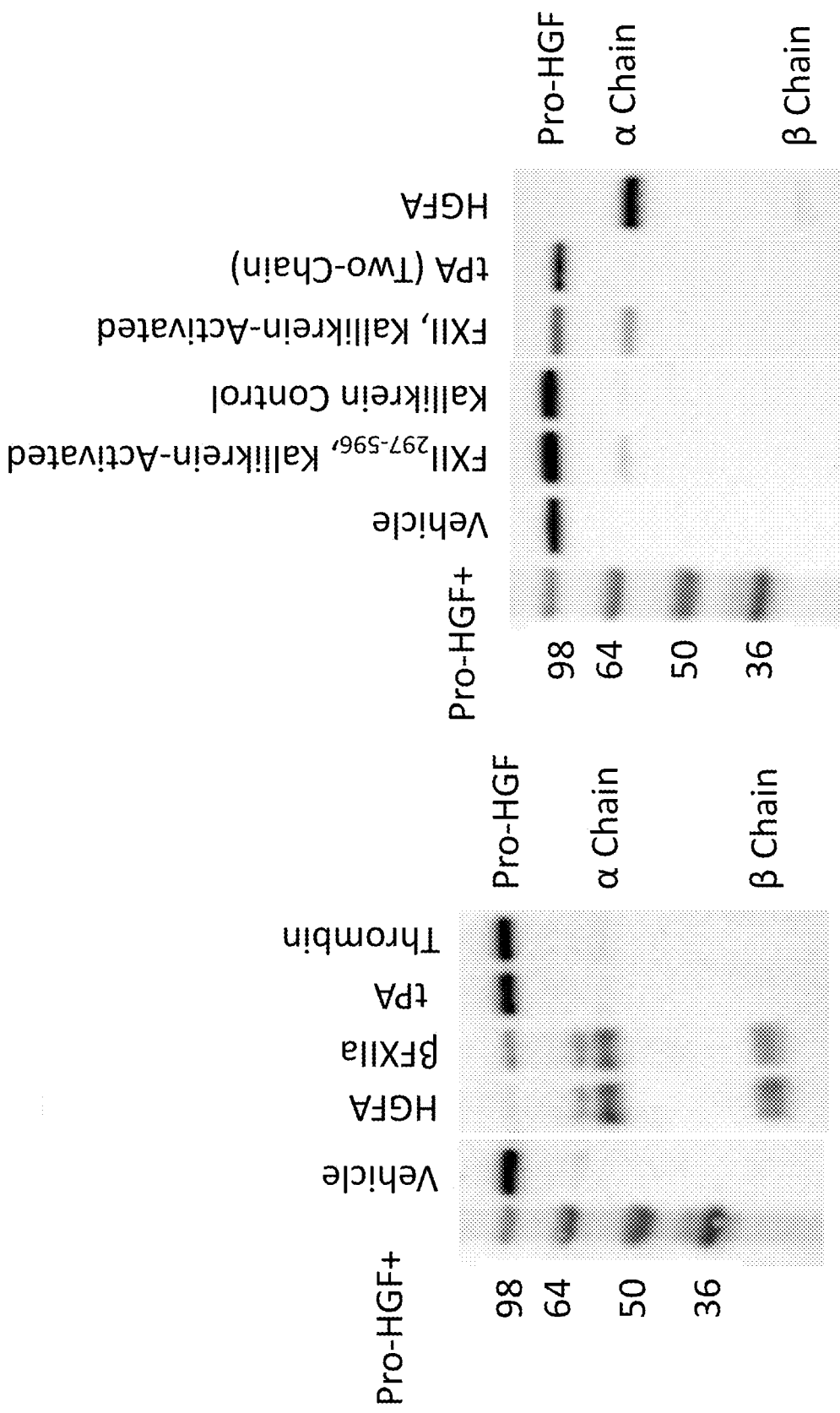

SEQUENCE LISTING

<160> NUMBER OF SEQ ID NOS: 84

<210> SEQ ID NO 1
<211> LENGTH: 597
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: Signal Peptide
<220> FEATURE:
<221> NAME/KEY: MISC_FEATURE
<222> LOCATION: (20)..(354)
<223> OTHER INFORMATION: Heavy Chain
<220> FEATURE:
<221> NAME/KEY: MISC_FEATURE
<222> LOCATION: (355)..(597)
<223> OTHER INFORMATION: Light Chain

<400> SEQUENCE: 1

Met Thr Ala Leu Leu Phe Leu Gly Ser Leu Met Ser Leu Asp Leu
1               5                   10                  15

Thr Leu Ser Ala Pro Pro Trp Lys Asp Ser Lys Lys Phe Lys Asp Ala
            20                  25                  30

Pro Asp Gly Pro Thr Val Val Leu Thr Val Asp Gly Arg Leu Cys His
        35                  40                  45

Phe Pro Phe Gln Tyr His Arg Gln Leu His His Lys Cys Ile His Lys
    50                  55                  60

Arg Arg Pro Gly Ser Arg Pro Trp Cys Ala Thr Thr Pro Asn Phe Asp
65                  70                  75                  80

Glu Asp Gln Gln Trp Gly Tyr Cys Leu Glu Pro Lys Lys Val Lys Asp
                85                  90                  95

His Cys Ser Lys His Asn Pro Cys His Lys Gly Gly Thr Cys Ile Asn
            100                 105                 110

Thr Pro Asn Gly Pro His Cys Leu Cys Pro Glu His Leu Thr Gly Lys
        115                 120                 125

His Cys Gln Lys Glu Lys Cys Phe Glu Pro Gln Leu Leu Lys Phe Phe
    130                 135                 140

His Glu Asn Glu Leu Trp Phe Arg Thr Gly Pro Gly Gly Val Ala Arg
145                 150                 155                 160

Cys Glu Cys Lys Gly Ser Glu Ala His Cys Lys Pro Val Ala Ser Gln
                165                 170                 175

Ala Cys Ser Ile Asn Pro Cys Leu Asn Gly Gly Ser Cys Leu Leu Val
            180                 185                 190

Glu Asp His Pro Leu Cys Arg Cys Pro Thr Gly Tyr Thr Gly Tyr Phe
        195                 200                 205

Cys Asp Leu Asp Leu Trp Ala Thr Cys Tyr Glu Gly Arg Gly Leu Ser
    210                 215                 220

Tyr Arg Gly Gln Ala Gly Thr Thr Gln Ser Gly Ala Pro Cys Gln Arg
225                 230                 235                 240

Trp Thr Val Glu Ala Thr Tyr Arg Asn Met Thr Glu Lys Gln Ala Leu
                245                 250                 255

Ser Trp Gly Leu Gly His His Ala Phe Cys Arg Asn Pro Asp Asn Asp
            260                 265                 270

Thr Arg Pro Trp Cys Phe Val Trp Ser Gly Asp Arg Leu Ser Trp Asp
        275                 280                 285

Tyr Cys Gly Leu Glu Gln Cys Gln Thr Pro Thr Phe Ala Pro Leu Val
    290                 295                 300

Val Pro Glu Ser Gln Glu Ser Pro Ser Gln Ala Pro Ser Leu Ser
305                 310                 315                 320

His Ala Pro Asn Asp Ser Thr Asp His Gln Thr Ser Leu Ser Lys Thr
            325                 330                 335

Asn Thr Met Gly Cys Gly Gln Arg Phe Arg Lys Gly Leu Ser Ser Phe
                340                 345                 350

Met Arg Val Val Gly Gly Leu Val Ala Leu Pro Gly Ser His Pro Tyr
            355                 360                 365

Ile Ala Ala Leu Tyr Trp Gly Asn Asn Phe Cys Ala Gly Ser Leu Ile
        370                 375                 380

Ala Pro Cys Trp Val Leu Thr Ala Ala His Cys Leu Gln Asn Arg Pro
385                 390                 395                 400

Ala Pro Glu Glu Leu Thr Val Val Leu Gly Gln Asp Arg His Asn Gln
                405                 410                 415

Ser Cys Glu Trp Cys Gln Thr Leu Ala Val Arg Ser Tyr Arg Leu His
                420                 425                 430

Glu Gly Phe Ser Ser Ile Thr Tyr Gln His Asp Leu Ala Leu Leu Arg
            435                 440                 445

Leu Gln Glu Ser Lys Thr Asn Ser Cys Ala Ile Leu Ser Pro His Val
450                 455                 460

Gln Pro Val Cys Leu Pro Ser Gly Ala Ala Pro Ser Glu Thr Val
465                 470                 475                 480

Leu Cys Glu Val Ala Gly Trp Gly His Gln Phe Glu Gly Ala Glu Glu
                485                 490                 495

Tyr Ser Thr Phe Leu Gln Glu Ala Gln Val Pro Phe Ile Ala Leu Asp
            500                 505                 510

Arg Cys Ser Asn Ser Asn Val His Gly Asp Ala Ile Leu Pro Gly Met
        515                 520                 525

Leu Cys Ala Gly Phe Leu Glu Gly Gly Thr Asp Ala Cys Gln Gly Asp
530                 535                 540

Ser Gly Gly Pro Leu Val Cys Glu Glu Gly Thr Ala Glu His Gln Leu
545                 550                 555                 560

Thr Leu Arg Gly Val Ile Ser Trp Gly Ser Gly Cys Gly Asp Arg Asn
                565                 570                 575

Lys Pro Gly Val Tyr Thr Asp Val Ala Asn Tyr Leu Ala Trp Ile Gln
            580                 585                 590

Lys His Ile Ala Ser
            595

<210> SEQ ID NO 2
<211> LENGTH: 19
<212> TYPE: PRT
<213> ORGANISM: Mus musculus

<400> SEQUENCE: 2

Met Thr Ala Leu Leu Phe Leu Gly Ser Leu Leu Met Ser Leu Asp Leu
1               5                   10                  15

Thr Leu Ser

<210> SEQ ID NO 3
<211> LENGTH: 335
<212> TYPE: PRT
<213> ORGANISM: Mus musculus

<400> SEQUENCE: 3

Ala Pro Pro Trp Lys Asp Ser Lys Lys Phe Lys Asp Ala Pro Asp Gly

-continued

```
                1               5                   10                  15
        Pro Thr Val Val Leu Thr Val Asp Gly Arg Leu Cys His Phe Pro Phe
                        20                  25                  30

Gln Tyr His Arg Gln Leu His His Lys Cys Ile His Lys Arg Arg Pro
                        35                  40                  45

Gly Ser Arg Pro Trp Cys Ala Thr Thr Pro Asn Phe Asp Glu Asp Gln
                        50                  55                  60

Gln Trp Gly Tyr Cys Leu Glu Pro Lys Val Lys Asp His Cys Ser
         65                  70                  75                  80

Lys His Asn Pro Cys His Lys Gly Gly Thr Cys Ile Asn Thr Pro Asn
                        85                  90                  95

Gly Pro His Cys Leu Cys Pro Glu His Leu Thr Gly Lys His Cys Gln
                        100                 105                 110

Lys Glu Lys Cys Phe Glu Pro Gln Leu Leu Lys Phe His Glu Asn
                        115                 120                 125

Glu Leu Trp Phe Arg Thr Gly Pro Gly Val Ala Arg Cys Glu Cys
         130                 135                 140

Lys Gly Ser Glu Ala His Cys Lys Pro Val Ala Ser Gln Ala Cys Ser
         145                 150                 155                 160

Ile Asn Pro Cys Leu Asn Gly Gly Ser Cys Leu Val Glu Asp His
                        165                 170                 175

Pro Leu Cys Arg Cys Pro Thr Gly Tyr Thr Gly Tyr Phe Cys Asp Leu
                        180                 185                 190

Asp Leu Trp Ala Thr Cys Tyr Glu Gly Arg Gly Leu Ser Tyr Arg Gly
                        195                 200                 205

Gln Ala Gly Thr Thr Gln Ser Gly Ala Pro Cys Gln Arg Trp Thr Val
                        210                 215                 220

Glu Ala Thr Tyr Arg Asn Met Thr Glu Lys Gln Ala Leu Ser Trp Gly
         225                 230                 235                 240

Leu Gly His His Ala Phe Cys Arg Asn Pro Asp Asn Asp Thr Arg Pro
                        245                 250                 255

Trp Cys Phe Val Trp Ser Gly Asp Arg Leu Ser Trp Asp Tyr Cys Gly
                        260                 265                 270

Leu Glu Gln Cys Gln Thr Pro Thr Phe Ala Pro Leu Val Val Pro Glu
                        275                 280                 285

Ser Gln Glu Glu Ser Pro Ser Gln Ala Pro Ser Leu Ser His Ala Pro
                        290                 295                 300

Asn Asp Ser Thr Asp His Gln Thr Ser Leu Ser Lys Thr Asn Thr Met
         305                 310                 315                 320

Gly Cys Gly Gln Arg Phe Arg Lys Gly Leu Ser Ser Phe Met Arg
                        325                 330                 335

<210> SEQ ID NO 4
<211> LENGTH: 243
<212> TYPE: PRT
<213> ORGANISM: Mus musculus

<400> SEQUENCE: 4

Val Val Gly Gly Leu Val Ala Leu Pro Gly Ser His Pro Tyr Ile Ala
         1                   5                   10                  15

Ala Leu Tyr Trp Gly Asn Asn Phe Cys Ala Gly Ser Leu Ile Ala Pro
                        20                  25                  30

Cys Trp Val Leu Thr Ala Ala His Cys Leu Gln Asn Arg Pro Ala Pro
                        35                  40                  45
```

```
Glu Glu Leu Thr Val Val Leu Gly Gln Asp Arg His Asn Gln Ser Cys
 50                  55                  60

Glu Trp Cys Gln Thr Leu Ala Val Arg Ser Tyr Arg Leu His Glu Gly
 65                  70                  75                  80

Phe Ser Ser Ile Thr Tyr Gln His Asp Leu Ala Leu Leu Arg Leu Gln
                 85                  90                  95

Glu Ser Lys Thr Asn Ser Cys Ala Ile Leu Ser Pro His Val Gln Pro
            100                 105                 110

Val Cys Leu Pro Ser Gly Ala Ala Pro Ser Glu Thr Val Leu Cys
            115                 120                 125

Glu Val Ala Gly Trp Gly His Gln Phe Glu Gly Ala Glu Glu Tyr Ser
 130                 135                 140

Thr Phe Leu Gln Glu Ala Gln Val Pro Phe Ile Ala Leu Asp Arg Cys
 145                 150                 155                 160

Ser Asn Ser Asn Val His Gly Asp Ala Ile Leu Pro Gly Met Leu Cys
                 165                 170                 175

Ala Gly Phe Leu Glu Gly Gly Thr Asp Ala Cys Gln Gly Asp Ser Gly
                 180                 185                 190

Gly Pro Leu Val Cys Glu Glu Gly Thr Ala Glu His Gln Leu Thr Leu
            195                 200                 205

Arg Gly Val Ile Ser Trp Gly Ser Gly Cys Gly Asp Arg Asn Lys Pro
            210                 215                 220

Gly Val Tyr Thr Asp Val Ala Asn Tyr Leu Ala Trp Ile Gln Lys His
225                 230                 235                 240

Ile Ala Ser

<210> SEQ ID NO 5
<211> LENGTH: 615
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Signal Peptide
<220> FEATURE:
<221> NAME/KEY: MISC_FEATURE
<222> LOCATION: (20)..(372)
<223> OTHER INFORMATION: Heavy Chain
<220> FEATURE:
<221> NAME/KEY: MISC_FEATURE
<222> LOCATION: (373)..(615)
<223> OTHER INFORMATION: Light Chain

<400> SEQUENCE: 5

Met Arg Ala Leu Leu Leu Leu Gly Phe Leu Leu Val Ser Leu Glu Ser
 1               5                  10                  15

Thr Leu Ser Ile Pro Pro Trp Glu Ala Pro Lys Glu His Lys Tyr Lys
                 20                  25                  30

Ala Glu Glu His Thr Val Val Leu Thr Val Thr Gly Glu Pro Cys His
             35                  40                  45

Phe Pro Phe Gln Tyr His Arg Gln Leu Tyr His Lys Cys Thr His Lys
 50                  55                  60

Gly Arg Pro Gly Pro Gln Pro Trp Cys Ala Thr Thr Pro Asn Phe Asp
 65                  70                  75                  80

Gln Asp Gln Arg Trp Gly Tyr Cys Leu Glu Pro Lys Lys Val Lys Asp
                 85                  90                  95

His Cys Ser Lys His Ser Pro Cys Gln Lys Gly Gly Thr Cys Val Asn
            100                 105                 110
```

```
Met Pro Ser Gly Pro His Cys Leu Cys Pro Gln His Leu Thr Gly Asn
            115                 120                 125
His Cys Gln Lys Glu Lys Cys Phe Glu Pro Gln Leu Leu Arg Phe Phe
130                 135                 140
His Lys Asn Glu Ile Trp Tyr Arg Thr Glu Gln Ala Ala Val Ala Arg
145                 150                 155                 160
Cys Gln Cys Lys Gly Pro Asp Ala His Cys Gln Arg Leu Ala Ser Gln
                165                 170                 175
Ala Cys Arg Thr Asn Pro Cys Leu His Gly Gly Arg Cys Leu Glu Val
            180                 185                 190
Glu Gly His Arg Leu Cys His Cys Pro Val Gly Tyr Thr Gly Pro Phe
            195                 200                 205
Cys Asp Val Asp Thr Lys Ala Ser Cys Tyr Asp Gly Arg Gly Leu Ser
            210                 215                 220
Tyr Arg Gly Leu Ala Arg Thr Thr Leu Ser Gly Ala Pro Cys Gln Pro
225                 230                 235                 240
Trp Ala Ser Glu Ala Thr Tyr Arg Asn Val Thr Ala Glu Gln Ala Arg
                245                 250                 255
Asn Trp Gly Leu Gly Gly His Ala Phe Cys Arg Asn Pro Asp Asn Asp
            260                 265                 270
Ile Arg Pro Trp Cys Phe Val Leu Asn Arg Asp Arg Leu Ser Trp Glu
            275                 280                 285
Tyr Cys Asp Leu Ala Gln Cys Gln Thr Pro Thr Gln Ala Ala Pro Pro
            290                 295                 300
Thr Pro Val Ser Pro Arg Leu His Val Pro Leu Met Pro Ala Gln Pro
305                 310                 315                 320
Ala Pro Pro Lys Pro Gln Pro Thr Thr Arg Thr Pro Pro Gln Ser Gln
                325                 330                 335
Thr Pro Gly Ala Leu Pro Ala Lys Arg Glu Gln Pro Pro Ser Leu Thr
            340                 345                 350
Arg Asn Gly Pro Leu Ser Cys Gly Gln Arg Leu Arg Lys Ser Leu Ser
            355                 360                 365
Ser Met Thr Arg Val Val Gly Gly Leu Val Ala Leu Arg Gly Ala His
            370                 375                 380
Pro Tyr Ile Ala Ala Leu Tyr Trp Gly His Ser Phe Cys Ala Gly Ser
385                 390                 395                 400
Leu Ile Ala Pro Cys Trp Val Leu Thr Ala Ala His Cys Leu Gln Asp
                405                 410                 415
Arg Pro Ala Pro Glu Asp Leu Thr Val Val Leu Gly Gln Glu Arg Arg
            420                 425                 430
Asn His Ser Cys Glu Pro Cys Gln Thr Leu Ala Val Arg Ser Tyr Arg
            435                 440                 445
Leu His Glu Ala Phe Ser Pro Val Ser Tyr Gln His Asp Leu Ala Leu
            450                 455                 460
Leu Arg Leu Gln Glu Asp Ala Asp Gly Ser Cys Ala Leu Leu Ser Pro
465                 470                 475                 480
Tyr Val Gln Pro Val Cys Leu Pro Ser Gly Ala Ala Arg Pro Ser Glu
                485                 490                 495
Thr Thr Leu Cys Gln Val Ala Gly Trp Gly His Gln Phe Glu Gly Ala
            500                 505                 510
Glu Glu Tyr Ala Ser Phe Leu Gln Glu Ala Gln Val Pro Phe Leu Ser
            515                 520                 525
Leu Glu Arg Cys Ser Ala Pro Asp Val His Gly Ser Ser Ile Leu Pro
```

```
                    530                 535                 540
Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575

Arg Leu Thr Leu Gln Gly Ile Ile Ser Trp Gly Ser Gly Cys Gly Asp
                580                 585                 590

Arg Asn Lys Pro Gly Val Tyr Thr Asp Val Ala Tyr Tyr Leu Ala Trp
                595                 600                 605

Ile Arg Glu His Thr Val Ser
                610                 615

<210> SEQ ID NO 6
<211> LENGTH: 19
<212> TYPE: PRT
<213> ORGANISM: Homo sapiens

<400> SEQUENCE: 6

Met Arg Ala Leu Leu Leu Leu Gly Phe Leu Leu Val Ser Leu Glu Ser
1               5                   10                  15

Thr Leu Ser

<210> SEQ ID NO 7
<211> LENGTH: 353
<212> TYPE: PRT
<213> ORGANISM: Homo sapiens

<400> SEQUENCE: 7

Ile Pro Pro Trp Glu Ala Pro Lys Glu His Lys Tyr Lys Ala Glu Glu
1               5                   10                  15

His Thr Val Val Leu Thr Val Thr Gly Glu Pro Cys His Phe Pro Phe
                20                  25                  30

Gln Tyr His Arg Gln Leu Tyr His Lys Cys Thr His Lys Gly Arg Pro
            35                  40                  45

Gly Pro Gln Pro Trp Cys Ala Thr Thr Pro Asn Phe Asp Gln Asp Gln
    50                  55                  60

Arg Trp Gly Tyr Cys Leu Glu Pro Lys Lys Val Lys Asp His Cys Ser
65                  70                  75                  80

Lys His Ser Pro Cys Gln Lys Gly Gly Thr Cys Val Asn Met Pro Ser
                85                  90                  95

Gly Pro His Cys Leu Cys Pro Gln His Leu Thr Gly Asn His Cys Gln
            100                 105                 110

Lys Glu Lys Cys Phe Glu Pro Gln Leu Leu Arg Phe Phe His Lys Asn
        115                 120                 125

Glu Ile Trp Tyr Arg Thr Glu Gln Ala Ala Val Ala Arg Cys Gln Cys
130                 135                 140

Lys Gly Pro Asp Ala His Cys Gln Arg Leu Ala Ser Gln Ala Cys Arg
145                 150                 155                 160

Thr Asn Pro Cys Leu His Gly Gly Arg Cys Leu Glu Val Glu Gly His
                165                 170                 175

Arg Leu Cys His Cys Pro Val Gly Tyr Thr Gly Pro Phe Cys Asp Val
            180                 185                 190

Asp Thr Lys Ala Ser Cys Tyr Asp Gly Arg Gly Leu Ser Tyr Arg Gly
        195                 200                 205

Leu Ala Arg Thr Thr Leu Ser Gly Ala Pro Cys Gln Pro Trp Ala Ser
210                 215                 220
```

```
Glu Ala Thr Tyr Arg Asn Val Thr Ala Glu Gln Ala Arg Asn Trp Gly
225                 230                 235                 240

Leu Gly Gly His Ala Phe Cys Arg Asn Pro Asp Asn Asp Ile Arg Pro
            245                 250                 255

Trp Cys Phe Val Leu Asn Arg Asp Arg Leu Ser Trp Glu Tyr Cys Asp
        260                 265                 270

Leu Ala Gln Cys Gln Thr Pro Thr Gln Ala Ala Pro Pro Thr Pro Val
    275                 280                 285

Ser Pro Arg Leu His Val Pro Leu Met Pro Ala Gln Pro Ala Pro Pro
290                 295                 300

Lys Pro Gln Pro Thr Thr Arg Thr Pro Pro Gln Ser Gln Thr Pro Gly
305                 310                 315                 320

Ala Leu Pro Ala Lys Arg Glu Gln Pro Pro Ser Leu Thr Arg Asn Gly
                325                 330                 335

Pro Leu Ser Cys Gly Gln Arg Leu Arg Lys Ser Leu Ser Ser Met Thr
            340                 345                 350

Arg

<210> SEQ ID NO 8
<211> LENGTH: 243
<212> TYPE: PRT
<213> ORGANISM: Homo sapiens

<400> SEQUENCE: 8

Val Val Gly Gly Leu Val Ala Leu Arg Gly Ala His Pro Tyr Ile Ala
1               5                   10                  15

Ala Leu Tyr Trp Gly His Ser Phe Cys Ala Gly Ser Leu Ile Ala Pro
            20                  25                  30

Cys Trp Val Leu Thr Ala Ala His Cys Leu Gln Asp Arg Pro Ala Pro
        35                  40                  45

Glu Asp Leu Thr Val Val Leu Gly Gln Glu Arg Arg Asn His Ser Cys
50                  55                  60

Glu Pro Cys Gln Thr Leu Ala Val Arg Ser Tyr Arg Leu His Glu Ala
65                  70                  75                  80

Phe Ser Pro Val Ser Tyr Gln His Asp Leu Ala Leu Leu Arg Leu Gln
            85                  90                  95

Glu Asp Ala Asp Gly Ser Cys Ala Leu Leu Ser Pro Tyr Val Gln Pro
            100                 105                 110

Val Cys Leu Pro Ser Gly Ala Ala Arg Pro Ser Glu Thr Thr Leu Cys
        115                 120                 125

Gln Val Ala Gly Trp Gly His Gln Phe Glu Gly Ala Glu Glu Tyr Ala
    130                 135                 140

Ser Phe Leu Gln Glu Ala Gln Val Pro Phe Leu Ser Leu Glu Arg Cys
145                 150                 155                 160

Ser Ala Pro Asp Val His Gly Ser Ser Ile Leu Pro Gly Met Leu Cys
                165                 170                 175

Ala Gly Phe Leu Glu Gly Gly Thr Asp Ala Cys Gln Gly Asp Ser Gly
            180                 185                 190

Gly Pro Leu Val Cys Glu Asp Gln Ala Ala Glu Arg Arg Leu Thr Leu
        195                 200                 205

Gln Gly Ile Ile Ser Trp Gly Ser Gly Cys Gly Asp Arg Asn Lys Pro
    210                 215                 220

Gly Val Tyr Thr Asp Val Ala Tyr Tyr Leu Ala Trp Ile Arg Glu His
225                 230                 235                 240
```

Thr Val Ser

<210> SEQ ID NO 9
<211> LENGTH: 1794
<212> TYPE: DNA
<213> ORGANISM: Mus musculus
<220> FEATURE:
<221> NAME/KEY: misc_feature
<222> LOCATION: (1)..(57)
<223> OTHER INFORMATION: Signal Peptide
<220> FEATURE:
<221> NAME/KEY: misc_feature
<222> LOCATION: (58)..(1062)
<223> OTHER INFORMATION: Heavy Chain
<220> FEATURE:
<221> NAME/KEY: misc_feature
<222> LOCATION: (1063)..(1791)
<223> OTHER INFORMATION: Light Chain

<400> SEQUENCE: 9

| | |
|---|---|
| atgacggctc tgttgttcct ggggtctctg ctgatgagtc tggatctgac actttcggct | 60 |
| ccaccatgga aagactccaa gaaatttaag gacgcacctg atgggcccac agtggttctc | 120 |
| actgtggatg ggaggctctg ccattttccc tttcagtacc accgtcagct acaccacaaa | 180 |
| tgcatccaca aaaggcggcc aggctcccgc ccctggtgtg ctaccacccc caactttgat | 240 |
| gaagatcagc aatggggata ctgcttggag cccaagaaag tgaaagacca ttgcagcaaa | 300 |
| cacaacccgt gccacaaagg agggacatgt atcaacaccc caatgggcc acactgtctc | 360 |
| tgccctgaac acctcactgg gaaacattgc cagaaagaga aatgctttga gcctcagctt | 420 |
| ctcaagttct ccacgagaaa tgagctatgg tttagaacgg ggccaggagg tgtggccagg | 480 |
| tgcgagtgca aaggttctga ggctcactgc aagccggtgg ccagccaggc tgcagcatc | 540 |
| aatccgtgcc ttaatggggg cagctgcctc tcgtggagg accacccact gtgccgttgc | 600 |
| cctacaggct acactggata ttttgcgac ttggaccttt gggcgacctg ctatgaaggc | 660 |
| aggggctca gctaccgggg ccaggctgga actacgcaat cgggtgcgcc atgtcagcgg | 720 |
| tggaccgtgg aggccaccta ccggaacatg actgagaagc aagcgctaag ctggggcctg | 780 |
| ggccaccacg cattttgccg gaacccagat aatgacacac gtccatggtg cttcgtctgg | 840 |
| agtggcgaca ggctgagctg ggactattgc ggcctggagc agtgccagac gccaacgttt | 900 |
| gcacctctag ttgtccctga gagtcaggag gagtccccgt cccaggcacc atctctgtcc | 960 |
| catgcaccaa atgactcgac cgatcatcag acttctctgt ccaagaccaa cacgatgggc | 1020 |
| tgcggacaga ggttccgcaa gggactgtcc tcgttcatgc gcgtggtggg cggactagtg | 1080 |
| gctctgcctg ggtcgcaccc ctacatcgct gcactgtact ggggtaacaa cttctgcgcg | 1140 |
| ggcagtctca tcgcccctg ttgggtgctg accgcggctc actgcctgca gaatcggcca | 1200 |
| gcgcccgagg aactgacagt ggtacttggt caagatcgcc acaaccagag ctgcgagtgg | 1260 |
| tgccagactc tggctgtgcg ctcctaccgc cttcacgagg gcttctcctc catcacctac | 1320 |
| cagcacgact ggctctgct gcgcctgcag gaaagcaaaa ccaacagttg cgcgatcctg | 1380 |
| tcacctcacg ttcagcctgt gtgtctaccc agcggcgcgg ccccacctc tgagacagtg | 1440 |
| ctctgcgagg tggccggctg gggtcaccag ttcgagggg ctgaagaata tccaccttc | 1500 |
| ctgcaggagg cacaggttcc ctttatcgcc ctggatcgct gctccaactc taacgtgcac | 1560 |
| ggagacgcca ttctccctgg gatgcttgc gctggcttct tggagggagg caccgatgcc | 1620 |
| tgccagggtg actccggggg ccctctggtg tgtgaggaag gaactgcaga acatcagctc | 1680 |

```
accctgcgcg gagtcatcag ctggggctcc ggctgtggtg accgcaacaa gcccggagtc      1740
tacacagacg tggccaacta cctggcttgg atccagaagc atattgcttc ataa            1794

<210> SEQ ID NO 10
<211> LENGTH: 57
<212> TYPE: DNA
<213> ORGANISM: Mus musculus

<400> SEQUENCE: 10
atgacggctc tgttgttcct ggggtctctg ctgatgagtc tggatctgac actttcg         57

<210> SEQ ID NO 11
<211> LENGTH: 1005
<212> TYPE: DNA
<213> ORGANISM: Mus musculus

<400> SEQUENCE: 11
gctccaccat ggaaagactc caagaaattt aaggacgcac ctgatgggcc cacagtggtt      60
ctcactgtgg atgggaggct ctgccatttt ccctttcagt accaccgtca gctacaccac     120
aaatgcatcc acaaaaggcg gccaggctcc cgcccctggt gtgctaccac ccccaacttt     180
gatgaagatc agcaatgggg atactgcttg gagcccaaga agtgaaagaa ccattgcagc     240
aaacacaacc cgtgccacaa aggagggaca tgtatcaaca ccccaatgg gccacactgt     300 ctctgccctg aacacctcac tgggaaacat tgccagaaag agaaatgctt tgagcctcag     360
cttctcaagt tcttccacga gaatgagcta tggtttagaa cggggccagg aggtgtggcc     420
aggtgcgagt gcaaaggttc tgaggctcac tgcaagccgg tggccagcca ggcctgcagc     480
atcaatccgt gccttaatgg gggcagctgc ctcctcgtgg aggaccaccc actgtgccgt     540
tgccctacag gctacactgg atattttgtgc gacttggacc tttgggcgac ctgctatgaa     600 ggcaggggc tcagctaccg gggccaggct ggaactacgc aatcgggtgc gccatgtcag     660
cggtggaccg tggaggccac ctaccggaac atgactgaga agcaagcgct aagctggggc     720
ctgggccacc acgcattttg ccggaaccca gataatgaca cacgtccatg gtgcttcgtc     780
tggagtggcg acaggctgag ctgggactat tgccggcctgg agcagtgcca gacgccaacg     840
tttgcacctc tagttgtccc tgagagtcag gaggagtccc cgtcccaggc accatctctg     900
tcccatgcac caaatgactc gaccgatcat cagacttctc tgtccaagac caacacgatg     960
ggctgcggac agaggttccg caagggactg tcctcgttca tgcgc                      1005

<210> SEQ ID NO 12
<211> LENGTH: 729
<212> TYPE: DNA
<213> ORGANISM: Mus musculus

<400> SEQUENCE: 12
gtggtgggcg gactagtggc tctgcctggg tcgcacccct acatcgctgc actgtactgg      60
ggtaacaact tctgcgcggg cagtctcatc gcccctgtt gggtgctgac cgcggctcac     120
tgcctgcaga atcggccagc gcccgaggaa ctgacagtgg tacttggtca agatcgccac     180
aaccagagct gcgagtggtg ccagactctg gctgtgcgct cctaccgcct tcacgagggc     240
ttctcctcca tcacctacca gcacgacttg gctctgctgc gcctgcagga agcaaaaacc     300
aacagttgcg cgatcctgtc acctcacgtt cagcctgtgt gtctacccag cggcgcggcc     360
ccaccctctg agacagtgct ctgcgaggtg gccggctggg gtcaccagtt cgaggggct     420 gaagaatact ccaccttcct gcaggaggca caggttccct ttatcgccct ggatcgctgc     480
```

| tccaactcta acgtgcacgg agacgccatt ctccctggga tgctttgcgc tggcttcttg | 540 |
| gagggaggca ccgatgcctg ccagggtgac tccgggggcc ctctggtgtg tgaggaagga | 600 |
| actgcagaac atcagctcac cctgcgcgga gtcatcagct ggggctccgg ctgtggtgac | 660 |
| cgcaacaagc ccggagtcta cacagacgtg gccaactacc tggcttggat ccagaagcat | 720 |
| attgcttca | 729 |

<210> SEQ ID NO 13
<211> LENGTH: 1848
<212> TYPE: DNA
<213> ORGANISM: Homo sapiens
<220> FEATURE:
<221> NAME/KEY: misc_feature
<222> LOCATION: (1)..(57)
<223> OTHER INFORMATION: Signal Peptide
<220> FEATURE:
<221> NAME/KEY: misc_feature
<222> LOCATION: (58)..(1116)
<223> OTHER INFORMATION: Heavy Chain
<220> FEATURE:
<221> NAME/KEY: misc_feature
<222> LOCATION: (1117)..(1845)
<223> OTHER INFORMATION: Light Chain

<400> SEQUENCE: 13

| atgagggctc tgctgctcct ggggttcctg ctggtgagct ggagtcaac actttcgatt | 60 |
| ccaccttggg aagcccccaa ggagcataag tacaaagctg aagagcacac agtcgttctc | 120 |
| actgtcaccg gggagccctg ccacttcccc ttccagtacc accggcagct gtaccacaaa | 180 |
| tgtacccaca agggccggcc aggccctcag ccctggtgtg ctaccacccc caactttgat | 240 |
| caggaccagc gatggggata ctgtttggag cccaagaaag tgaaagacca ctgcagcaaa | 300 |
| cacagcccct gccagaaagg agggacctgt gtgaacatgc caagcggccc ccactgtctc | 360 |
| tgtccacaac acctcactgg aaaccactgc cagaaagaga agtgctttga gcctcagctt | 420 |
| ctccggtttt tccacaagaa tgagatatgg tatagaactg agcaagcagc gtggccaga | 480 |
| tgccagtgca agggtcctga tgcccactgc agcggctgg ccagccaggc ctgccgcacc | 540 |
| aacccgtgcc tccatggggg tcgctgccta gaggtggagg ccaccgcct gtgccactgc | 600 |
| ccggtgggct acaccggacc cttctgcgac gtggacacca aggcaagctg ctatgatggc | 660 |
| cgcgggctca gctaccgcgg cctggccagg accacgctct cggtgcgcc ctgtcagccg | 720 |
| tgggcctcgg aggccaccta ccggaacgtg actgccgagc aagcgcggaa ctggggactg | 780 |
| ggcggccacg ccttctgccg gaacccggac aacgacatcc gcccgtggtg cttcgtgctg | 840 |
| aaccgcgacc ggctgagctg ggagtactgc gacctggcac agtgccagac cccaacccag | 900 |
| gcggcgcctc cgacccccgt gtcccctagg cttcatgtcc cactcatgcc cgcgcagccg | 960 |
| gcaccgccga agcctcagcc cacgacccgg acccgcctc agtcccagac cccgggagcc | 1020 |
| ttgccggcga gcgggagca gccgccttcc ctgaccagga acggcccact gagctgcggg | 1080 |
| cagcggctcc gcaagagtct gtcttcgatg accgcgtcg ttggcgggct ggtggcgcta | 1140 |
| cgcgggggcg ccccctacat cgccgcgctg tactggggcc acagtttctg cgccggcagc | 1200 |
| ctcatcgccc cctgctggt gctgacggcc gctcactgcc tgcaggaccg gccgcaccc | 1260 |
| gaggatctga cggtggtgct cggccaggaa cgccgtaacc acagctgtga gccgtgccag | 1320 |
| acgttggccg tgcgctccta ccgcttgcac gaggccttct cgcccgtcag ctaccagcac | 1380 |
| gacctggctc tgttgcgcct tcaggaggat gcggacggca gctgcgcgct cctgtcgcct | 1440 |

| | |
|---|---|
| tacgttcagc cggtgtgcct gccaagcggc gccgcgcgac cctccgagac cacgctctgc | 1500 |
| caggtggccg gctggggcca ccagttcgag ggggcggagg aatatgccag cttcctgcag | 1560 |
| gaggcgcagg taccgttcct ctccctggag cgctgctcag ccccggacgt gcacggatcc | 1620 |
| tccatcctcc ccggcatgct ctgcgcaggg ttcctcgagg gcggcaccga tgcgtgccag | 1680 |
| ggtgattccg gaggcccgct ggtgtgtgag gaccaagctg cagagcgccg gctcaccctg | 1740 |
| caaggcatca tcagctgggg atcgggctgt ggtgaccgca acaagccagg cgtctacacc | 1800 |
| gatgtggcct actacctggc ctggatccgg gagcacaccg tttcctga | 1848 |

<210> SEQ ID NO 14
<211> LENGTH: 57
<212> TYPE: DNA
<213> ORGANISM: Homo sapiens

<400> SEQUENCE: 14

| | |
|---|---|
| atgagggctc tgctgctcct ggggttcctg ctggtgagct tggagtcaac actttcg | 57 |

<210> SEQ ID NO 15
<211> LENGTH: 1059
<212> TYPE: DNA
<213> ORGANISM: Homo sapiens

<400> SEQUENCE: 15

| | |
|---|---|
| attccacctt gggaagcccc caaggagcat aagtacaaag ctgaagagca cacagtcgtt | 60 |
| ctcactgtca ccggggagcc ctgccacttc cccttccagt accaccggca gctgtaccac | 120 |
| aaatgtaccc acaagggccg gccaggccct cagccctggt gtgctaccac ccccaacttt | 180 |
| gatcaggacc agcgatgggg atactgtttg gagcccaaga agtgaaaga ccactgcagc | 240 |
| aaacacagcc cctgccagaa aggagggacc tgtgtgaaca tgccaagcgg cccccactgt | 300 |
| ctctgtccac aacacctcac tggaaaccac tgccagaaag agaagtgctt tgagcctcag | 360 |
| cttctccggt ttttccacaa gaatgagata tggtatagaa ctgagcaagc agctgtggcc | 420 |
| agatgccagt gcaagggtcc tgatgcccac tgccagcggc tggccagcca ggcctgccgc | 480 |
| accaacccgt gcctccatgg gggtcgctgc ctagaggtgg agggccaccg cctgtgccac | 540 |
| tgcccggtgg gctacaccgg acccttctgc gacgtggaca ccaaggcaag ctgctatgat | 600 |
| ggccgcgggg tcagctaccg cggcctggcc aggaccacgc tctcgggtgc gcctgtcag | 660 |
| ccgtgggcct cggaggccac ctaccggaac gtgactgccg agcaagcgcg gaactgggga | 720 |
| ctgggcggca cgccttctg ccggaacccg acaacgaca tccgcccgtg gtgcttcgtg | 780 |
| ctgaaccgcg accggctgag ctgggagtac tgcgacctgg cacagtgcca gaccccaacc | 840 |
| caggcggcgc ctccgacccc ggtgtcccct aggcttcatg tcccactcat gcccgcgcag | 900 |
| ccggcaccgc cgaagcctca gcccacgacc cggacccccg ctcagtccca gaccccggga | 960 |
| gccttgccgg cgaagcggga gcagccgcct tccctgacca ggaacggccc actgagctgc | 1020 |
| gggcagcggc tccgcaagag tctgtcttcg atgacccgc | 1059 |

<210> SEQ ID NO 16
<211> LENGTH: 729
<212> TYPE: DNA
<213> ORGANISM: Homo sapiens

<400> SEQUENCE: 16

| | |
|---|---|
| gtcgttggcg ggctggtggc gctacgcggg gcgcacccct acatcgccgc gctgtactgg | 60 |
| ggccacagtt tctgcgccgg cagcctcatc gcccctgct gggtgctgac ggccgctcac | 120 |

```
tgcctgcagg accggcccgc acccgaggat ctgacggtgg tgctcggcca ggaacgccgt    180
aaccacagct gtgagccgtg ccagacgttg gccgtgcgct cctaccgctt gcacgaggcc    240
ttctcgcccg tcagctacca gcacgacctg gctctgttgc gccttcagga ggatgcggac    300
ggcagctgcg cgctcctgtc gccttacgtt cagccggtgt gcctgccaag cggcgccgcg    360
cgaccctccg agaccacgct ctgccaggtg gccggctggg ccaccagtt cgaggggcg    420 gaggaatatg ccagcttcct gcaggaggcg caggtaccgt tcctctccct ggagcgctgc    480
tcagccccgg acgtgcacgg atcctccatc ctccccggca tgctctgcgc agggttcctc    540
gagggcggca ccgatgcgtg ccagggtgat tccggaggcc cgctggtgtg tgaggaccaa    600
gctgcagagc gccggctcac cctgcaaggc atcatcagct ggggatcggg ctgtggtgac    660
cgcaacaagc caggcgtcta caccgatgtg gcctactacc tggcctggat ccgggagcac    720
accgtttcc                                                           729
```

```
<210> SEQ ID NO 17
<211> LENGTH: 12176
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: Mouse Sequence
<220> FEATURE:
<221> NAME/KEY: misc_feature
<222> LOCATION: (20)..(3893)
<223> OTHER INFORMATION: Human Sequence
<220> FEATURE:
<221> NAME/KEY: misc_feature
<222> LOCATION: (20)..(22)
<223> OTHER INFORMATION: Start Codon
<220> FEATURE:
<221> NAME/KEY: misc_feature
<222> LOCATION: (3742)..(3812)
<223> OTHER INFORMATION: Exon 4
<220> FEATURE:
<221> NAME/KEY: misc_feature
<222> LOCATION: (3894)..(8703)
<223> OTHER INFORMATION: Neo Self-Deleting Cassette
<220> FEATURE:
<221> NAME/KEY: misc_feature
<222> LOCATION: (3894)..(3899)
<223> OTHER INFORMATION: XhoI
<220> FEATURE:
<221> NAME/KEY: misc_feature
<222> LOCATION: (3900)..(3933)
<223> OTHER INFORMATION: LoxP
<220> FEATURE:
<221> NAME/KEY: misc_feature
<222> LOCATION: (8632)..(8665)
<223> OTHER INFORMATION: LoxP
<220> FEATURE:
<221> NAME/KEY: misc_feature
<222> LOCATION: (8672)..(8697)
<223> OTHER INFORMATION: I_Ceu
<220> FEATURE:
<221> NAME/KEY: misc_feature
<222> LOCATION: (8698)..(8703)
<223> OTHER INFORMATION: NheI
<220> FEATURE:
<221> NAME/KEY: misc_feature
<222> LOCATION: (8704)..(12065)
<223> OTHER INFORMATION: Human Sequence
<220> FEATURE:
<221> NAME/KEY: misc_feature
<222> LOCATION: (8924)..(9034)
<223> OTHER INFORMATION: Exon 5
<220> FEATURE:
```

```
<221> NAME/KEY: misc_feature
<222> LOCATION: (9172)..(9303)
<223> OTHER INFORMATION: Exon 6
<220> FEATURE:
<221> NAME/KEY: misc_feature
<222> LOCATION: (9443)..(9547)
<223> OTHER INFORMATION: Exon 7
<220> FEATURE:
<221> NAME/KEY: misc_feature
<222> LOCATION: (12063)..(12065)
<223> OTHER INFORMATION: Stop Codon
<220> FEATURE:
<221> NAME/KEY: misc_feature
<222> LOCATION: (12066)..(12176)
<223> OTHER INFORMATION: Mouse Sequence

<400> SEQUENCE: 17
ggggccatcg gcagacgcca tgagggctct gctgctcctg gggttcctgc tggtgagctt      60
ggagtcaaca ctttcggtga gtgctgtggg aaccaggatt gtcccaggat tgttctgggg    120
ggtcgctatc acagccatga gccatggcct ctgctcatga cctgtgggtc caggtgacta    180
ggaggcctat gtggaaaggt gaggccagcc cggaaggccc aggcagagga cagacaac     240
cagactgggt ggatacaagg gcacagcctg catttctggg ggagatgggc cttaagaaga    300
caacgggggg aggtagaaag ggtttgggtc ttgggaagaa atctctgcat ttctgggctg    360
tgagaggaag ctgcagacta gcaacagatc ggtggcaggc tatgacttat agtcagttcc    420
ctgccttctt ctctcccttg tagattccac cttgggaagc cccaaggag cataagtaca     480
aagctgaaga gcacacagtc ggtaagtggc ctggctcctc ctcccgggaa cccttgggtg    540
gggatgtgta tggtgcagtg tgtgcagtct cagggcagtc tagtctagtg cctacctggt    600
gctaggtctt atgcccatgg gcactagagt gatcgtgagc tgtgtgatcc ttgagggcag    660
ggtatgggct gtgtctaagt gcccacgagc ctggctcgga gcaggtgctt gagatatgtg    720
ctgctggcgc catcacacct gggctcctgc cagccttcct cagtttcccc agcttctccc    780
cttctttttcc tttccccagt acgtctcatg ggcatcattc atgccacaca gaggccaggg    840
ccttcaatgg gcaaggaagg atcaagagct tgtctctggc atctgaatgc ctctgaagcc    900
cagctttatc acttatgagc tgggtgactc tgggcgaggg atttgagttc tccaagcttc    960
aatttcccct tctgtgaaac caggttgata acagtaaacc tcttagggtt gttgagaagg   1020
gaaacccatg tgaggtattc agcccatcac ctggtgcatg gaaatgcttt acaaatatta   1080
gcttttatta tgaaactacc ttttagatga agggtacctg ccatttcccc cttcctcaag   1140
ctctgccata gctccccatt gctttcattc ttccagacac taaattacct acatgccagg   1200
catggtggct catgcctgta atcccagcac tttgggaggc caaggtcggt ggatcatgag   1260
gtcaggagtt cgagaccagc ctggccaaca tggtgaaatg ctgtctctac taaaagtaca   1320
aaaattagcc aggcatggtg gcatgcgcca gtagtcccag ctactcggga ggctgaggca   1380
gaagaattgc ttgaacctgg gaggtgaagg ttgcagtgaa cgaagatcac accattgcac   1440
tccagcttgg gcaacacagc aagactccgt ctcaaaaaaa aaaaaaaaat ttacctagag   1500
tgtggcacat agcagggcct gtgaaccaga tggaccttac cctggtgggc ctgacttggt   1560
gggggttgagt ctctaagcat ggcgttgagg cccagcacat tccaaccctg gactccctca   1620
gcctcctctc ttcaccccac acccaaaagt ttctcctctc tcttgcctta cccaaacttg   1680
gtgccctatc cttgcctaat cccctgccta aggtcccct cctctctgtc cgtccatccc    1740
atctgcatct tttttttttt ttgagatgga gtctcgctct gtccctagg ctagagtgca    1800
atggcgcgat cttggctcat tgcaacctcc gcctcctggg ttcaagcgat tctctgcctc   1860
```

-continued

```
agcctcccga gttgctggga ttacaggcac acaacttcat gctcagctaa ttttgtatt    1920 ttttagtaga gacagggttt caccatgttg gccaggctgg tctcgaactc ctgccctcag    1980
gtggtccgcc caccttagcc tcccaaagtg ctgggattac aggcgtgagc caccgcgcct    2040
ggcccccatt tgcatcttaa aggtccatct cagatccatt tccatttact gtcctagttc    2100
tggtttggtc cttggcaagt gcactttgcc ttgaacaaaa tagtggcaaa gcttattga     2160 gcaggtactt tgtgccagac actgctcagc atttcatggc attatctcat gaagcccac     2220 gacaattcct ctgaagaaga cacaggcaat tctcattatt cgcgatggtt atgttctata    2280
aaatcacagt gaacattgaa ctagcaaaca gtattaggtt cctgtgagcc tctggtcaca    2340 acatttcat caaccaacag catataatct ggttttatgt atgattctgt ttaaagacat     2400
tttatttagt atatgtgttg ctgattcatc aatgctaagc tgatggcact atagcacaca    2460
cctgaatcaa gtgtctaaca cacgctttct ccctaaggta gccttcttgt gcttaggaac    2520
tacacagctc ttcagcagga ggctcagagg ccatttccaa aagccaaatc ccagcaaaa     2580 gcacaaagtg tgaaaaacgt tgcactaagt agactgagaa ggacactcat tcaataggag    2640
agctgaaaca gcagcagca gcgtgacgcc ttgttgaacc ttaactggga atgtgcaaat     2700
ttttcactgc tctgtgcatg cccacaaatg gccatgaaaa catttcaagt attgacttgg    2760
gagttacaaa taaaattcag caagtaggca cattctcaat gtagaaccag agaagaatga    2820
ggatcaactg tactattatt actgccgttt tacagataag gaaaccaagg ctcagatcag    2880
agtggttaac agtgacttca acattcaaca agtattatta agtgcctact ttgtggcaag    2940
tgctcttcct ggccttggga ctgaagactt acccaaggtc acacagctag caggttgtgg    3000
agtcaggagt ctactccagc tatctgactc ctgaacccaa gttttttttt ttttctttaa    3060
gatggagtct cactctgtca cccaggctgg agtgcagtgg cgcgatctcg gctcactgca    3120
agctccgcct cccgggttca caccattctc ctgcctcggc ctcccgagta gctgggacta    3180
caggcacctg ccaccacccc cagctaattt ttttgtattt ttagtagaga ggggttca     3240 ctgtattagc caggatggtc ttgatctcct gacctcgtga tctgcccgcc ttggcctccc    3300
aaagtgctgg gattacaggc ttgagccacc gcgcccggcc ctgaacccaa cttttagagc    3360
agaaagtgtt ttcaatgcac agcgaccttt tgagggtct gtccttttcc tgaccagacc    3420
ctgagggaca gtgcctgagc agttgagtac aggggaagtc ctcagagagt gtgttgtccc    3480
tgcagttctc actgtcaccg gggagccctg ccacttcccc ttccagtacc accggcagct    3540
gtaccacaaa tgtacccaca agggccggcc aggccctcag ccctggtaag actacgcaga    3600
ggagttggag caggggcctg ggagacatgt accctgcctg tccttctgtc caaggaactc    3660
tgcttggaga gagggactg tgatagggca gggtgggcca ggccctggg tagagcaggg     3720 aagccttgtc tctttctaca ggtgtgctac caccccaac tttgatcagg accagcgatg     3780
gggatactgt ttggagccca agaaagtgaa aggtgctaca cacagcctct ggggtggcct    3840
ggggctctct cctcccgcct cattactctc ctggtatcac cagaccccac acactcgaga    3900
taacttcgta taatgtatgc tatacgaagt tatatgcatg ccagtagcag cacccacgtc    3960
caccttctgt ctagtaatgt ccaacacctc cctcagtcca aacactgctc tgcatccatg    4020
tggctcccat ttatacctga agcacttgat ggggcctcaa tgttttacta gagcccaccc    4080
ccctgcaact ctgagaccct ctggatttgt ctgtcagtgc ctcactgggg cgttggataa    4140
tttcttaaaa ggtcaagttc cctcagcagc attctctgag cagtctgaag atgtgtgctt    4200
```

```
ttcacagttc aaatccatgt ggctgtttca cccacctgcc tggccttggg ttatctatca   4260
ggacctagcc tagaagcagg tgtgtggcac ttaacaccta agctgagtga ctaactgaac   4320
actcaagtgg atgccatctt tgtcacttct tgactgtgac acaagcaact cctgatgcca   4380
aagccctgcc caccctctc atgcccatat ttggacatgg tacaggtcct cactggccat    4440
ggtctgtgag gtcctggtcc tctttgactt cataattcct aggggccact agtatctata   4500
agaggaagag ggtgctggct cccaggccac agcccacaaa attccacctg ctcacaggtt   4560
ggctggctcg acccaggtgg tgtccctgc tctgagccag ctcccggcca agccagcacc    4620
atgggaaccc ccaagaagaa gaggaaggtg cgtaccgatt taaattccaa tttactgacc   4680
gtacaccaaa atttgcctgc attaccggtc gatgcaacga gtgatgaggt tcgcaagaac   4740
ctgatggaca tgttcaggga tcgccaggcg ttttctgagc atacctggaa aatgcttctg   4800
tccgtttgcc ggtcgtgggc ggcatggtgc aagttgaata ccggaaatg  gtttcccgca   4860
gaacctgaag atgttcgcga ttatcttcta tatcttcagg cgcgcggtct ggcagtaaaa   4920
actatccagc aacatttggg ccagctaaac atgcttcatc gtcggtccgg gctgccacga   4980
ccaagtgaca gcaatgctgt ttcactggtt atgcggcgga tccgaaaaga aaacgttgat   5040
gccggtgaac gtgcaaaaca ggtaaatata aaatttttaa gtgtataatg atgttaaact   5100
actgattcta attgtttgtg tattttaggc tctagcgttc gaacgcactg atttcgacca   5160
ggttcgttca ctcatggaaa atagcgatcg ctgccaggat atacgtaatc tggcatttct   5220
ggggattgct tataacaccc tgttacgtat agccgaaatt gccaggatca gggttaaaga   5280
tatctcacgt actgacggtg ggagaatgtt aatccatatt ggcagaacga aaacgctggt   5340
tagcaccgca ggtgtagaga aggcacttag cctgggggta actaaactgg tcgagcgatg   5400
gatttccgtc tctggtgtag ctgatgatcc gaataactac ctgttttgcc gggtcagaaa   5460
aaatggtgtt gccgcgccat ctgccaccag ccagctatca actcgcgccc tggaagggat   5520
ttttgaagca actcatcgat tgatttacgg cgctaaggat gactctggtc agagatacct   5580
ggcctggtct ggacacagtg cccgtgtcgg agccgcgcga gatatggccc gcgctggagt   5640
tcaataccg gagatcatgc aagctggtgg ctggaccaat gtaaatattg tcatgaacta   5700
tatccgtaac ctggatagtg aaacagggc aatggtgcgc ctgctggaag atggcgatta   5760
ggcggccggc cgctaatcag ccataccaca tttgtagagg ttttacttgc tttaaaaaac   5820
ctcccacacc tccccctgaa cctgaaacat aaaatgaatg caattgttgt tgttaacttg   5880
tttattgcag cttataatgg ttacaaataa agcaatagca tcacaaattt cacaaataaa   5940
gcatttttt cactgcattc tagttgtggt ttgtccaaac tcatcaatgt atcttatcat    6000
gtctggatcc cccggctaga gtttaaacac tagaactagt ggatccccg ggatcatggc    6060
ctccgcgccg ggttttggcg cctcccgcgg gcgcccccct cctcacggcg agcgctgcca   6120
cgtcagacga agggcgcagc gagcgtcctg atccttccgc ccggacgctc aggacagcgg   6180
cccgctgctc ataagactcg gccttagaac cccagtatca gcagaaggac atttaggac    6240
gggacttggg tgactctagg gcactggttt tctttccaga gagcggaaca ggcgaggaaa   6300
agtagtccct tctcggcgat tctgcggagg atctccgtg gggcggtgaa cgccgatgat    6360
tatataagga cgcgccgggt gtggcacagc tagttccgtc gcagccggga tttgggtcgc   6420
ggttcttgtt tgtggatcgc tgtgatcgtc acttggtgag tagcgggctg ctgggctggc   6480
cggggctttc gtgccgccg gccgctcgg tgggacggaa gcgtgtggag agaccgccaa     6540
gggctgtagt ctgggtccgc gagcaaggtt gccctgaact ggggggttggg gggagcgcag   6600
```

```
caaaatggcg gctgttcccg agtcttgaat ggaagacgct tgtgaggcgg gctgtgaggt   6660
cgttgaaaca aggtgggggg catggtgggc ggcaagaacc caaggtcttg aggccttcgc   6720
taatgcggga aagctcttat tcgggtgaga tgggctgggg caccatctgg ggaccctgac   6780
gtgaagtttg tcactgactg gagaactcgg tttgtcgtct gttgcggggg cggcagttat   6840
ggcggtgccg ttgggcagtg cacccgtacc tttgggagcg cgcgccctcg tcgtgtcgtg   6900
acgtcacccg ttctgttggc ttataatgca gggtgggggcc acctgccggt aggtgtgcgg   6960
taggcttttc tccgtcgcag gacgcagggt tcgggcctag ggtaggctct cctgaatcga   7020
caggcgccag acctctggtg aggggaggga taagtgaggc gtcagtttct ttggtcggtt   7080
ttatgtacct atcttcttaa gtagctgaag ctccggtttt gaactatgcg ctcggggttg   7140
gcgagtgtgt tttgtgaagt ttttaggca ccttttgaaa tgtaatcatt tgggtcaata   7200
tgtaattttc agtgttagac tagtaaattg tccgctaaat tctggccgtt tttggctttt   7260
ttgttagacg tgttgacaat taatcatcgg catagtatat cggcatagta taatacgaca   7320
aggtgaggaa ctaaaccatg ggatcggcca ttgaacaaga tggattgcac gcaggttctc   7380
cggccgcttg ggtggagagg ctattcggct atgactgggc acaacagaca atcggctgct   7440
ctgatgccgc cgtgttccgg ctgtcagcgc agggggcgccc ggttcttttt gtcaagaccg   7500
acctgtccgg tgccctgaat gaactgcagg acgaggcagc gcggctatcg tggctggcca   7560
cgacgggcgt tccttgcgca gctgtgctcg acgttgtcac tgaagcggga agggactggc   7620
tgctattggg cgaagtgccg gggcaggatc tcctgtcatc tcaccttgct cctgccgaga   7680
aagtatccat catggctgat gcaatgcggc ggctgcatac gcttgatccg gctacctgcc   7740
cattcgacca ccaagcgaaa catcgcatcg agcgagcacg tactcggatg gaagccggtc   7800
ttgtcgatca ggatgatctg gacgaagagc atcaggggct cgcgccagcc gaactgttcg   7860
ccaggctcaa ggcgcgcatg cccgacggcg atgatctcgt cgtgacccat ggcgatgcct   7920
gcttgccgaa tatcatggtg gaaaatggcc gcttttctgg attcatcgac tgtggccggc   7980
tgggtgtggc ggaccgctat caggacatag cgttggctac ccgtgatatt gctgaagagc   8040
ttggcggcga atgggctgac cgcttcctcg tgctttacgg tatcgccgct cccgattcgc   8100
agcgcatcgc cttctatcgc cttcttgacg agttcttctg aggggatccg ctgtaagtct   8160
gcagaaattg atgatctatt aaacaataaa gatgtccact aaaatggaag tttttcctgt   8220
catactttgt taagaagggt gagaacagag tacctacatt ttgaatggaa ggattggagc   8280 tacggggggtg ggggtggggt gggattagat aaatgcctgc tctttactga aggctcttta   8340
ctattgcttt atgataatgt ttcatagttg gatatcataa tttaaacaag caaaaccaaa   8400
ttaagggcca gctcattcct cccactcatg atctatagat ctatagatct ctcgtgggat   8460
cattgttttt ctcttgattc ccactttgtg gttctaagta ctgtggtttc caaatgtgtc   8520
agtttcatag cctgaagaac gagatcagca gcctctgttc cacatacact tcattctcag   8580
tattgttttg ccaagttcta attccatcag acctcgacct gcagccccta gataacttcg   8640
tataatgtat gctatacgaa gttatgctag gtaactataa cggtcctaag gtagcgagct   8700
agccctggga ttctggaccc agccccttct ctccctccac aatacccttt ggaagtccag   8760
agggagagtt ctgggaagga gtggtcccat tttgcaggtg ggtaaaccaa gcttggaaac   8820
ttggagtagc aaggtcacaa ggcaagtagg ttcaagaagg gccttggccc ccagctgtgt   8880
gactcagctc cctgctcttc cttccaccat gtccatctct cagaccactg cagcaaacac   8940
```

```
agcccctgcc agaaaggagg gacctgtgtg aacatgccaa gcggccccca ctgtctctgt    9000
ccacaacacc tcactggaaa ccactgccag aaaggtgagg agatgtggag gacctgggcg    9060
gggtgctggg ggacaggggc aaccctgggc ctacagaata ggttgctgga tactcggaga    9120
cttggcatgg tcctagactc tcctgagacc actatccctc tttgtcccca gagaagtgct    9180
ttgagcctca gcttctccgg ttttccaca agaatgagat atggtataga actgagcaag     9240
cagctgtggc cagatgccag tgcaagggtc ctgatgccca ctgccagcgg ctggccagcc    9300
agggtgagca gatggttggg aacgggccag ggaggagcgt caggaagaca ggctggcagg    9360
aggccgggtg gtgtgccagg aaggagagct ctctggggggg gtctttaggc ccaggggtgg   9420
ctcactgcgt tccctcccca agcctgccgc accaacccgt gcctccatgg gggtcgctgc    9480
ctagaggtgg agggccaccg cctgtgccac tgcccggtgg gctacaccgg acccttctgc    9540
gacgtgggtg agtgagggtc tggggcaagc agaaggccag cccccaggtg ggacgggctt    9600
gccaggaagg aggagggaga gtgcggaaag cagatgagag ggaggcagga gagcccagcc    9660
ttggctgccc agggagcccc ctttctcctc agacaccaag gcaagctgct atgatggccg    9720
cgggctcagc taccgcggcc tggccaggac cacgctctcg ggtgcgccct gtcagccgtg    9780
ggcctcggag gccacctacc ggaacgtgac tgccgagcaa gcgcggaact ggggactggg    9840
cggccacgcc ttctgccggt gcgccgcgtg gggctgggtg accctccgc cccagggctc     9900
cgggctcccg gcgctctaac ggcgcccgt cgtgtggcta caggaacccg gacaacgaca    9960
tccgcccgtg gtgcttcgtg ctgaaccgcg accggctgag ctgggagtac tgcgacctgg    10020
cacagtgcca gaccccaacc caggcggcgc ctccgacccc ggtgtcccct aggcttcatg    10080
tcccactcat gcccgcgcag ccggcaccgc cgaagcctca gcccacgacc cggaccccgc    10140
ctcagtccca gaccccggga ggttaggaag tggggggggg aaggaggagc cgagagggcg    10200
ccgggcgagc tagattccgg ccagccggcc gcgggctctc cgtcctcagc ccctgctcct    10260
ccacagcctt gccggcgaag cgggagcagc cgccttccct gaccaggaac ggcccactga    10320
gctgcgggca gcggctccgc aagagtctgt cttcgatgac ccgcgtcgtt ggcgggctgg    10380
tggcgctacg cggggcgcac ccctacatcg ccgcgctgta ctgggccac agtttctgcg      10440
ccggcagcct catcgccccc tgctgggtgc tgacggccgc tcactgcctg caggaccggc    10500
gagtacccgc ccgcccagag ccgcccccagg ggccgcggct cctccgtctc ccagcgcagc   10560
ttccacgctg cacccgaacc cgtgccctac cttctcccgc ccacccttc tttccacgcc     10620
cctccggagc tcccggggag gaagctggaa cacgggattg gggttcggga gcaggggct     10680
tccccagaac gcttgtggcc aggtctgaga gcgctgcctc tcccctaccc ccccgcagg     10740
cccgcacccg aggatctgac ggtggtgctc ggccaggaac gccgtaacca cagctgtgag    10800
ccgtgccaga cgttggccgt gcgctcctac cgcttgcacg aggccttctc gcccgtcagc    10860
taccagcacg acctgggtgc gtgggggcgc cccgcgggga cgggaagaga gcttggggcc    10920
ccggcgtccc cgcctcacgc tcctctccgc ccgggttagc tctgttgcgc cttcaggagg    10980
atgcggacgg cagctgcgcg ctcctgtcgc cttacgttca gccggtgtgc ctgccaagcg    11040
gcgccgcgcg accctccgag accacgctct gccaggtggc cggctgggc caccagttcg     11100
agggtaggca caactgctag ggcagggt agggaggag accttttgatc actgggttag     11160
gcggaagaag cccgcgactt tggtatcgtt ccgggtgcct acagaatggg tggcgctgac    11220
ctgatgggtt gtgagaatgt gtaggtgaat cccaggtaga atcccagggc ctgggattca    11280
ctgctgggat ccccaaatct cctggggata cagggagaat cgaacttgct cttggttccc    11340
```

-continued

```
tctgggcgcc gggctgcaaa ggccaactag gacgctggcc ccgcgctccg ggctagtgtg    11400
ggagccaggt tctgcgactc tggatgggtg gtggggagg ggtttctgtt tccgctccgc    11460
ccattcaaat cctggctttt ctctggacct cagcctcctt gcctatgaaa ttgaattaat    11520
ggcacctcct cccttcggg cttgctgcga gagaggaagg gcatgagtgg gtttacaagc    11580
gcctggagca gctttgtcca tcgtccgggc ggcaagcgtt gtcagatggg gtgtgaagaa    11640
ggcgctctgt gttcgcaggg gcggaggaat atgccagctt cctgcaggag gcgcaggtac    11700
cgttcctctc cctggagcgc tgctcagccc cggacgtgca cggatcctcc atcctcccg    11760
gcatgctctg cgcagggttc ctcgagggcg gcaccgatgc gtgccaggtg agctcttagc    11820
ccggttggcg cccttccccg aggccgtcag gcacaaatct caggtccaca gcgctgagct    11880
gcgtgtttcc gacccagggt gattccgag gcccgctggt gtgtgaggac caagctgcag    11940
agcgccggct caccctgcaa ggcatcatca gctggggatc gggctgtggt gaccgcaaca    12000
agccaggcgt ctacaccgat gtggcctact acctggcctg gatccgggag cacaccgttt    12060
cctgactaac caggctttat ccttccctcc ttgtgtgctc cttgggatgg gacgatgaat    12120
gtggcatgct gggtcacagt gaagctagtg ccccgacact gggggcacag aaactc        12176
```

```
<210> SEQ ID NO 18
<211> LENGTH: 7444
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: Mouse Sequence
<220> FEATURE:
<221> NAME/KEY: misc_feature
<222> LOCATION: (20)..(3893)
<223> OTHER INFORMATION: Human Sequence
<220> FEATURE:
<221> NAME/KEY: misc_feature
<222> LOCATION: (20)..(22)
<223> OTHER INFORMATION: Start Codon
<220> FEATURE:
<221> NAME/KEY: misc_feature
<222> LOCATION: (3742)..(3812)
<223> OTHER INFORMATION: Exon 4
<220> FEATURE:
<221> NAME/KEY: misc_feature
<222> LOCATION: (3894)..(3971)
<223> OTHER INFORMATION: Deleted Neo Self-Deleting Cassette
<220> FEATURE:
<221> NAME/KEY: misc_feature
<222> LOCATION: (3894)..(3899)
<223> OTHER INFORMATION: XhoI
<220> FEATURE:
<221> NAME/KEY: misc_feature
<222> LOCATION: (3900)..(3933)
<223> OTHER INFORMATION: LoxP
<220> FEATURE:
<221> NAME/KEY: misc_feature
<222> LOCATION: (3940)..(3965)
<223> OTHER INFORMATION: I_Ceu
<220> FEATURE:
<221> NAME/KEY: misc_feature
<222> LOCATION: (3966)..(3971)
<223> OTHER INFORMATION: NheI
<220> FEATURE:
<221> NAME/KEY: misc_feature
<222> LOCATION: (3972)..(7333)
<223> OTHER INFORMATION: Human Sequence
<220> FEATURE:
<221> NAME/KEY: misc_feature
<222> LOCATION: (4192)..(4302)
```

```
<223> OTHER INFORMATION: Exon 5
<220> FEATURE:
<221> NAME/KEY: misc_feature
<222> LOCATION: (4440)..(4571)
<223> OTHER INFORMATION: Exon 6
<220> FEATURE:
<221> NAME/KEY: misc_feature
<222> LOCATION: (4711)..(4815)
<223> OTHER INFORMATION: Exon 7
<220> FEATURE:
<221> NAME/KEY: misc_feature
<222> LOCATION: (7331)..(7333)
<223> OTHER INFORMATION: Stop Codon
<220> FEATURE:
<221> NAME/KEY: misc_feature
<222> LOCATION: (7334)..(7444)
<223> OTHER INFORMATION: Mouse Sequence

<400> SEQUENCE: 18
```

| | | | | | |
|---|---|---|---|---|---|
| ggggccatcg | gcagacgcca | tgagggctct | gctgctcctg | gggttcctgc | tggtgagctt | 60 |
| ggagtcaaca | ctttcggtga | gtgctgtggg | aaccaggatt | gtcccaggat | tgttctgggg | 120 |
| ggtcgctatc | acagccatga | gccatggcct | ctgctcatga | cctgtgggtc | caggtgacta | 180 |
| ggaggcctat | gtggaaaggt | gaggccagcc | cggaaggccc | aggcagagga | gacagacaac | 240 |
| cagactgggt | ggatacaagg | gcacagcctg | catttctggg | ggagatgggc | cttaagaaga | 300 |
| caacgggggg | aggtagaaag | gtttgggtc | ttgggaagaa | atctctgcat | ttctgggctg | 360 |
| tgagaggaag | ctgcagacta | gcaacagatc | ggtggcaggc | tatgacttat | agtcagttcc | 420 |
| ctgccttctt | ctctcccttg | tagattccac | cttgggaagc | cccaaggag | cataagtaca | 480 |
| aagctgaaga | gcacacagtc | ggtaagtggc | ctggctcctc | ctcccgggaa | cccttgggtg | 540 |
| gggatgtgta | tggtgcagtg | tgtgcagtct | cagggcagtc | tagtctagtg | cctacctggt | 600 |
| gctaggtctt | atgcccatgg | gcactagagt | gatcgtgagc | tgtgtgatcc | ttgagggcag | 660 |
| ggtatgggct | gtgtctaagt | gcccacgagc | ctggctcgga | gcaggtgctt | gagatatgtg | 720 |
| ctgctggcgc | catcacacct | gggctcctgc | cagccttcct | cagtttcccc | agcttctccc | 780 |
| cttcttttcc | tttccccagt | acgtctcatg | gcatcattc | atgccacaca | gaggccaggg | 840 |
| ccttcaatgg | gcaaggaagg | atcaagagct | tgtctctggc | atctgaatgc | ctctgaagcc | 900 |
| cagctttatc | acttatgagc | tgggtgactc | tgggcgaggg | atttgagttc | tccaagcttc | 960 |
| aatttcccct | tctgtgaaac | caggttgata | acagtaaacc | tcttagggtt | gttgagaagg | 1020 |
| gaaacccatg | tgaggtattc | agcccatcac | ctggtgcatg | gaaatgcttt | acaaatatta | 1080 |
| gcttttatta | tgaaactacc | ttttagatga | agggtacctg | ccatttcccc | cttcctcaag | 1140 |
| ctctgccata | gctccccatt | gctttcattc | ttccagacac | taaattaccT | acatgccagg | 1200 |
| catggtggct | catgcctgta | atcccagcac | tttgggaggc | caaggtcggt | ggatcatgag | 1260 |
| gtcaggagtt | cgagaccagc | ctggccaaca | tggtgaaatg | ctgtctctac | taaaagtaca | 1320 |
| aaaattagcc | aggcatggtg | gcatgcgcca | gtagtcccag | ctactcggga | ggctgaggca | 1380 |
| gaagaattgc | ttgaacctgg | gaggtgaagg | ttgcagtgaa | cgaagatcac | accattgcac | 1440 |
| tccagcttgg | gcaacacagc | aagactccgt | ctcaaaaaaa | aaaaaaaaat | ttacctagag | 1500 |
| tgtggcacat | agcagggcct | gtgaaccaga | tggaccttac | cctggtgggc | ctgacttggt | 1560 |
| ggggttgagt | ctctaagcat | ggcgttgagg | cccagcacat | tccaaccctg | gactccctca | 1620 |
| gcctcctctc | ttcaccccac | acccaaaagt | ttctcctctc | tcttgcctta | cccaaacttg | 1680 |
| gtgccctatc | cttgcctaat | cccctgccta | aggtccccct | cctctctgtc | cgtccatccc | 1740 |
| atctgcatct | ttttttttt | ttgagatgga | gtctcgctct | gtccctagg | ctagagtgca | 1800 |

```
atggcgcgat cttggctcat tgcaacctcc gcctcctggg ttcaagcgat tctctgcctc    1860
agcctcccga gttgctggga ttacaggcac acaaacttcat gctcagctaa tttttgtatt    1920
ttttagtaga gacagggttt caccatgttg gccaggctgg tctcgaactc ctgccctcag    1980
gtggtccgcc cacctagcc tcccaaagtg ctgggattac aggcgtgagc caccgcgcct     2040
ggcccccatt tgcatcttaa aggtccatct cagatccatt tccatttact gtcctagttc    2100
tggtttggtc cttggcaagt gcactttgcc ttgaacaaaa tagtggcaaa agcttattga    2160
gcaggtactt tgtgccagac actgctcagc atttcatggc attatctcat gaagccccac    2220
gacaattcct ctgaagaaga cacaggcaat tctcattatt cgcgatggtt atgttctata    2280
aaatcacagt gaacattgaa ctagcaaaca gtattaggtt cctgtgagcc tctggtcaca    2340
acattttcat caaccaacag catataatct ggttttatgt atgattctgt ttaaagacat    2400
tttatttagt atatgtgttg ctgattcatc aatgctaagc tgatggcact atagcacaca    2460
cctgaatcaa gtgtctaaca cacgctttct ccctaaggta gccttcttgt gcttaggaac    2520
tacacagctc ttcagcagga ggctcagagg ccatttccaa aagccaaatc cccagcaaaa    2580
gcacaaagtg tgaaaaacgt tgcactaagt agactgagaa ggacactcat tcaataggag    2640
agctgaaaca agcagcagca gcgtgacgcc ttgttgaacc ttaactggga atgtgcaaat    2700
ttttcactgc tctgtgcatg cccacaaatg gccatgaaaa catttcaagt attgacttgg    2760
gagttacaaa taaaattcag caagtaggca cattctcaat gtagaaccag agaagaatga    2820
ggatcaactg tactattatt actgccgttt tacagataag gaaaccaagg ctcagatcag    2880
agtggttaac agtgacttca acattcaaca agtattatta agtgcctact tgtgtggcaag   2940
tgctcttcct ggccttggga ctgaagactt acccaaggtc acacagctag caggttgtgg    3000
agtcaggagt ctactccagc tatctgactc ctgaacccaa gttttttttt ttttctttaa    3060
gatggagtct cactctgtca cccaggctgg agtgcagtgg cgcgatctcg gctcactgca    3120
agctccgcct cccgggttca caccattctc ctgcctcggc ctcccgagta gctgggacta    3180
caggcacctg ccaccacccc cagctaattt ttttgtattt ttagtagaga gggggtttca    3240
ctgtattagc caggatggtc ttgatctcct gacctcgtga tctgcccgcc ttggcctccc    3300
aaagtgctgg gattacaggc ttgagccacc gcgcccggcc ctgaacccaa cttttagagc    3360
agaaagtgtt tcaatgcac agcgaccttt tgagggtct gtccttttcc tgaccagacc      3420
ctgagggaca gtgcctgagc agttgagtac aggggaagtc ctcagagagt gtgttgtccc    3480
tgcagttctc actgtcaccg gggagccctg ccacttcccc ttccagtacc accggcagct    3540
gtaccacaaa tgtacccaca agggccggcc aggccctcag ccctggtaag actacgcaga    3600
ggagttggag caggggcctg ggagacatgt accctgcctg tccttctgtc caaggaactc    3660
tgcttggaga gagggactg tgatagggca gggtgggcca ggcccctggg tagagcaggg     3720
aagccttgtc tctttctaca ggtgtgctac cacccccaac tttgatcagg accagcgatg    3780
gggatactgt ttggagccca agaaagtgaa aggtgctaca cacagcctct ggggtggcct    3840
ggggctctct cctcccgcct cattactctc ctggtatcac cagacccac acactcgaga     3900
taacttcgta taatgtatgc tatacgaagt tatgctaggt aactataacg gtcctaaggt    3960
agcgagctag ccctgggatt ctggacccag ccccttctct ccctccacaa tacccttttgg   4020
aagtccagag ggagagttct gggaaggagt ggtcccattt tgcaggtggg taaaccaagc    4080
ttggaaactt ggagtagcaa ggtcacaagg caagtaggtt caagaagggc cttggccccc    4140
```

| | | | | |
|---|---|---|---|---|
| agctgtgtga | ctcagctccc | tgctcttcct | tccaccatgt | ccatctctca gaccactgca | 4200 |
| gcaaacacag | cccctgccag | aaaggaggga | cctgtgtgaa | catgccaagc ggcccccact | 4260 |
| gtctctgtcc | acaacacctc | actggaaacc | actgccagaa | aggtgaggag atgtggagga | 4320 |
| cctgggcggg | gtgctggggg | acaggggcaa | ccctgggcct | acagaatagg ttgctggata | 4380 |
| ctcggagact | tggcatggtc | ctagactctc | ctgagaccac | tatccctctt tgtccccaga | 4440 |
| gaagtgcttt | gagcctcagc | ttctccggtt | tttccacaag | aatgagatat ggtatagaac | 4500 |
| tgagcaagca | gctgtggcca | gatgccagtg | caagggtcct | gatgcccact gccagcggct | 4560 |
| ggccagccag | ggtgagcaga | tggttgggaa | cgggccaggg | aggagcgtca ggaagacagg | 4620 |
| ctggcaggag | gccgggtggt | gtgccaggaa | ggagagctct | ctggggggt ctttaggccc | 4680 |
| aggggtggct | cactgcgttc | cctccccaag | cctgccgcac | caacccgtgc ctccatgggg | 4740 |
| gtcgctgcct | agaggtggag | ggccaccgcc | tgtgccactg | cccggtgggc tacaccggac | 4800 |
| ccttctgcga | cgtgggtgag | tgagggtctg | gggcaagcag | aaggccagcc ccaggtggg | 4860 |
| acgggcttgc | caggaaggag | gagggagagt | gcggaaagca | gatgagaggg aggcaggaga | 4920 |
| gcccagcctt | ggctgcccag | ggagccccct | ttctcctcag | acaccaaggc aagctgctat | 4980 |
| gatggccgcg | ggctcagcta | ccgcggcctg | gccaggacca | cgctctcggg tgcgccctgt | 5040 |
| cagccgtggg | cctcggaggc | cacctaccgg | aacgtgactg | ccagcaagc gcggaactgg | 5100 |
| ggactgggcg | ccacgccctt | ctgccggtgc | gccgcgtggg | gctgggtgac ccctccgccc | 5160 |
| cagggctccg | ggctcccggc | gctctaacgg | cgcccgtcg | tgtggctaca ggaacccgga | 5220 |
| caacgacatc | cgcccgtggt | gcttcgtgct | gaaccgcgac | cggctgagct gggagtactg | 5280 |
| cgacctggca | cagtgccaga | ccccaaccca | ggcggcgcct | ccgacccgg tgtcccctag | 5340 |
| gcttcatgtc | ccactcatgc | ccgcgcagcc | ggcaccgccg | aagcctcagc ccacgacccg | 5400 |
| gaccccgcct | cagtcccaga | ccccgggagg | ttaggaagtg | gggggggaa ggaggagccg | 5460 |
| agagggcgcc | gggcgagcta | gattccggcc | agccggccgc | gggctctccg tcctcagccc | 5520 |
| ctgctcctcc | acagccttgc | cggcgaagcg | ggagcagccg | ccttccctga ccaggaacgg | 5580 |
| cccactgagc | tgcgggcagc | ggctccgcaa | gagtctgtct | tcgatgaccc gcgtcgttgg | 5640 |
| cgggctggtg | gcgctacgcg | gggcgcaccc | ctacatcgcc | gcgctgtact ggggccacag | 5700 |
| tttctgcgcc | ggcagcctca | tcgcccctg | ctgggtgctg | acggccgctc actgcctgca | 5760 |
| ggaccggcga | gtaccgcccc | gcccagagcc | gccccagggg | ccgcggctcc tccgtctccc | 5820 |
| agcgcagctt | ccacgctgca | cccgaacccg | tgccctacct | tctcccgccc cacccttctt | 5880 |
| tccacgcccc | tccggagctc | ccggggagga | agctggaaca | cgggattggg gttcgggagc | 5940 |
| agggggcttc | cccagaacgc | ttgtggccag | gtctgagagc | gctgcctctc ccctaccccc | 6000 |
| cccgcaggcc | cgcacccgag | gatctgacgg | tggtgctcgg | ccaggaacgc cgtaaccaca | 6060 |
| gctgtgagcc | gtgccagacg | ttggccgtgc | gctcctaccg | cttgcacgag gccttctcgc | 6120 |
| ccgtcagcta | ccagcacgac | ctgggtgcgt | ggggcgcccc | cgcggggacg ggaagagagc | 6180 |
| ttggggcccc | ggcgtccccg | cctcacgctc | ctctccgccc | gggttagctc tgttgcgcct | 6240 |
| tcaggaggat | gcgacggca | gctgcgcgct | cctgtcgcct | tacgttcagc cggtgtgcct | 6300 |
| gccaagcggc | gccgcgcgac | cctccgagac | cacgctctgc | caggtggccg gctggggcca | 6360 |
| ccagttcgag | ggtaggcaca | actgctaggg | gcagggtag | ggaggagac ctttgatcac | 6420 |
| tgggttaggg | ggaagaagcc | cgcgactttg | gtatcgttcc | gggtgcctac agaatgggtg | 6480 |
| gcgctgacct | gatgggttgt | gagaatgtgt | aggtgaatcc | caggtagaat cccagggcct | 6540 |

```
gggattcact gctgggatcc ccaaatctcc tggggataca gggagaatcg aacttgctct    6600
tggttccctc tgggcgccgg gctgcaaagg ccaactagga cgctggcccc gcgctccggg    6660
ctagtgtggg agccaggttc tgcgactctg gatggtggt gggggagggg tttctgtttc     6720
cgctccgccc attcaaatcc tggcttttct ctggacctca gcctccttgc ctatgaaatt    6780
gaattaatgg cacctcctcc ccttcgggct tgctgcgaga gaggaagggc atgagtgggt    6840
ttacaagcgc ctggagcagc tttgtccatc gtccgggcgg caagcgttgt cagatggggt    6900
gtgaagaagg cgctctgtgt tcgcaggggc ggaggaatat gccagcttcc tgcaggaggc    6960
gcaggtaccg ttcctctccc tggagcgctg ctcagccccg gacgtgcacg gatcctccat    7020
cctccccggc atgctctgcg cagggttcct cgagggcggc accgatgcgt gccaggtgag    7080
ctcttagccc ggttggcgcc cttccccgag gccgtcaggc acaaatctca ggtccacagc    7140
gctgagctgc gtgtttccga cccagggtga ttccggaggc ccgctggtgt gtgaggacca    7200
agctgcagag cgccggctca ccctgcaagg catcatcagc tggggatcgg gctgtggtga    7260
ccgcaacaag ccaggcgtct acaccgatgt ggcctactac ctggcctgga tccgggagca    7320
caccgtttcc tgactaacca ggctttatcc ttccctcctt gtgtgctcct tgggatggga    7380
cgatgaatgt ggcatgctgg gtcacagtga agctagtgcc ccgacactgg gggcacagaa    7440
actc                                                                7444

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
tcggtggcag gctatgactt atag                                              24

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
cagttccctg ccttcttctc tccc                                              24

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21
ggcttcccaa ggtggaatct ac                                                22

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
```
aagggcatga gtgggtttac aag                                              23

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
cgcctggagc agctttgtcc atc                                              23

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
acacagagcg ccttcttcac a                                                21

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
gttcctgcct tctctctcct a                                                21

<210> SEQ ID NO 26
<211> LENGTH: 25
<212> TYPE: DNA
<213> ORGANISM: Artificial Sequence
<220> FEATURE:
<223> OTHER INFORMATION: Synthetic

<400> SEQUENCE: 26
taggctccac catggaaaga ctcca                                            25

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
cccatcaggt gcgtcctta                                                   19

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tcgctgctcc aactctaacg                                                  20

<210> SEQ ID NO 29
<211> LENGTH: 23
<212> TYPE: DNA
<213> ORGANISM: Artificial Sequence

```
<220> FEATURE:
<223> OTHER INFORMATION: Synthetic

<400> SEQUENCE: 29
acgccattct ccctgggatg ctt                                             23

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30
atcggtgcct ccctccaaga ag                                              22

<210> SEQ ID NO 31
<211> LENGTH: 3874
<212> TYPE: DNA
<213> ORGANISM: Homo sapiens

<400> SEQUENCE: 31
atgagggctc tgctgctcct ggggttcctg ctggtgagct ggagtcaac actttcggtg      60 agtgctgtgg gaaccaggat tgtcccagga ttgttctggg gggtcgctat cacagccatg    120
agccatggcc tctgctcatg acctgtgggt ccaggtgact aggaggccta tgtgaaagg    180 tgaggccagc ccggaaggcc caggcagagg agacagacaa ccagactggg tggatacaag   240
ggcacagcct gcatttctgg gggagatggg ccttaagaag acaacggggg gaggtagaaa   300
gggtttgggt cttgggaaga aatctctgca tttctgggct gtgagaggaa gctgcagact   360
agcaacagat cggtggcagg ctatgactta tagtcagttc cctgccttct tctctcccct   420
gtagattcca ccttgggaag cccccaagga gcataagtac aaagctgaag agcacacagt   480
cggtaagtgg cctggctcct cctcccggga acccttgggt ggggatgtgt atggtgcagt   540
gtgtgcagtc tcagggcagt ctagtctagt gcctacctgg tgctaggtct tatgcccatg   600
ggcactagag tgatcgtgag ctgtgtgatc cttgagggca gggtatgggc tgtgtctaag   660
tgcccacgag cctggctcgg agcaggtgct tgagatatgt gctgctggcg ccatcacacc   720
tgggctcctg ccagccttcc tcagtttccc cagcttctcc ccttcttttc ctttccccag   780
tacgtctcat gggcatcatt catgccacac agaggccagg gccttcaatg gcaaggaag    840 gatcaagagc ttgtctctgg catctgaatg cctctgaagc ccagctttat cacttatgag   900
ctgggtgact ctgggcgagg gatttgagtt ctccaagctt caatttcccc ttctgtgaaa   960
ccaggttgat aacagtaaac ctcttagggt tgttgagaag ggaaacccat gtgaggtatt  1020
cagcccatca cctggtgcat ggaaatgctt tacaaatatt agcttttatt atgaaactac  1080
cttttagatg aagggtacct gccatttccc ccttcctcaa gctctgccat agctccccat  1140
tgctttcatt cttccagaca ctaaattacc tacatgccag gcatggtggc tcatgcctgt  1200
aatcccagca ctttgggagg ccaaggtcgg tggatcatga ggtcaggagt tcgagaccag  1260
cctggccaac atggtgaaat gctgtctcta ctaaaagtac aaaaattagc caggcatggt  1320
ggcatgcgcc agtagtccca gctactcggg aggctgaggc agaagaattg cttgaacctg  1380
ggaggtgaag gttgcagtga acgaagatca caccattgca ctccagcttg gcaacacag   1440 caagactccg tctcaaaaaa aaaaaaaaaa tttacctaga gtgtggcaca tagcagggcc  1500
tgtgaaccag atggacctta ccctggtggg cctgacttgg tggggttgag tctctaagca  1560
```

```
tggcgttgag gcccagcaca ttccaaccct ggactccctc agcctcctct cttcacccca    1620
cacccaaaag tttctcctct ctcttgcctt acccaaactt ggtgccctat ccttgcctaa    1680
tcccctgcct aaggtccccc tcctctctgt ccgtccatcc catctgcatc ttttttttt    1740
tttgagatgg agtctcgctc tgtccccctag gctagagtgc aatggcgcga tcttggctca   1800
ttgcaacctc cgcctcctgg gttcaagcga ttctctgcct cagcctcccg agttgctggg    1860
attacaggca cacaacttca tgctcagcta attttttgtat ttttttagtag agacagggtt  1920
tcaccatgtt ggccaggctg gtctcgaact cctgcccctca ggtggtccgc ccaccttagc   1980
ctcccaaagt gctgggatta caggcgtgag ccaccgcgcc tggcccccat ttgcatctta    2040
aaggtccatc tcagatccat ttccatttac tgtcctagtt ctggtttggt ccttggcaag    2100
tgcactttgc cttgaacaaa atagtggcaa aagcttattg agcaggtact ttgtgccaga    2160
cactgctcag catttcatgg cattatctca tgaagcccca cgacaattcc tctgaagaag    2220
acacaggcaa ttctcattat tcgcgatggt tatgttctat aaaatcacag tgaacattga    2280
actagcaaac agtattaggt tcctgtgagc ctctggtcac aacattttca tcaaccaaca    2340
gcatataatc tggttttatg tatgattctg tttaaagaca ttttatttag tatatgtgtt    2400
gctgattcat caatgctaag ctgatggcac tatagcacac acctgaatca agtgtctaac    2460
acacgctttc tccctaaggt agccttcttg tgcttaggaa ctacacagct cttcagcagg    2520
aggctcagag gccatttcca aaagccaaat ccccagcaaa agcacaaagt gtgaaaaacg    2580
ttgcactaag tagactgaga aggacactca ttcaatagga gagctgaaac aagcagcagc    2640
agcgtgacgc cttgttgaac cttaactggg aatgtgcaaa ttttttcactg ctctgtgcat   2700
gcccacaaat ggccatgaaa acatttcaag tattgacttg ggagttacaa ataaaattca    2760
gcaagtaggc acattctcaa tgtagaacca gagaagaatg aggatcaact gtactattat    2820
tactgccgtt ttacagataa ggaaaccaag gctcagatca gagtggttaa cagtgacttc    2880
aacattcaac aagtattatt aagtgcctac tttgtggcaa gtgctcttcc tggccttggg    2940
actgaagact acccaaggt cacacagcta gcaggttgtg gagtcaggag tctactccag     3000
ctatctgact cctgaaccca agttttttt ttttctttta agatggagtc tcactctgtc     3060
acccaggctg gagtgcagtg gcgcgatctc ggctcactgc aagctccgcc tcccgggttc    3120
acaccattct cctgcctcgg cctcccgagt agctgggact acaggcacct gccaccaccc    3180
ccagctaatt ttttttgtatt tttagtagag aggggggtttc actgtattag ccaggatggt  3240
cttgatctcc tgacctcgtg atctgcccgc cttggcctcc caaagtgctg ggattacagg    3300
cttgagccac cgcgcccggc cctgaaccca acttttagag cagaaagtgt tttcaatgca    3360
cagcgacctt tttgagggtc tgtccttttc ctgaccagac cctgagggac agtgcctgag   3420
cagttgagta caggggaagt cctcagagag tgtgttgtcc ctgcagttct cactgtcacc    3480
ggggagccct gccacttccc cttccagtac caccggcagc tgtaccacaa atgtacccac    3540
aagggccggc caggccctca gccctggtaa gactacgcag aggagttgga gcaggggcct    3600
gggagacatg taccctgcct gtccttctgt ccaaggaact ctgcttggag agggggact     3660
gtgatagggc agggtgggcc aggccccctgg gtagagcagg gaagccttgt ctctttctac   3720
aggtgtgcta ccaccccaa cttttgatcag gaccagcgat ggggatactg tttggagccc    3780
aagaaagtga aaggtgctac acacagcctc tggggtggcc tggggctctc tcctcccgcc    3840
tcattactct cctggtatca ccagaccca caca                                 3874
```

<210> SEQ ID NO 32
<211> LENGTH: 3362
<212> TYPE: DNA
<213> ORGANISM: Homo sapiens

<400> SEQUENCE: 32

| | | | | | | |
|---|---|---|---|---|---|---|
| cctgggattc | tggacccagc | cccttctctc | cctccacaat | accctttgga | agtccagagg | 60 |
| gagagttctg | ggaaggagtg | gtcccatttt | gcaggtgggt | aaaccaagct | tggaaacttg | 120 |
| gagtagcaag | gtcacaaggc | aagtaggttc | aagaagggcc | ttggccccca | gctgtgtgac | 180 |
| tcagctccct | gctcttcctt | ccaccatgtc | catctctcag | accactgcag | caaacacagc | 240 |
| ccctgccaga | aaggagggac | ctgtgtgaac | atgccaagcg | gcccccactg | tctctgtcca | 300 |
| caacacctca | ctggaaacca | ctgccagaaa | ggtgaggaga | tgtggaggac | ctgggcgggg | 360 |
| tgctggggga | caggggcaac | cctgggccta | cagaataggt | tgctggatac | tcggagactt | 420 |
| ggcatggtcc | tagactctcc | tgagaccact | atccctcttt | gtccccagag | aagtgctttg | 480 |
| agcctcagct | tctccggttt | ttccacaaga | atgagatatg | gtatagaact | gagcaagcag | 540 |
| ctgtggccag | atgccagtgc | aagggtcctg | atgcccactg | ccagcggctg | gccagccagg | 600 |
| gtgagcagat | ggttgggaac | gggccaggga | ggagcgtcag | gaagacaggc | tggcaggagg | 660 |
| ccgggtggtg | tgccaggaag | gagagctctc | tgggggggtc | tttaggccca | ggggtggctc | 720 |
| actgcgttcc | ctccccaagc | ctgccgcacc | aacccgtgcc | tccatggggg | tcgctgccta | 780 |
| gaggtggagg | gccaccgcct | gtgccactgc | ccggtgggct | acaccggacc | cttctgcgac | 840 |
| gtgggtgagt | gagggtctgg | ggcaagcaga | aggccagccc | ccaggtggga | cgggcttgcc | 900 |
| aggaaggagg | agggagagtg | cggaaagcag | atgagaggga | ggcaggagag | cccagccttg | 960 |
| gctgcccagg | gagcccccctt | tctcctcaga | caccaaggca | agctgctatg | atggccgcgg | 1020 |
| gctcagctac | cgcggcctgg | ccaggaccac | gctctcgggt | gcgccctgtc | agccgtgggc | 1080 |
| ctcggaggcc | acctaccgga | acgtgactgc | cgagcaagcg | cggaactggg | gactgggcgg | 1140 |
| ccacgccttc | tgccggtgcg | ccgcgtgggg | ctgggtgacc | cctccgcccc | agggctccgg | 1200 |
| gctcccggcg | ctctaacggc | gccccgtcgt | gtggctacag | gaacccggac | aacgacatcc | 1260 |
| gcccgtggtg | cttcgtgctg | aaccgcgacc | ggctgagctg | ggagtactgc | gacctggcac | 1320 |
| agtgccagac | cccaacccag | gcggcgcctc | cgaccccggt | gtcccctagg | cttcatgtcc | 1380 |
| cactcatgcc | cgcgcagccg | gcaccgccga | agcctcagcc | cacgacccgg | accccgcctc | 1440 |
| agtcccagac | cccggggaggt | taggaagtgg | gggggggaag | gaggagccga | gagggcgccg | 1500 |
| ggcgagctag | attccggcca | gccggccgcg | ggctctccgt | cctcagcccc | tgctcctcca | 1560 |
| cagccttgcc | ggcgaagcgg | gagcagccgc | cttccctgac | caggaacggc | ccactgagct | 1620 |
| gcggcagcgc | gctccgcaag | agtctgtctt | cgatgacccg | cgtcgttggc | gggctggtgg | 1680 |
| cgctacgcgg | ggcgcacccc | tacatcgccg | cgctgtactg | gggccacagt | ttctgcgccg | 1740 |
| gcagcctcat | cgcccctgc | tgggtgctga | cggccgctca | ctgcctgcag | gaccggcgag | 1800 |
| taccgccccg | cccagagccg | ccccaggggc | gcggctcct | ccgtctccca | gcgcagcttc | 1860 |
| cacgctgcac | ccgaacccgt | gccctacctt | ctcccgcccc | acccttcttt | ccacgcccct | 1920 |
| ccggagctcc | cggggaggaa | gctggaacac | gggattgggg | ttcgggagca | ggggcttcc | 1980 |
| ccagaacgct | tgtggccagg | tctgagagcg | ctgcctctcc | cctaccccc | ccgcaggccc | 2040 |
| gcacccgagg | atctgacggt | ggtgctcggc | caggaacgcc | gtaaccacag | ctgtgagccg | 2100 |
| tgccagacgt | tggccgtgcg | ctcctaccgc | ttgcacgagg | ccttctcgcc | cgtcagctac | 2160 |

| | |
|---|---:|
| cagcacgacc tgggtgcgtg ggggcgcccc gcggggacgg gaagagagct tggggccccg | 2220 |
| gcgtccccgc ctcacgctcc tctccgcccg ggttagctct gttgcgcctt caggaggatg | 2280 |
| cggacggcag ctgcgcgctc ctgtcgcctt acgttcagcc ggtgtgcctg ccaagcggcg | 2340 |
| ccgcgcgacc ctccgagacc acgtctgcc aggtggccgg ctggggccac cagttcgagg | 2400 |
| gtaggcacaa ctgctagggg caggggtagg ggaggagacc tttgatcact gggttaggcg | 2460 |
| gaagaagccc gcgactttgg tatcgttccg ggtgcctaca gaatgggtgg cgctgacctg | 2520 |
| atgggttgtg agaatgtgta ggtgaatccc aggtagaatc ccagggcctg ggattcactg | 2580 |
| ctgggatccc caaatctcct ggggatacag ggagaatcga acttgctctt ggttccctct | 2640 |
| gggcgccggg ctgcaaaggc caactaggac gctggccccg cgctccgggc tagtgtggga | 2700 |
| gccaggttct cgcgactctgg atgggtggtg ggggaggggt ttctgttccc gctccgccca | 2760 |
| ttcaaatcct ggcttttctc tggacctcag cctccttgcc tatgaaattg aattaatggc | 2820 |
| acctcctccc cttcgggctt gctgcgagag aggaagggca tgagtgggtt tacaagcgcc | 2880 |
| tggagcagct ttgtccatcg tccgggcggc aagcgttgtc agatgggtg tgaagaaggc | 2940 |
| gctctgtgtt cgcaggggcg gaggaatatg ccagcttcct gcaggaggcg caggtaccgt | 3000 |
| tcctctcct ggagcgctgc tcagcccgg acgtgcacgg atcctccatc ctccccggca | 3060 |
| tgctctgcgc agggttcctc gagggcggca ccgatgcgtg ccaggtgagc tcttagcccg | 3120 |
| gttggcgccc ttccccgagg ccgtcaggca caaatctcag gtccacgcg ctgagctgcg | 3180 |
| tgtttccgac ccagggtgat tccggaggcc cgctggtgtg tgaggaccaa gctgcagagc | 3240 |
| gccggctcac cctgcaaggc atcatcagct ggggatcggg ctgtggtgac cgcaacaagc | 3300 |
| caggcgtcta caccgatgtg gcctactacc tggcctggat ccgggagcac accgtttcct | 3360 |
| ga | 3362 |

<210> SEQ ID NO 33
<211> LENGTH: 1971
<212> TYPE: DNA
<213> ORGANISM: Mus musculus

<400> SEQUENCE: 33

| | |
|---|---:|
| actcctgggc aggcagcggg gccatcggca gacgccatga cggctctgtt gttcctgggg | 60 |
| tctctgctga tgagtctgga tctgacactt tcggctccac catggaaaga ctccaagaaa | 120 |
| tttaaggacg cacctgatgg gcccacagtg ttctcactg tggatgggag gctctgccat | 180 |
| tttcccttc agtaccaccg tcagctacac acaaatgca tccacaaaag gcggccaggc | 240 |
| tcccgcccct ggtgtgctac caccccaac tttgatgaag atcagcaatg gggatactgc | 300 |
| ttggagccca gaaagtgaa agaccattgc agcaaacaca accgtgcca caaggaggg | 360 |
| acatgtatca acacccccaa tgggccacac tgtctctgcc ctgaacacct cactgggaaa | 420 |
| cattgccaga agagaaatg ctttgagcct cagcttctca agttcttcca cgagaatgag | 480 |
| ctatggttta gaacggggcc aggaggtgtg gccaggtgcg agtgcaaagg ttctgaggct | 540 |
| cactgcaagc cggtggccag ccaggcctgc agcatcaatc cgtgccttaa tggggcagc | 600 |
| tgcctcctcg tggaggacca cccactgtgc cgttgcccta caggctacac tggatatttt | 660 |
| tgcgacttgg accttggggc gacctgctat gaaggcaggg ggctcagcta ccggggccag | 720 |
| gctggaacta cgcaatcggg tgcgccatgt cagcggtgga ccgtggaggc cacctaccgg | 780 |
| aacatgactg agaagcaagc gctaagctgg ggcctgggcc accacgcatt tgccggaac | 840 |
| ccagataatg acacacgtcc atggtgcttc gtctggagtg gcgacaggct gagctgggac | 900 |

```
tattgcggcc tggagcagtg ccagacgcca acgtttgcac ctctagttgt ccctgagagt      960
caggaggagt ccccgtccca ggcaccatct ctgtcccatg caccaaatga ctcgaccgat     1020
catcagactt ctctgtccaa gaccaacacg atgggctgcg gacagaggtt ccgcaaggga     1080
ctgtcctcgt tcatgcgcgt ggtgggcgga ctagtggctc tgcctgggtc gcaccccta     1140
atcgctgcac tgtactgggg taacaacttc tgcgcgggca gtctcatcgc ccctgttgg     1200
gtgctgaccg cggctcactg cctgcagaat cggccagcgc cgaggaact gacagtggta     1260
cttggtcaag atcgccacaa ccagagctgc gagtggtgcc agactctggc tgtgcgctcc     1320
taccgccttc acgagggctt ctcctccatc acctaccagc acgacttggc tctgctgcgc     1380
ctgcaggaaa gcaaaaccaa cagttgcgcg atcctgtcac ctcacgttca gcctgtgtgt     1440
ctacccagcg cgcggccccc accctctgag acagtgctct gcgaggtggc cggctggggt     1500
caccagttcg aggggctga agaatactcc accttcctgc aggaggcaca ggttcccttt     1560
atcgccctgg atcgctgctc caactctaac gtgcacggag acgccattct ccctgggatg     1620
ctttgcgctg gcttcttgga gggaggcacc gatgcctgcc agggtgactc cggggccct     1680
ctggtgtgtg aggaaggaac tgcagaacat cagctcaccc tgcgcggagt catcagctgg     1740
ggctccggct gtggtgaccg caacaagccc ggagtctaca cagacgtggc caactacctg     1800
gcttggatcc agaagcatat tgcttcataa ctaaccaggc tttatccttc cctccttgtg     1860
tgctccttgg gatgggacga tgaatgtggc atgctgggtc acagtgaagc tagtgccccg     1920
acactggggg cacagaaact caataaagtg ctttgaaaac gttcctcaga a              1971

<210> SEQ ID NO 34
<211> LENGTH: 2060
<212> TYPE: DNA
<213> ORGANISM: Homo sapiens

<400> SEQUENCE: 34
ctattgatct ggactcctgg ataggcagct ggaccaacgg acggatgcca tgagggctct      60
gctgctcctg gggttcctgc tggtgagctt ggagtcaaca ctttcgattc caccttggga     120
agcccccaag gagcataagt acaaagctga agagcacaca gtcgttctca ctgtcaccgg     180
ggagccctgc cacttcccct tccagtacca ccggcagctg taccacaaat gtacccacaa     240
gggccggcca ggccctcagc cctggtgtgc taccaccccc aactttgatc aggaccagcg     300
atggggatac tgtttggagc ccaagaaagt gaaagaccac tgcagcaaac acagcccctg     360
ccagaaagga gggacctgtg tgaacatgcc aagcggcccc cactgtctct gtccacaaca     420
cctcactgga aaccactgcc agaaagagaa gtgctttgag cctcagcttc tccggttttt     480
ccacaagaat gagatatggt atagaactga gcaagcagct gtggccagat gccagtgcaa     540
gggtcctgat gccgactgcc agcggctggc cagccaggcc tgccgcacca acccgtgcct     600
ccatgggggt cgctgcctag aggtggaggg ccaccgcctg tgccactgcc ggtgggcta     660
caccggagcc ttctgcgacg tggacaccaa ggcaagctgc tatgatggcc gcgggctcag     720
ctaccgcggc ctggcaggac ccacgctctc gggtgcgccc tgtcagccgt gggcctcgga     780
ggccacctac cggaacgtga ctgccgagca agcgcggaac tggggactgg gcggccacgc     840
cttctgccgg aacccggaca acgacatccg cccgtggtgc ttcgtgctga accgcgaccg     900
gctgagctgg gagtactgcg acctggcaca gtgccagacc caacccagg cggcctcc      960
gaccccggtg tccctaggc ttcatgtccc actcatgccc gcgcagccgg caccgccgaa     1020
```

-continued

```
gcctcagccc acgacccgga ccccgcctca gtcccagacc ccgggagcct tgccggcgaa    1080
gcgggagcag ccgccttccc tgaccaggaa cggcccactg agctgcgggc agcggctccg    1140
caagagtctg tcttcgatga cccgcgtcgt tggcgggctg gtggcgctac gcggggcgca    1200
cccctacatc gccgcgctgt actggggcca cagtttctgc gccggcagcc tcatcgcccc    1260
ctgctgggtg ctgacggccg ctcactgcct gcaggaccgg cccgcacccg aggatctgac    1320
ggtggtgctc ggccaggaac gccgtaacca cagctgtgag ccgtgccaga cgttggccgt    1380
gcgctcctac cgcttgcacg aggccttctc gcccgtcagc taccagcacg acctggctct    1440
gttgcgcctt caggaggatg cggacggcag ctgcgcgctc ctgtcgcctt acgttcagcc    1500
ggtgtgcctg ccaagcggcg ccgcgcgacc ctccgagacc acgctctgcc aggtggccgg    1560
ctggggccac cagttcgagg gggcggagga atatgccagc ttcctgcagg aggcgcaggt    1620
accgttcctc tccctggagc gctgctcagc cccggacgtg cacggatcct ccatcctccc    1680
cggcatgctc tgcgcagggt tcctcgaggg cggcaccgat gcgtgccagg gtgattccgg    1740
aggcccgctg gtgtgtgagg accaagctgc agagcgccgg ctcaccctgc aaggcatcat    1800
cagctgggga tcgggctgtg gtgaccgcaa caagccaggc gtctacaccg atgtggccta    1860
ctacctggcc tggatccggg agcacaccgt ttcctgattg ctcagggact catctttccc    1920
tccttggtga ttccgcagtg agagagtggc tggggcatgg aaggcaagat tgtgtcccat    1980
tcccccagtg cggccagctc cgcgccagga tggcgcagga actcaataaa gtgctttgaa    2040
aatgctgaga aaaaaaaaaa                                                2060
```

<210> SEQ ID NO 35
<211> LENGTH: 1391
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(10)
<223> OTHER INFORMATION: 5' NLS
<220> FEATURE:
<221> NAME/KEY: MISC_FEATURE
<222> LOCATION: (1376)..(1391)
<223> OTHER INFORMATION: 3' NLS

<400> SEQUENCE: 35

```
Met Asp Lys Pro Lys Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60

Thr Ala Glu Ala Thr Arg Leu Lys Arg Thr Ala Arg Arg Arg Tyr Thr
65                  70                  75                  80

Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
```

```
            130                 135                 140
Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
    370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
    450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
        515                 520                 525

Asn Glu Leu Thr Lys Val Lys Tyr Val Thr Glu Gly Met Arg Lys Pro
    530                 535                 540

Ala Phe Leu Ser Gly Glu Gln Lys Lys Ala Ile Val Asp Leu Leu Phe
545                 550                 555                 560
```

```
Lys Thr Asn Arg Lys Val Thr Val Lys Gln Leu Lys Glu Asp Tyr Phe
                565                 570                 575
Lys Lys Ile Glu Cys Phe Asp Ser Val Glu Ile Ser Gly Val Glu Asp
                580                 585                 590
Arg Phe Asn Ala Ser Leu Gly Thr Tyr His Asp Leu Leu Lys Ile Ile
                595                 600                 605
Lys Asp Lys Asp Phe Leu Asp Asn Glu Glu Asn Glu Asp Ile Leu Glu
            610                 615                 620
Asp Ile Val Leu Thr Leu Thr Leu Phe Glu Asp Arg Glu Met Ile Glu
625                 630                 635                 640
Glu Arg Leu Lys Thr Tyr Ala His Leu Phe Asp Asp Lys Val Met Lys
                645                 650                 655
Gln Leu Lys Arg Arg Arg Tyr Thr Gly Trp Gly Arg Leu Ser Arg Lys
                660                 665                 670
Leu Ile Asn Gly Ile Arg Asp Lys Gln Ser Gly Lys Thr Ile Leu Asp
            675                 680                 685
Phe Leu Lys Ser Asp Gly Phe Ala Asn Arg Asn Phe Met Gln Leu Ile
            690                 695                 700
His Asp Asp Ser Leu Thr Phe Lys Glu Asp Ile Gln Lys Ala Gln Val
705                 710                 715                 720
Ser Gly Gln Gly Asp Ser Leu His Glu His Ile Ala Asn Leu Ala Gly
                725                 730                 735
Ser Pro Ala Ile Lys Lys Gly Ile Leu Gln Thr Val Lys Val Val Asp
                740                 745                 750
Glu Leu Val Lys Val Met Gly Arg His Lys Pro Glu Asn Ile Val Ile
            755                 760                 765
Glu Met Ala Arg Glu Asn Gln Thr Thr Gln Lys Gly Gln Lys Asn Ser
770                 775                 780
Arg Glu Arg Met Lys Arg Ile Glu Gly Ile Lys Glu Leu Gly Ser
785                 790                 795                 800
Gln Ile Leu Lys Glu His Pro Val Glu Asn Thr Gln Leu Gln Asn Glu
                805                 810                 815
Lys Leu Tyr Leu Tyr Tyr Leu Gln Asn Gly Arg Asp Met Tyr Val Asp
                820                 825                 830
Gln Glu Leu Asp Ile Asn Arg Leu Ser Asp Tyr Asp Val Asp His Ile
            835                 840                 845
Val Pro Gln Ser Phe Leu Lys Asp Asp Ser Ile Asp Asn Lys Val Leu
850                 855                 860
Thr Arg Ser Asp Lys Asn Arg Gly Lys Ser Asp Asn Val Pro Ser Glu
865                 870                 875                 880
Glu Val Val Lys Lys Met Lys Asn Tyr Trp Arg Gln Leu Leu Asn Ala
                885                 890                 895
Lys Leu Ile Thr Gln Arg Lys Phe Asp Asn Leu Thr Lys Ala Glu Arg
            900                 905                 910
Gly Gly Leu Ser Glu Leu Asp Lys Ala Gly Phe Ile Lys Arg Gln Leu
            915                 920                 925
Val Glu Thr Arg Gln Ile Thr Lys His Val Ala Gln Ile Leu Asp Ser
            930                 935                 940
Arg Met Asn Thr Lys Tyr Asp Glu Asn Asp Lys Leu Ile Arg Glu Val
945                 950                 955                 960
Lys Val Ile Thr Leu Lys Ser Lys Leu Val Ser Asp Phe Arg Lys Asp
                965                 970                 975
```

-continued

Phe Gln Phe Tyr Lys Val Arg Glu Ile Asn Asn Tyr His His Ala His
            980                 985                 990

Asp Ala Tyr Leu Asn Ala Val Val Gly Thr Ala Leu Ile Lys Lys Tyr
            995                 1000                1005

Pro Lys Leu Glu Ser Glu Phe Val Tyr Gly Asp Tyr Lys Val Tyr
            1010                1015                1020

Asp Val Arg Lys Met Ile Ala Lys Ser Glu Gln Glu Ile Gly Lys
            1025                1030                1035

Ala Thr Ala Lys Tyr Phe Phe Tyr Ser Asn Ile Met Asn Phe Phe
            1040                1045                1050

Lys Thr Glu Ile Thr Leu Ala Asn Gly Glu Ile Arg Lys Arg Pro
            1055                1060                1065

Leu Ile Glu Thr Asn Gly Glu Thr Gly Glu Ile Val Trp Asp Lys
            1070                1075                1080

Gly Arg Asp Phe Ala Thr Val Arg Lys Val Leu Ser Met Pro Gln
            1085                1090                1095

Val Asn Ile Val Lys Lys Thr Glu Val Gln Thr Gly Gly Phe Ser
            1100                1105                1110

Lys Glu Ser Ile Leu Pro Lys Arg Asn Ser Asp Lys Leu Ile Ala
            1115                1120                1125

Arg Lys Lys Asp Trp Asp Pro Lys Lys Tyr Gly Gly Phe Asp Ser
            1130                1135                1140

Pro Thr Val Ala Tyr Ser Val Leu Val Val Ala Lys Val Glu Lys
            1145                1150                1155

Gly Lys Ser Lys Lys Leu Lys Ser Val Lys Glu Leu Leu Gly Ile
            1160                1165                1170

Thr Ile Met Glu Arg Ser Ser Phe Glu Lys Asn Pro Ile Asp Phe
            1175                1180                1185

Leu Glu Ala Lys Gly Tyr Lys Glu Val Lys Lys Asp Leu Ile Ile
            1190                1195                1200

Lys Leu Pro Lys Tyr Ser Leu Phe Glu Leu Glu Asn Gly Arg Lys
            1205                1210                1215

Arg Met Leu Ala Ser Ala Gly Glu Leu Gln Lys Gly Asn Glu Leu
            1220                1225                1230

Ala Leu Pro Ser Lys Tyr Val Asn Phe Leu Tyr Leu Ala Ser His
            1235                1240                1245

Tyr Glu Lys Leu Lys Gly Ser Pro Glu Asp Asn Glu Gln Lys Gln
            1250                1255                1260

Leu Phe Val Glu Gln His Lys His Tyr Leu Asp Glu Ile Ile Glu
            1265                1270                1275

Gln Ile Ser Glu Phe Ser Lys Arg Val Ile Leu Ala Asp Ala Asn
            1280                1285                1290

Leu Asp Lys Val Leu Ser Ala Tyr Asn Lys His Arg Asp Lys Pro
            1295                1300                1305

Ile Arg Glu Gln Ala Glu Asn Ile Ile His Leu Phe Thr Leu Thr
            1310                1315                1320

Asn Leu Gly Ala Pro Ala Ala Phe Lys Tyr Phe Asp Thr Thr Ile
            1325                1330                1335

Asp Arg Lys Arg Tyr Thr Ser Thr Lys Glu Val Leu Asp Ala Thr
            1340                1345                1350

Leu Ile His Gln Ser Ile Thr Gly Leu Tyr Glu Thr Arg Ile Asp
            1355                1360                1365

Leu Ser Gln Leu Gly Gly Asp Lys Arg Pro Ala Ala Thr Lys Lys

Ala Gly Gln Ala Lys Lys Lys Lys
     1385           1390

<210> SEQ ID NO 36
<211> LENGTH: 4176
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Start Codon
<220> FEATURE:
<221> NAME/KEY: misc_feature
<222> LOCATION: (10)..(30)
<223> OTHER INFORMATION: 5' NLS
<220> FEATURE:
<221> NAME/KEY: misc_feature
<222> LOCATION: (4126)..(4173)
<223> OTHER INFORMATION: 3' NLS
<220> FEATURE:
<221> NAME/KEY: misc_feature
<222> LOCATION: (4174)..(4176)
<223> OTHER INFORMATION: Stop Codon

<400> SEQUENCE: 36

```
atggacaagc ccaagaaaaa gcggaaagtg aagtacagca tcggcctgga catcggcacc    60
aactctgtgg gctgggccgt gatcaccgac gagtacaagg tgcccagcaa gaaattcaag   120
gtgctgggca acaccgacag gcacagcatc aagaagaacc tgatcggcgc cctgctgttc   180
gacagcggcg aaacagccga ggccaccaga ctgaagagaa ccgccagaag aagatacacc   240
aggcggaaga caggatctg ctatctgcaa gagatcttca gcaacgagat ggccaaggtg   300
gacgacagct tcttccacag actggaagag tccttcctgg tggaagagga caagaagcac   360
gagagacacc ccatcttcgg caacatcgtg gacgaggtgg cctaccacga agtacccc   420
accatctacc acctgagaaa gaaactggtg gacagcaccg acaaggccga cctgagactg   480
atctacctgg ccctggccca catgatcaag ttcagaggcc acttcctgat cgagggcgac   540
ctgaaccccg acaacagcga cgtggacaag ctgttcatcc agctggtgca gacctacaac   600
cagctgttcg aggaaaaccc catcaacgcc agcggcgtgg acgccaaggc tatcctgtct   660
gccagactga gcaagagcag aaggctggaa atctgatcg cccagctgcc cggcgagaag   720
aagaacggcc tgttcggcaa cctgattgcc ctgagcctgg gcctgacccc caacttcaag   780
agcaacttcg acctggccga ggatgccaaa ctgcagctga gcaaggacac ctacgacgac   840
gacctggaca acctgctggc ccagatcggc gaccagtacg ccgacctgtt cctggccgcc   900
aagaacctgt ctgacgccat cctgctgagc gacatcctga gtgaacac cgagatcacc   960
aaggcccccc tgagcgcctc tatgatcaag agatacgacg agcaccacca ggacctgacc  1020
ctgctgaaag ctctcgtgcg gcagcagctg cctgagaagt acaaagaaat cttcttcgac  1080
cagagcaaga acggctacgc cggctacatc gatggcggcg ctagccagga gagttctac  1140
aagttcatca gcccatcct ggaaaagatg gacggcaccg aggaactgct cgtgaagctg  1200
aacagagagg acctgctgag aaagcagaga accttcgaca acggcagcat cccccaccag  1260
atccacctgg gagagctgca cgctatcctg agaaggcagg aagattttta cccattcctg  1320
aaggacaacc gggaaaagat cgagaagatc ctgaccttca ggatcccta ctacgtgggc  1380
cccctggcca gaggcaacag cagattcgcc tggatgacca gaaagagcga ggaaaccatc  1440
```

```
accccctgga acttcgagga agtggtggac aagggcgcca gcgcccagag cttcatcgag   1500
agaatgacaa acttcgataa gaacctgccc aacgagaagg tgctgcccaa gcacagcctg   1560
ctgtacgagt acttcaccgt gtacaacgag ctgaccaaag tgaaatacgt gaccgaggga   1620
atgagaaagc ccgccttcct gagcggcgag cagaaaaagg ccatcgtgga cctgctgttc   1680
aagaccaaca gaaaagtgac cgtgaagcag ctgaaagagg actacttcaa gaaaatcgag   1740
tgcttcgact ccgtggaaat ctccggcgtg gaagatagat caacgcctc cctgggcaca   1800
taccacgatc tgctgaaaat tatcaaggac aaggacttcc tggataacga agagaacgag   1860
gacattctgg aagatatcgt gctgaccctg acactgtttg aggaccgcga gatgatcgag   1920
gaaaggctga aaacctacgc tcacctgttc gacgacaaag tgatgaagca gctgaagaga   1980
aggcggtaca ccggctgggg caggctgagc agaaagctga tcaacggcat cagagacaag   2040
cagagcggca agacaatcct ggatttcctg aagtccgacg gcttcgccaa ccggaacttc   2100
atgcagctga tccacgacga cagcctgaca ttcaaagagg acatccagaa agcccaggtg   2160
tccggccagg gcgactctct gcacgagcat atcgctaacc tggccggcag ccccgctatc   2220
aagaagggca tcctgcagac agtgaaggtg gtggacgagc tcgtgaaagt gatgggcaga   2280
cacaagcccg agaacatcgt gatcgagatg gctagagaga ccagaccac ccagaaggga   2340
cagaagaact cccgcgagag gatgaagaga atcgaagagg gcatcaaaga gctgggcagc   2400
cagatcctga aagaacaccc cgtggaaaac acccagctgc agaacgagaa gctgtacctg   2460
tactacctgc agaatggccg ggatatgtac gtggaccagg aactggacat caacagactg   2520
tccgactacg atgtggacca tatcgtgcct cagagctttc tgaaggacga ctccatcgat   2580
aacaaagtgc tgactcggag cgacaagaac agaggcaaga gcgacaacgt gccctccgaa   2640
gaggtcgtga gaagatgaa gaactactgg cgacagctgc tgaacgccaa gctgattacc   2700
cagaggaagt tcgataacct gaccaaggcc gagagaggcg gcctgagcga gctggataag   2760
gccggcttca tcaagaggca gctggtggaa accagacaga tcacaaagca cgtggcacag   2820
atcctggact cccggatgaa cactaagtac gacgaaaacg ataagctgat ccgggaagtg   2880
aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtaccctaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aactttttca agaccgaaat caccctggcc   3180
aacggcgaga tcagaaagcg ccctctgatc gagacaaacg gcgaaaccgg ggagatcgtg   3240
tgggataagg gcagagactt cgccacagtg cgaaaggtgc tgagcatgcc ccaagtgaat   3300
atcgtgaaaa agaccgaggt gcagacaggc ggcttcagca agagtctat cctgcccaag   3360
aggaacagcg acaagctgat cgccagaaag aaggactggg accccaagaa gtacggcggc   3420
ttcgacagcc ctaccgtggc ctactctgtg ctggtggtgg ctaaggtgga aaagggcaag   3480
tccaagaaac tgaagagtgt gaaagagctg ctggggatca ccatcatgga agaagcagc   3540
tttgagaaga accctatcga ctttctggaa gccaagggct acaaagaagt gaaaaaggac   3600
ctgatcatca agctgcctaa gtactccctg ttcgagctgg aaaacggcag aaagagaatg   3660
ctggcctctg ccggcgaact gcagaaggga acgagctgg ccctgcctag caaatatgtg   3720
aacttcctgt acctggcctc ccactatgag aagctgaagg gcagccctga ggacaacgaa   3780
cagaaacagc tgtttgtgga acagcataag cactacctgg acgagatcat cgagcagatc   3840
```

-continued

```
agcgagttct ccaagagagt gatcctggcc gacgccaatc tggacaaggt gctgtctgcc    3900
tacaacaagc acagggacaa gcctatcaga gagcaggccg agaatatcat ccacctgttc    3960
accctgacaa acctgggcgc tcctgccgcc ttcaagtact ttgacaccac catcgaccgg    4020
aagaggtaca ccagcaccaa agaggtgctg gacgccaccc tgatccacca gagcatcacc    4080
ggcctgtacg agacaagaat cgacctgtct cagctgggag gcgacaagag acctgccgcc    4140
actaagaagg ccggacaggc caaaaagaag aagtga                              4176
```

```
<210> SEQ ID NO 37
<211> LENGTH: 16
<212> TYPE: RNA
<213> ORGANISM: Artificial Sequence
<220> FEATURE:
<223> OTHER INFORMATION: Synthetic

<400> SEQUENCE: 37
guuuuagagc uaugcu                                                    16

<210> SEQ ID NO 38
<211> LENGTH: 67
<212> TYPE: RNA
<213> ORGANISM: Artificial Sequence
<220> FEATURE:
<223> OTHER INFORMATION: Synthetic

<400> SEQUENCE: 38
agcauagcaa guuaaaauaa ggcuaguccg uuaucaacuu gaaaaagugg caccgagucg    60
gugcuuu                                                              67

<210> SEQ ID NO 39
<211> LENGTH: 77
<212> TYPE: RNA
<213> ORGANISM: Artificial Sequence
<220> FEATURE:
<223> OTHER INFORMATION: Synthetic

<400> SEQUENCE: 39
guuuuagagc uagaaauagc aaguuaaaau aaggcuaguc cguuaucaac uugaaaaagu    60
ggcaccgagu cggugcu                                                   77

<210> SEQ ID NO 40
<211> LENGTH: 82
<212> TYPE: RNA
<213> ORGANISM: Artificial Sequence
<220> FEATURE:
<223> OTHER INFORMATION: Synthetic

<400> SEQUENCE: 40
guuggaacca uucaaaacag cauagcaagu uaaauaagg cuaguccguu aucaacuuga     60
aaaaguggca ccgagucggu gc                                             82

<210> SEQ ID NO 41
<211> LENGTH: 76
<212> TYPE: RNA
<213> ORGANISM: Artificial Sequence
<220> FEATURE:
<223> OTHER INFORMATION: Synthetic

<400> SEQUENCE: 41
guuuuagagc uagaaauagc aaguuaaaau aaggcuaguc cguuaucaac uugaaaaagu    60
```

```
ggcaccgagu cggugc                                             76

<210> SEQ ID NO 42
<211> LENGTH: 86
<212> TYPE: RNA
<213> ORGANISM: Artificial Sequence
<220> FEATURE:
<223> OTHER INFORMATION: Synthetic

<400> SEQUENCE: 42
guuuaagagc uaugcuggaa acagcauagc aaguuuaaau aaggcuaguc cguuaucaac    60
uugaaaaagu ggcaccgagu cggugc                                        86

<210> SEQ ID NO 43
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n is a, c, g, or t

<400> SEQUENCE: 43
gnnnnnnnnn nnnnnnnnnn ngg                                           23

<210> SEQ ID NO 44
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n is a, c, g, or t

<400> SEQUENCE: 44
nnnnnnnnnn nnnnnnnnnn ngg                                           23

<210> SEQ ID NO 45
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n is a, c, g, or t

<400> SEQUENCE: 45
ggnnnnnnnn nnnnnnnnnn nnngg                                         25

<210> SEQ ID NO 46
<211> LENGTH: 615
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Signal Peptide
<220> FEATURE:
<221> NAME/KEY: MISC_FEATURE
<222> LOCATION: (20)..(372)
<223> OTHER INFORMATION: Heavy Chain
<220> FEATURE:
<221> NAME/KEY: MISC_FEATURE
```

-continued

```
<222> LOCATION: (373)..(615)
<223> OTHER INFORMATION: Light Chain

<400> SEQUENCE: 46
```

| Met | Arg | Ala | Leu | Leu | Leu | Gly | Phe | Leu | Leu | Val | Ser | Leu | Glu | Ser |
|---|---|---|---|---|---|---|---|---|---|---|---|---|---|---|
| 1 | | | | 5 | | | | | 10 | | | | | 15 |

| Thr | Leu | Ser | Ile | Pro | Pro | Trp | Glu | Ala | Pro | Lys | Glu | His | Lys | Tyr | Lys |
|---|---|---|---|---|---|---|---|---|---|---|---|---|---|---|---|
| | | | | 20 | | | | | 25 | | | | | 30 | |

| Ala | Glu | Glu | His | Thr | Val | Val | Leu | Thr | Val | Thr | Gly | Glu | Pro | Cys | His |
|---|---|---|---|---|---|---|---|---|---|---|---|---|---|---|---|
| | | | 35 | | | | | 40 | | | | | 45 | | |

| Phe | Pro | Phe | Gln | Tyr | His | Arg | Gln | Leu | Tyr | His | Lys | Cys | Thr | His | Lys |
|---|---|---|---|---|---|---|---|---|---|---|---|---|---|---|---|
| | 50 | | | | | 55 | | | | | 60 | | | | |

| Gly | Arg | Pro | Gly | Pro | Gln | Pro | Trp | Cys | Ala | Thr | Thr | Pro | Asn | Phe | Asp |
|---|---|---|---|---|---|---|---|---|---|---|---|---|---|---|---|
| 65 | | | | | 70 | | | | | 75 | | | | | 80 |

| Gln | Asp | Gln | Arg | Trp | Gly | Tyr | Cys | Leu | Glu | Pro | Lys | Lys | Val | Lys | Asp |
|---|---|---|---|---|---|---|---|---|---|---|---|---|---|---|---|
| | | | | 85 | | | | | 90 | | | | | 95 | |

| His | Cys | Ser | Lys | His | Ser | Pro | Cys | Gln | Lys | Gly | Gly | Thr | Cys | Val | Asn |
|---|---|---|---|---|---|---|---|---|---|---|---|---|---|---|---|
| | | | 100 | | | | | 105 | | | | | 110 | | |

| Met | Pro | Ser | Gly | Pro | His | Cys | Leu | Cys | Pro | Gln | His | Leu | Thr | Gly | Asn |
|---|---|---|---|---|---|---|---|---|---|---|---|---|---|---|---|
| | | | 115 | | | | | 120 | | | | | 125 | | |

| His | Cys | Gln | Lys | Glu | Lys | Cys | Phe | Glu | Pro | Gln | Leu | Leu | Arg | Phe | Phe |
|---|---|---|---|---|---|---|---|---|---|---|---|---|---|---|---|
| | 130 | | | | | 135 | | | | | 140 | | | | |

| His | Lys | Asn | Glu | Ile | Trp | Tyr | Arg | Thr | Glu | Gln | Ala | Ala | Val | Ala | Arg |
|---|---|---|---|---|---|---|---|---|---|---|---|---|---|---|---|
| 145 | | | | | 150 | | | | | 155 | | | | | 160 |

| Cys | Gln | Cys | Lys | Gly | Pro | Asp | Ala | His | Cys | Gln | Arg | Leu | Ala | Ser | Gln |
|---|---|---|---|---|---|---|---|---|---|---|---|---|---|---|---|
| | | | | 165 | | | | | 170 | | | | | 175 | |

| Ala | Cys | Arg | Thr | Asn | Pro | Cys | Leu | His | Gly | Gly | Arg | Cys | Leu | Glu | Val |
|---|---|---|---|---|---|---|---|---|---|---|---|---|---|---|---|
| | | | 180 | | | | | 185 | | | | | 190 | | |

| Glu | Gly | His | Arg | Leu | Cys | His | Cys | Pro | Val | Gly | Tyr | Thr | Gly | Ala | Phe |
|---|---|---|---|---|---|---|---|---|---|---|---|---|---|---|---|
| | | | 195 | | | | | 200 | | | | | 205 | | |

| Cys | Asp | Val | Asp | Thr | Lys | Ala | Ser | Cys | Tyr | Asp | Gly | Arg | Gly | Leu | Ser |
|---|---|---|---|---|---|---|---|---|---|---|---|---|---|---|---|
| | 210 | | | | | 215 | | | | | 220 | | | | |

| Tyr | Arg | Gly | Leu | Ala | Arg | Thr | Thr | Leu | Ser | Gly | Ala | Pro | Cys | Gln | Pro |
|---|---|---|---|---|---|---|---|---|---|---|---|---|---|---|---|
| 225 | | | | | 230 | | | | | 235 | | | | | 240 |

| Trp | Ala | Ser | Glu | Ala | Thr | Tyr | Arg | Asn | Val | Thr | Ala | Glu | Gln | Ala | Arg |
|---|---|---|---|---|---|---|---|---|---|---|---|---|---|---|---|
| | | | | 245 | | | | | 250 | | | | | 255 | |

| Asn | Trp | Gly | Leu | Gly | Gly | His | Ala | Phe | Cys | Arg | Asn | Pro | Asp | Asn | Asp |
|---|---|---|---|---|---|---|---|---|---|---|---|---|---|---|---|
| | | | 260 | | | | | 265 | | | | | 270 | | |

| Ile | Arg | Pro | Trp | Cys | Phe | Val | Leu | Asn | Arg | Asp | Arg | Leu | Ser | Trp | Glu |
|---|---|---|---|---|---|---|---|---|---|---|---|---|---|---|---|
| | | 275 | | | | | 280 | | | | | 285 | | | |

| Tyr | Cys | Asp | Leu | Ala | Gln | Cys | Gln | Thr | Pro | Thr | Gln | Ala | Ala | Pro | Pro |
|---|---|---|---|---|---|---|---|---|---|---|---|---|---|---|---|
| | 290 | | | | | 295 | | | | | 300 | | | | |

| Thr | Pro | Val | Ser | Pro | Arg | Leu | His | Val | Pro | Leu | Met | Pro | Ala | Gln | Pro |
|---|---|---|---|---|---|---|---|---|---|---|---|---|---|---|---|
| 305 | | | | | 310 | | | | | 315 | | | | | 320 |

| Ala | Pro | Pro | Lys | Pro | Gln | Pro | Thr | Thr | Arg | Thr | Pro | Pro | Gln | Ser | Gln |
|---|---|---|---|---|---|---|---|---|---|---|---|---|---|---|---|
| | | | | 325 | | | | | 330 | | | | | 335 | |

| Thr | Pro | Gly | Ala | Leu | Pro | Ala | Lys | Arg | Glu | Gln | Pro | Pro | Ser | Leu | Thr |
|---|---|---|---|---|---|---|---|---|---|---|---|---|---|---|---|
| | | | 340 | | | | | 345 | | | | | 350 | | |

| Arg | Asn | Gly | Pro | Leu | Ser | Cys | Gly | Gln | Arg | Leu | Arg | Lys | Ser | Leu | Ser |
|---|---|---|---|---|---|---|---|---|---|---|---|---|---|---|---|
| | | 355 | | | | | 360 | | | | | 365 | | | |

| Ser | Met | Thr | Arg | Val | Val | Gly | Gly | Leu | Val | Ala | Leu | Arg | Gly | Ala | His |
|---|---|---|---|---|---|---|---|---|---|---|---|---|---|---|---|
| | 370 | | | | | 375 | | | | | 380 | | | | |

| Pro | Tyr | Ile | Ala | Ala | Leu | Tyr | Trp | Gly | His | Ser | Phe | Cys | Ala | Gly | Ser |
|---|---|---|---|---|---|---|---|---|---|---|---|---|---|---|---|
| 385 | | | | | 390 | | | | | 395 | | | | | 400 |

```
Leu Ile Ala Pro Cys Trp Val Leu Thr Ala Ala His Cys Leu Gln Asp
            405                 410                 415

Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
            435                 440                 445

Leu His Glu Ala Phe Ser Pro Val Ser Tyr Gln His Asp Leu Ala Leu
            450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
            485                 490                 495

Thr Thr Leu Cys Gln Val Ala Gly Trp Gly His Gln Phe Glu Gly Ala
            500                 505                 510

Glu Glu Tyr Ala Ser Phe Leu Gln Glu Ala Gln Val Pro Phe Leu Ser
            515                 520                 525

Leu Glu Arg Cys Ser Ala Pro Asp Val His Gly Ser Ser Ile Leu Pro
            530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
            565                 570                 575

Arg Leu Thr Leu Gln Gly Ile Ile Ser Trp Gly Ser Gly Cys Gly Asp
            580                 585                 590

Arg Asn Lys Pro Gly Val Tyr Thr Asp Val Ala Tyr Tyr Leu Ala Trp
            595                 600                 605

Ile Arg Glu His Thr Val Ser
610                 615

<210> SEQ ID NO 47
<211> LENGTH: 353
<212> TYPE: PRT
<213> ORGANISM: Homo sapiens

<400> SEQUENCE: 47

Ile Pro Pro Trp Glu Ala Pro Lys Glu His Lys Tyr Lys Ala Glu Glu
1               5                   10                  15

His Thr Val Val Leu Thr Val Thr Gly Glu Pro Cys His Phe Pro Phe
            20                  25                  30

Gln Tyr His Arg Gln Leu Tyr His Lys Cys Thr His Lys Gly Arg Pro
            35                  40                  45

Gly Pro Gln Pro Trp Cys Ala Thr Thr Pro Asn Phe Asp Gln Asp Gln
        50                  55                  60

Arg Trp Gly Tyr Cys Leu Glu Pro Lys Lys Val Lys Asp His Cys Ser
65                  70                  75                  80

Lys His Ser Pro Cys Gln Lys Gly Gly Thr Cys Val Asn Met Pro Ser
            85                  90                  95

Gly Pro His Cys Leu Cys Pro Gln His Leu Thr Gly Asn His Cys Gln
            100                 105                 110

Lys Glu Lys Cys Phe Glu Pro Gln Leu Leu Arg Phe Phe His Lys Asn
            115                 120                 125

Glu Ile Trp Tyr Arg Thr Glu Gln Ala Ala Val Ala Arg Cys Gln Cys
            130                 135                 140

Lys Gly Pro Asp Ala His Cys Gln Arg Leu Ala Ser Gln Ala Cys Arg
```

```
                145                 150                 155                 160
Thr Asn Pro Cys Leu His Gly Gly Arg Cys Leu Glu Val Glu Gly His
                    165                 170                 175
Arg Leu Cys His Cys Pro Val Gly Tyr Thr Gly Ala Phe Cys Asp Val
                    180                 185                 190
Asp Thr Lys Ala Ser Cys Tyr Asp Gly Arg Gly Leu Ser Tyr Arg Gly
                    195                 200                 205
Leu Ala Arg Thr Thr Leu Ser Gly Ala Pro Cys Gln Pro Trp Ala Ser
                    210                 215                 220
Glu Ala Thr Tyr Arg Asn Val Thr Ala Glu Gln Ala Arg Asn Trp Gly
225                 230                 235                 240
Leu Gly Gly His Ala Phe Cys Arg Asn Pro Asp Asn Asp Ile Arg Pro
                    245                 250                 255
Trp Cys Phe Val Leu Asn Arg Asp Arg Leu Ser Trp Glu Tyr Cys Asp
                    260                 265                 270
Leu Ala Gln Cys Gln Thr Pro Thr Gln Ala Ala Pro Pro Thr Pro Val
                    275                 280                 285
Ser Pro Arg Leu His Val Pro Leu Met Pro Ala Gln Pro Ala Pro Pro
                    290                 295                 300
Lys Pro Gln Pro Thr Thr Arg Thr Pro Pro Gln Ser Gln Thr Pro Gly
305                 310                 315                 320
Ala Leu Pro Ala Lys Arg Glu Gln Pro Pro Ser Leu Thr Arg Asn Gly
                    325                 330                 335
Pro Leu Ser Cys Gly Gln Arg Leu Arg Lys Ser Leu Ser Ser Met Thr
                    340                 345                 350
Arg

<210> SEQ ID NO 48
<211> LENGTH: 1848
<212> TYPE: DNA
<213> ORGANISM: Homo sapiens
<220> FEATURE:
<221> NAME/KEY: misc_feature
<222> LOCATION: (1)..(57)
<223> OTHER INFORMATION: Signal Peptide
<220> FEATURE:
<221> NAME/KEY: misc_feature
<222> LOCATION: (58)..(1116)
<223> OTHER INFORMATION: Heavy Chain
<220> FEATURE:
<221> NAME/KEY: misc_feature
<222> LOCATION: (1117)..(1845)
<223> OTHER INFORMATION: Light Chain

<400> SEQUENCE: 48
atgagggctc tgctgctcct ggggttcctg ctggtgagct ggagtcaac actttcgatt        60 ccaccttggg aagcccccaa ggagcataag tacaaagctg aagagcacac agtcgttctc     120
actgtcaccg gggagccctg ccacttcccc ttccagtacc accggcagct gtaccacaaa     180
tgtacccaca agggccggcc aggccctcag ccctggtgtg ctaccacccc caactttgat     240
caggaccagc gatggggata ctgtttggag cccaagaaag tgaaagacca ctgcagcaaa     300
cacagcccct gccagaaagg agggacctgt gtgaacatgc caagcggccc ccactgtctc     360
tgtccacaac acctcactgg aaaccactgc cagaaagaga gtgctttga gcctcagctt     420 ctccggtttt tccacaagaa tgagatatgg tatagaactg agcaagcagc tgtggccaga     480
tgccagtgca agggtcctga tgcccactgc agcggctgg ccagccaggc ctgccgcacc     540
aacccgtgcc tccatggggg tcgctgccta gaggtggagg ccaccgcct gtgccactgc     600
```

```
ccggtgggct acaccggagc cttctgcgac gtggacacca aggcaagctg ctatgatggc      660
cgcgggctca gctaccgcgg cctggccagg accacgctct cgggtgcgcc ctgtcagccg      720
tgggcctcgg aggccaccta ccggaacgtg actgccgagc aagcgcggaa ctggggactg      780
ggcggccacg ccttctgccg gaacccggac aacgacatcc gcccgtggtg cttcgtgctg      840
aaccgcgacc ggctgagctg ggagtactgc gacctggcac agtgccagac cccaacccag      900
gcggcgcctc cgaccccggt gtccctagg cttcatgtcc cactcatgcc cgcgcagccg       960
gcaccgccga agcctcagcc cacgacccgg accccgcctc agtcccagac cccgggagcc     1020
ttgccggcga agcgggagca gccgccttcc ctgaccagga acggcccact gagctgcggg     1080
cagcggctcc gcaagagtct gtcttcgatg accgcgtcg ttggcgggct ggtggcgcta      1140
cgcggggcgc accctacat cgccgcgctg tactgggggcc acagtttctg cgccggcagc     1200
ctcatcgccc cctgctgggt gctgacggcc gctcactgcc tgcaggaccg gcccgcaccc     1260
gaggatctga cggtggtgct cggccaggaa cgccgtaacc acagctgtga gccgtgccag     1320
acgttggccg tgcgctccta ccgcttgcac gaggccttct cgcccgtcag ctaccagcac     1380
gacctggctc tgttgcgcct tcaggaggat gcggacggca gctgcgcgct cctgtcgcct     1440
tacgttcagc cggtgtgcct gccaagcggc gccgcgcgac cctccgagac cacgctctgc     1500
caggtggccg gctggggcca ccagttcgag ggggcggagg aatatgccag cttcctgcag     1560
gaggcgcagg taccgttcct ctccctggag cgctgctcag ccccggacgt gcacggatcc     1620
tccatcctcc ccggcatgct ctgcgcaggg ttcctcgagg gcggaccga tgcgtgccag      1680 ggtgattccg gaggcccgct ggtgtgtgag gaccaagctg cagagcgccg gctcaccctg     1740
caaggcatca tcagctgggg atcgggctgt ggtgaccgca acaagccagg cgtctacacc     1800
gatgtggcct actacctggc ctggatccgg gagcacaccg tttcctga                 1848

<210> SEQ ID NO 49
<211> LENGTH: 1059
<212> TYPE: DNA
<213> ORGANISM: Homo sapiens

<400> SEQUENCE: 49
attccacctt gggaagcccc caaggagcat aagtacaaag ctgaagagca cacagtcgtt       60
ctcactgtca ccggggagcc ctgccacttc cccttccagt accaccggca gctgtaccac      120
aaatgtaccc acaagggccg gccaggccct cagccctggt gtgctaccac ccccaacttt      180
gatcaggacc agcgatgggg atactgtttg gagcccaaga agtgaaaga ccactgcagc       240 aaacacagcc cctgccagaa aggagggacc tgtgtgaaca tgccaagcgg cccccactgt      300
ctctgtccac aacacctcac tggaaaccac tgccagaaag agaagtgctt tgagcctcag      360
cttctccggt ttttccacaa gaatgagata tggtatagaa ctgagcaagc agctgtggcc      420
agatgccagt gcaagggtcc tgatgcccac tgccagcggc tggccagcca ggcctgccgc      480
accaacccgt gcctccatgg gggtcgctgc ctagaggtgg agggccaccg cctgtgccac      540
tgcccggtgg gctacaccgg agccttctgc gacgtggaca ccaaggcaag ctgctatgat      600
ggccgcgggc tcagctaccg cggcctggcc aggaccacgc tctcgggtgc gccctgtcag      660
ccgtgggcct cggaggccac ctaccggaac gtgactgccg agcaagcgcg gaactgggga      720
ctgggcggcc acgccttctg ccggaacccg gacaacgaca tccgcccgtg gtgcttcgtg      780
ctgaaccgcg accggctgag ctgggagtac tgcgacctgg cacagtgcca gaccccaacc      840
```

-continued

```
caggcggcgc ctccgacccc ggtgtcccct aggcttcatg tcccactcat gcccgcgcag      900
ccggcaccgc cgaagcctca gcccacgacc cggaccccgc ctcagtccca gaccccggga      960
gccttgccgg cgaagcggga gcagccgcct ccctgacca ggaacggccc actgagctgc      1020
gggcagcggc tccgcaagag tctgtcttcg atgacccgc                            1059
```

<210> SEQ ID NO 50
<211> LENGTH: 18
<212> TYPE: DNA
<213> ORGANISM: Artificial Sequence
<220> FEATURE:
<223> OTHER INFORMATION: Synthetic

<400> SEQUENCE: 50

```
tggaccaacg gacggatg                                                     18
```

<210> SEQ ID NO 51
<211> LENGTH: 18
<212> TYPE: DNA
<213> ORGANISM: Artificial Sequence
<220> FEATURE:
<223> OTHER INFORMATION: Synthetic

<400> SEQUENCE: 51

```
tgccacttcc ccttccag                                                     18
```

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52

```
actgtctctg tccacaacac c                                                 21
```

<210> SEQ ID NO 53
<211> LENGTH: 18
<212> TYPE: DNA
<213> ORGANISM: Artificial Sequence
<220> FEATURE:
<223> OTHER INFORMATION: Synthetic

<400> SEQUENCE: 53

```
accaacccgt gcctccat                                                     18
```

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54

```
gtggtgcttc gtgctgaac                                                    19
```

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55

```
aggatctgac ggtggtgctc                                                   20
```

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
acaccgatgt ggcctactac                                            20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
ccaggtggtc tcctctgact                                            20

<210> SEQ ID NO 58
<211> LENGTH: 21
<212> TYPE: DNA
<213> ORGANISM: Artificial Sequence
<220> FEATURE:
<223> OTHER INFORMATION: Synthetic

<400> SEQUENCE: 58
cccaaggtgg aatcgaaagt g                                          21

<210> SEQ ID NO 59
<211> LENGTH: 19
<212> TYPE: DNA
<213> ORGANISM: Artificial Sequence
<220> FEATURE:
<223> OTHER INFORMATION: Synthetic

<400> SEQUENCE: 59
gtagcacacc agggctgag                                             19

<210> SEQ ID NO 60
<211> LENGTH: 21
<212> TYPE: DNA
<213> ORGANISM: Artificial Sequence
<220> FEATURE:
<223> OTHER INFORMATION: Synthetic

<400> SEQUENCE: 60
cggagaagct gaggctcaaa g                                          21

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
gcagaaggct ccggtgtag                                             19

<210> SEQ ID NO 62
<211> LENGTH: 19
<212> TYPE: DNA
<213> ORGANISM: Artificial Sequence
<220> FEATURE:

<223> OTHER INFORMATION: Synthetic

<400> SEQUENCE: 62
gttggggtct ggcactgtg                                          19

<210> SEQ ID NO 63
<211> LENGTH: 19
<212> TYPE: DNA
<213> ORGANISM: Artificial Sequence
<220> FEATURE:
<223> OTHER INFORMATION: Synthetic

<400> SEQUENCE: 63
gtagctgacg ggcgagaag                                          19

<210> SEQ ID NO 64
<211> LENGTH: 19
<212> TYPE: DNA
<213> ORGANISM: Artificial Sequence
<220> FEATURE:
<223> OTHER INFORMATION: Synthetic

<400> SEQUENCE: 64
actgcggaat caccaagga                                          19

<210> SEQ ID NO 65
<211> LENGTH: 21
<212> TYPE: DNA
<213> ORGANISM: Artificial Sequence
<220> FEATURE:
<223> OTHER INFORMATION: Synthetic

<400> SEQUENCE: 65
gcttgacaaa gtggtcgttg a                                       21

<210> SEQ ID NO 66
<211> LENGTH: 23
<212> TYPE: DNA
<213> ORGANISM: Artificial Sequence
<220> FEATURE:
<223> OTHER INFORMATION: Synthetic

<400> SEQUENCE: 66
catgagggct ctgctgctcc tgg                                     23

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
accaccggca gctgtaccac aaat                                    24

<210> SEQ ID NO 68
<211> LENGTH: 27
<212> TYPE: DNA
<213> ORGANISM: Artificial Sequence
<220> FEATURE:
<223> OTHER INFORMATION: Synthetic

<400> SEQUENCE: 68
tcactggaaa ccactgccag aaagaga                                 27

```
<210> SEQ ID NO 69
<211> LENGTH: 23
<212> TYPE: DNA
<213> ORGANISM: Artificial Sequence
<220> FEATURE:
<223> OTHER INFORMATION: Synthetic

<400> SEQUENCE: 69
ctgcctagag gtggagggcc acc                                               23

<210> SEQ ID NO 70
<211> LENGTH: 23
<212> TYPE: DNA
<213> ORGANISM: Artificial Sequence
<220> FEATURE:
<223> OTHER INFORMATION: Synthetic

<400> SEQUENCE: 70
cgaccggctg agctgggagt act                                               23

<210> SEQ ID NO 71
<211> LENGTH: 23
<212> TYPE: DNA
<213> ORGANISM: Artificial Sequence
<220> FEATURE:
<223> OTHER INFORMATION: Synthetic

<400> SEQUENCE: 71
ccaggaacgc cgtaaccaca gct                                               23

<210> SEQ ID NO 72
<211> LENGTH: 23
<212> TYPE: DNA
<213> ORGANISM: Artificial Sequence
<220> FEATURE:
<223> OTHER INFORMATION: Synthetic

<400> SEQUENCE: 72
ctggatccgg gagcacaccg ttt                                               23

<210> SEQ ID NO 73
<211> LENGTH: 22
<212> TYPE: DNA
<213> ORGANISM: Artificial Sequence
<220> FEATURE:
<223> OTHER INFORMATION: Synthetic

<400> SEQUENCE: 73
tcaacagcga cacccactcc tc                                                22

<210> SEQ ID NO 74
<211> LENGTH: 300
<212> TYPE: PRT
<213> ORGANISM: Homo sapiens

<400> SEQUENCE: 74

Met Pro Ala Gln Pro Ala Pro Lys Pro Gln Pro Thr Thr Arg Thr
1               5                   10                  15

Pro Pro Gln Ser Gln Thr Pro Gly Ala Leu Pro Ala Lys Arg Glu Gln
            20                  25                  30

Pro Pro Ser Leu Thr Arg Asn Gly Pro Leu Ser Cys Gly Gln Arg Leu
        35                  40                  45

Arg Lys Ser Leu Ser Ser Met Thr Arg Val Val Gly Gly Leu Val Ala
    50                  55                  60
```

```
Leu Arg Gly Ala His Pro Tyr Ile Ala Ala Leu Tyr Trp Gly His Ser
 65                  70                  75                  80

Phe Cys Ala Gly Ser Leu Ile Ala Pro Cys Trp Val Leu Thr Ala Ala
                 85                  90                  95

His Cys Leu Gln Asp Arg Pro Ala Pro Glu Asp Leu Thr Val Val Leu
            100                 105                 110

Gly Gln Glu Arg Arg Asn His Ser Cys Glu Pro Cys Gln Thr Leu Ala
        115                 120                 125

Val Arg Ser Tyr Arg Leu His Glu Ala Phe Ser Pro Val Ser Tyr Gln
    130                 135                 140

His Asp Leu Ala Leu Leu Arg Leu Gln Glu Asp Ala Asp Gly Ser Cys
145                 150                 155                 160

Ala Leu Leu Ser Pro Tyr Val Gln Pro Val Cys Leu Pro Ser Gly Ala
                165                 170                 175

Ala Arg Pro Ser Glu Thr Thr Leu Cys Gln Val Ala Gly Trp Gly His
            180                 185                 190

Gln Phe Glu Gly Ala Glu Glu Tyr Ala Ser Phe Leu Gln Glu Ala Gln
        195                 200                 205

Val Pro Phe Leu Ser Leu Glu Arg Cys Ser Ala Pro Asp Val His Gly
    210                 215                 220

Ser Ser Ile Leu Pro Gly Met Leu Cys Ala Gly Phe Leu Glu Gly Gly
225                 230                 235                 240

Thr Asp Ala Cys Gln Gly Asp Ser Gly Gly Pro Leu Val Cys Glu Asp
                245                 250                 255

Gln Ala Ala Glu Arg Arg Leu Thr Leu Gln Gly Ile Ile Ser Trp Gly
            260                 265                 270

Ser Gly Cys Gly Asp Arg Asn Lys Pro Gly Val Tyr Thr Asp Val Ala
        275                 280                 285

Tyr Tyr Leu Ala Trp Ile Arg Glu His Thr Val Ser
    290                 295                 300

<210> SEQ ID NO 75
<211> LENGTH: 903
<212> TYPE: DNA
<213> ORGANISM: Homo sapiens

<400> SEQUENCE: 75
atgcccgcgc agccggcacc gccgaagcct cagcccacga cccggacccc gcctcagtcc      60
cagaccccgg gagccttgcc ggcgaagcgg gagcagccgc cttccctgac caggaacggc     120
ccactgagct gcgggcagcg gctccgcaag agtctgtctt cgatgacccg gtcgttggc      180 gggctggtgg cgctacgcgg ggcgcacccc tacatcgccg cgctgtactg gggccacagt     240
ttctgcgccg gcagcctcat cgcccctgc tgggtgctga cggccgctca ctgcctgcag      300
gaccggcccg cacccgagga tctgacggtg gtgctcggcc aggaacgccg taaccacagc     360
tgtgagccgt gccagacgtt ggccgtgcgc tcctaccgct tgcacgaggc cttctcgccc     420
gtcagctacc agcacgacct ggctctgttg cgccttcagg aggatgcgga cggcagctgc     480
gcgctcctgt cgccttacgt tcagccggtg tgcctgccaa gcggcgccgc gcgaccctcc     540
gagaccacgc tctgccaggt ggccggctgg ggccaccagt tcgaggggc ggaggaatat      600 gccagcttcc tgcaggaggc gcaggtaccg ttcctctccc tggagcgctg ctcagccccg     660
gacgtgcacg gatcctccat cctccccggc atgctctgcg cagggttcct cgagggcggc     720
accgatgcgt gccagggtga ttccggaggc ccgctggtgt gtgaggacca agctgcagag     780
```

```
cgccggctca cccctgcaagg catcatcagc tggggatcgg gctgtggtga ccgcaacaag    840
ccaggcgtct acaccgatgt ggcctactac ctggcctgga tccgggagca caccgtttcc    900
tga                                                                   903
```

<210> SEQ ID NO 76
<211> LENGTH: 246
<212> TYPE: PRT
<213> ORGANISM: Homo sapiens

<400> SEQUENCE: 76

```
Met Thr Arg Val Val Gly Gly Leu Val Ala Leu Arg Gly Ala His Pro
1               5                  10                  15

Tyr Ile Ala Ala Leu Tyr Trp Gly His Ser Phe Cys Ala Gly Ser Leu
            20                  25                  30

Ile Ala Pro Cys Trp Val Leu Thr Ala Ala His Cys Leu Gln Asp Arg
        35                  40                  45

Pro Ala Pro Glu Asp Leu Thr Val Val Leu Gly Gln Glu Arg Arg Asn
    50                  55                  60

His Ser Cys Glu Pro Cys Gln Thr Leu Ala Val Arg Ser Tyr Arg Leu
65                  70                  75                  80

His Glu Ala Phe Ser Pro Val Ser Tyr Gln His Asp Leu Ala Leu Leu
                85                  90                  95

Arg Leu Gln Glu Asp Ala Asp Gly Ser Cys Ala Leu Leu Ser Pro Tyr
            100                 105                 110

Val Gln Pro Val Cys Leu Pro Ser Gly Ala Ala Arg Pro Ser Glu Thr
        115                 120                 125

Thr Leu Cys Gln Val Ala Gly Trp Gly His Gln Phe Glu Gly Ala Glu
    130                 135                 140

Glu Tyr Ala Ser Phe Leu Gln Glu Ala Gln Val Pro Phe Leu Ser Leu
145                 150                 155                 160

Glu Arg Cys Ser Ala Pro Asp Val His Gly Ser Ser Ile Leu Pro Gly
                165                 170                 175

Met Leu Cys Ala Gly Phe Leu Glu Gly Gly Thr Asp Ala Cys Gln Gly
            180                 185                 190

Asp Ser Gly Gly Pro Leu Val Cys Glu Asp Gln Ala Ala Glu Arg Arg
        195                 200                 205

Leu Thr Leu Gln Gly Ile Ile Ser Trp Gly Ser Gly Cys Gly Asp Arg
    210                 215                 220

Asn Lys Pro Gly Val Tyr Thr Asp Val Ala Tyr Tyr Leu Ala Trp Ile
225                 230                 235                 240

Arg Glu His Thr Val Ser
                245
```

<210> SEQ ID NO 77
<211> LENGTH: 741
<212> TYPE: DNA
<213> ORGANISM: Homo sapiens

<400> SEQUENCE: 77

```
atgacccgcg tcgttggcgg gctggtggcg ctacgcgggg cgcacccta  catcgccgcg    60 ctgtactggg gccacagttt ctgcgccggc agcctcatcg cccctgctg  ggtgctgacg   120 gccgctcact gcctgcagga ccggcccgca cccgaggatc tgacggtggt gctcggccag   180
gaacgccgta accacagctg tgagccgtgc cagacgttgg ccgtgcgctc ctaccgcttg   240
cacgaggcct tctcgcccgt cagctaccag cacgacctgg ctctgttgcg ccttcaggag   300
```

```
gatgcggacg gcagctgcgc gctcctgtcg ccttacgttc agccggtgtg cctgccaagc    360
ggcgccgcgc gaccctccga gaccacgctc tgccaggtgg ccggctgggg ccaccagttc    420 gaggggggcgg aggaatatgc cagcttcctg caggaggcgc aggtaccgtt cctctccctg    480
gagcgctgct cagccccgga cgtgcacgga tcctccatcc tccccggcat gctctgcgca    540
gggttcctcg agggcggcac cgatgcgtgc cagggtgatt ccggaggccc gctggtgtgt    600
gaggaccaag ctgcagagcg ccggctcacc ctgcaaggca tcatcagctg gggatcgggc    660
tgtggtgacc gcaacaagcc aggcgtctac accgatgtgg cctactacct ggcctggatc    720
cgggagcaca ccgtttcctg a                                              741

<210> SEQ ID NO 78
<211> LENGTH: 70
<212> TYPE: PRT
<213> ORGANISM: Homo sapiens

<400> SEQUENCE: 78

Met Leu Cys Ala Gly Phe Leu Glu Gly Gly Thr Asp Ala Cys Gln Gly
1               5                   10                  15

Asp Ser Gly Gly Pro Leu Val Cys Glu Asp Gln Ala Ala Glu Arg Arg
            20                  25                  30

Leu Thr Leu Gln Gly Ile Ile Ser Trp Gly Ser Gly Cys Gly Asp Arg
        35                  40                  45

Asn Lys Pro Gly Val Tyr Thr Asp Val Ala Tyr Tyr Leu Ala Trp Ile
    50                  55                  60

Arg Glu His Thr Val Ser
65                  70

<210> SEQ ID NO 79
<211> LENGTH: 213
<212> TYPE: DNA
<213> ORGANISM: Homo sapiens

<400> SEQUENCE: 79
atgctctgcg cagggttcct cgagggcggc accgatgcgt gccagggtga ttccggaggc     60
ccgctggtgt gtgaggacca agctgcagag cgccggctca ccctgcaagg catcatcagc    120
tggggatcgg gctgtggtga ccgcaacaag ccaggcgtct acaccgatgt ggcctactac    180
ctggcctgga tccgggagca caccgtttcc tga                                 213

<210> SEQ ID NO 80
<211> LENGTH: 72
<212> TYPE: RNA
<213> ORGANISM: Artificial Sequence
<220> FEATURE:
<223> OTHER INFORMATION: Synthetic

<400> SEQUENCE: 80
aaacagcaua gcaaguuaaa auaaggcuag uccguuauca acuugaaaaa guggcaccga     60
gucggugcuu uu                                                         72

<210> SEQ ID NO 81
<211> LENGTH: 82
<212> TYPE: RNA
<213> ORGANISM: Artificial Sequence
<220> FEATURE:
<223> OTHER INFORMATION: Synthetic

<400> SEQUENCE: 81
```

```
<210> SEQ ID NO 82
<211> LENGTH: 83
<212> TYPE: RNA
<213> ORGANISM: Artificial Sequence
<220> FEATURE:
<223> OTHER INFORMATION: Synthetic

<400> SEQUENCE: 82
guuggaacca ucaaaacag cauagcaagu uaaaauaagg cuaguccguu aucaacuuga      60
aaaaguggca ccgagucggu gc                                              82

<210> SEQ ID NO 82
<211> LENGTH: 83
<212> TYPE: RNA
<213> ORGANISM: Artificial Sequence
<220> FEATURE:
<223> OTHER INFORMATION: Synthetic

<400> SEQUENCE: 82
guuuuagagc uagaaauagc aaguuaaaau aaggcuaguc cguuaucaac uugaaaagu       60 ggcaccgagu cggugcuuuu uuu                                             83

<210> SEQ ID NO 83
<211> LENGTH: 80
<212> TYPE: RNA
<213> ORGANISM: Artificial Sequence
<220> FEATURE:
<223> OTHER INFORMATION: Synthetic

<400> SEQUENCE: 83 guuuagagc uagaaauagc aaguuaaaau aaggcuaguc cguuaucaac uugaaaagu        60 ggcaccgagu cggugcuuuu                                                 80

<210> SEQ ID NO 84
<211> LENGTH: 92
<212> TYPE: RNA
<213> ORGANISM: Artificial Sequence
<220> FEATURE:
<223> OTHER INFORMATION: Synthetic

<400> SEQUENCE: 84 guuuagagc uaugcuggaa acagcauagc aaguuuaaau aaggcuaguc cguuaucaac       60 uugaaaagu ggcaccgagu cggugcuuuu uu                                    92
```

NON-HUMAN ANIMALS COMPRISING A HUMANIZED COAGULATION FACTOR 12 LOCUS

CROSS-REFERENCE TO RELATED APPLICATIONS

This application claims the benefit of U.S. application No. 62/829,321, filed Apr. 4, 2019, which is herein incorporated by reference in its entirety for all purposes.

REFERENCE TO A SEQUENCE LISTING SUBMITTED AS A TEXT FILE VIA EFS WEB

The Sequence Listing written in file 545993SEQLIST.txt is 121 kilobytes, was created on Apr. 2, 2020, and is hereby incorporated by reference.

BACKGROUND

Coagulation factors, along with platelets, are blood components relevant in the process of hemostasis during vessel injury. It is well-established that these components can be drivers of thrombosis when imbalances occur in regulation (i.e., production and/or activity). Thrombotic diseases were believed to primarily arise from aberrant activation in the extrinsic pathway (via tissue factor), but more recently, preclinical studies with F12-deficient mice and molecules that target activated coagulation factor XII (factor XIIa) suggested that the intrinsic pathway (also known as the contact pathway) of coagulation is also involved. Factor XIIa is central to the contact pathway and can drive coagulation via cleavage of factor XI or can drive inflammation via cleavage of plasma prekallikrein. Thus, inhibition of factor XII activity may lead to reduced thrombotic coagulation and inflammation associated with contact pathway activation.

However, there remains a need for suitable non-human animals providing the true human target or a close approximation of the true human target of human-coagulation-factor-XII-targeting reagents, thereby enabling testing of the efficacy and mode of action of such agents in live animals as well as pharmacokinetic and pharmacodynamics studies.

SUMMARY

Non-human animals comprising a humanized coagulation factor XII (F12) locus are provided, as well as methods of making and using such non-human animals. Non-human animal genomes or cells comprising a humanized coagulation factor XII (F12) locus are also provided, as well as methods of making and using such non-human animal genomes or cells. Also provided are humanized non-human animal F12 genes, nuclease agents and/or targeting vectors for use in humanizing a non-human animal F12 gene, and methods of making and using such humanized F12 genes.

In one aspect, provided are non-human animal genomes, non-human animal cells, or non-human animals comprising a humanized coagulation factor XII (F12) locus. Such non-human animal genomes, non-human animal cells, or non-human animals can comprise in its genome a humanized endogenous F12 locus in which a segment of the endogenous F12 locus has been deleted and replaced with a corresponding human F12 sequence.

In some such non-human animal genomes, non-human animal cells, or non-human animals, the humanized endogenous F12 locus encodes a protein comprising a human coagulation factor XII heavy chain. In some such non-human animal genomes, non-human animal cells, or non-human animals, the humanized endogenous F12 locus encodes a protein comprising a human coagulation factor XII light chain. In some such non-human animal genomes, non-human animal cells, or non-human animals, the humanized endogenous F12 locus encodes a protein comprising a human coagulation factor XII signal peptide.

In some such non-human animal genomes, non-human animal cells, or non-human animals, a region of the endogenous F12 locus comprising both coding sequence and non-coding sequence has been deleted and replaced with a corresponding human F12 sequence comprising both coding sequence and non-coding sequence. In some such non-human animal genomes, non-human animal cells, or non-human animals, the humanized endogenous F12 locus comprises the endogenous F12 promoter, wherein the human F12 sequence is operably linked to the endogenous F12 promoter. In some such non-human animal genomes, non-human animal cells, or non-human animals, at least one intron and at least one exon of the endogenous F12 locus have been deleted and replaced with the corresponding human F12 sequence.

In some such non-human animal genomes, non-human animal cells, or non-human animals, the entire F12 coding sequence of the endogenous F12 locus has been deleted and replaced with the corresponding human F12 sequence. Optionally, the region of the endogenous F12 locus from the start codon to the stop codon has been deleted and replaced with the corresponding human F12 sequence.

In some such non-human animal genomes, non-human animal cells, or non-human animals, the endogenous F12 3' untranslated region has not been deleted and replaced with the corresponding human F12 sequence. In some such non-human animal genomes, non-human animal cells, or non-human animals, the endogenous F12 5' untranslated region has not been deleted and replaced with the corresponding human F12 sequence.

In some such non-human animal genomes, non-human animal cells, or non-human animals, the region of the endogenous F12 locus from the start codon to the stop codon has been deleted and replaced with the corresponding human F12 sequence, and the endogenous F12 promoter has not been deleted and replaced with the corresponding human F12 sequence.

In some such non-human animal genomes, non-human animal cells, or non-human animals, the human F12 sequence at the humanized endogenous F12 locus comprises a sequence at least 90%, 95%, 96%, 97%, 98%, 99%, or 100% identical to the sequence set forth in SEQ ID NO: 31 or 32. In some such non-human animal genomes, non-human animal cells, or non-human animals, the humanized endogenous F12 locus encodes a protein comprising a sequence at least 90%, 95%, 96%, 97%, 98%, 99%, or 100% identical to the sequence set forth in SEQ ID NO: 5 or 46. In some such non-human animal genomes, non-human animal cells, or non-human animals, the humanized endogenous F12 locus comprises a coding sequence comprising a sequence at least 90%, 95%, 96%, 97%, 98%, 99%, or 100% identical to the sequence set forth in SEQ ID NO: 13 or 48. In some such non-human animal genomes, non-human animal cells, or non-human animals, the humanized endogenous F12 locus comprises a sequence at least 90%, 95%, 96%, 97%, 98%, 99%, or 100% identical to the sequence set forth in SEQ ID NO: 17 or 18.

In some such non-human animal genomes, non-human animal cells, or non-human animals, the humanized endogenous F12 locus does not comprise a selection cassette or a reporter gene. In some such non-human animal genomes, non-human animal cells, or non-human animals, the humanized endogenous F12 locus comprises a selection cassette or a reporter gene within an intron of the corresponding human F12 sequence.

In some such non-human animal genomes, non-human animal cells, or non-human animals, the non-human animal is homozygous for the humanized endogenous F12 locus.

In some such non-human animal genomes, non-human animal cells, or non-human animals, the non-human animal comprises the humanized endogenous F12 locus in its germline.

In some such non-human animal genomes, non-human animal cells, or non-human animals, the non-human animal is a mammal. Optionally, the non-human animal is a rat or mouse. Optionally, the non-human animal is a mouse.

In some such non-human animal genomes, non-human animal cells, or non-human animals, the non-human animal expresses a short human coagulation factor XII isoform in the brain. Optionally, the short human coagulation factor XII isoform is encoded by an F12 mRNA detected by probes against exons 11-14 of human F12 but not by probes against exons 1-6 of human F12. Optionally, the short human coagulation factor XII isoform is $FXII_{297-596}$. Optionally, the short human coagulation factor XII isoform is expressed in neurons in the brain. Optionally, the short human coagulation factor XII isoform can be activated by plasma kallikrein and converts pro-HGF to active HGF.

In some such non-human animal genomes, non-human animal cells, or non-human animals, the non-human animal has an activated partial thromboplastin time (aPTT) that is not significantly different from an aPTT in a corresponding wild type non-human animal and/or wherein the non-human animal has a prothrombin time (PT) that is not significantly different from an PT in a corresponding wild type non-human animal.

In some such non-human animal genomes, non-human animal cells, or non-human animals, the non-human has human coagulation factor XII plasma levels of at least about 5 µg/mL.

In some such non-human animal genomes, non-human animal cells, or non-human animals, the region of the endogenous F12 locus from the start codon to the stop codon has been deleted and replaced with the corresponding human F12 sequence, the endogenous F12 promoter has not been deleted and replaced with the corresponding human F12 sequence, and the non-human animal expresses a short human coagulation factor XII isoform in the brain, optionally wherein: (i) the short human coagulation factor XII isoform is encoded by an F12 mRNA detected by probes against exons 11-14 of human F12 but not by probes against exons 1-6 of human F12; and/or (ii) the short human coagulation factor XII isoform is $FXII_{297-596}$; and/or (iii) the short human coagulation factor XII isoform is expressed in neurons in the brain; and/or (iv) the short human coagulation factor XII isoform can be activated by plasma kallikrein and converts pro-HGF to active HGF.

In another aspect, providing are targeting vectors for generating a humanized endogenous F12 locus in which a segment of the endogenous F12 locus has been deleted and replaced with a corresponding human F12 sequence, wherein the targeting vector comprises an insert nucleic acid comprising the corresponding human F12 sequence flanked by a 5' homology arm targeting a 5' target sequence at the endogenous F12 locus and a 3' homology arm targeting a 3' target sequence at the endogenous F12 locus.

In another aspect, provided are humanized non-human animal F12 genes in which a segment of the endogenous F12 locus has been deleted and replaced with a corresponding human F12 sequence.

In another aspect, provided are methods of assessing the activity of a human-coagulation-factor-XII-targeting reagent in vivo. Some such methods comprise: (a) administering the human-coagulation-factor-XII-targeting reagent to any of the non-human animals described above; and (b) assessing the activity of the human-coagulation-factor-XII-targeting reagent in the non-human animal.

In some such methods, the administering comprises adeno-associated virus (AAV)-mediated delivery, lipid nanoparticle (LNP)-mediated delivery, hydrodynamic delivery (HDD), or injection.

In some such methods, step (b) comprises isolating plasma from the non-human animal and assessing activity of the human-coagulation-factor-XII-targeting reagent in the plasma. In some such methods, step (b) comprises assessing the activity of the human-coagulation-factor-XII-targeting reagent in the liver or the brain of the non-human animal. In some such methods, step (b) comprises assessing coagulation or thrombin generation. In some such methods, step (b) comprises assessing HGF-Met signaling. In some such methods, step (b) comprises measuring expression of an F12 messenger RNA encoded by the humanized endogenous F12 locus. In some such methods, step (b) comprises measuring expression of a coagulation factor XII protein encoded by the humanized endogenous coagulation factor XII locus. In some such methods, the human-coagulation-factor-XII-targeting reagent is a genome-editing agent, and step (b) comprises assessing modification of the humanized endogenous F12 locus. In some such methods, step (b) comprises measuring the frequency of insertions or deletions within the humanized endogenous F12 locus.

In some such methods, the human-coagulation-factor-XII-targeting reagent comprises a nuclease agent designed to target a region of a human F12 gene. Optionally, the nuclease agent comprises a Cas protein and a guide RNA designed to target a guide RNA target sequence in the human F12 gene. Optionally, the Cas protein is a Cas9 protein.

In some such methods, the human-coagulation-factor-XII-targeting reagent comprises an exogenous donor nucleic acid, wherein the exogenous donor nucleic acid is designed to target the human F12 gene, and optionally wherein the exogenous donor nucleic acid is delivered via AAV. In some such methods, the human-coagulation-factor-XII-targeting reagent is an RNAi agent or an antisense oligonucleotide. In some such methods, the human-coagulation-factor-XII-targeting reagent is an antigen-binding protein. In some such methods, the human-coagulation-factor-XII-targeting reagent is small molecule.

In another aspect, provided are methods of optimizing the activity of a human-coagulation-factor-XII-targeting reagent in vivo. Some such methods comprise: (I) performing any of the above methods a first time in a first non-human animal comprising in its genome a humanized endogenous F12 locus; (II) changing a variable and performing the method of step (I) a second time with the changed variable in a second non-human animal comprising in its genome a humanized endogenous F12 locus; and (III) comparing the activity of the human-coagulation-factor-XII-targeting reagent in step (I) with the activity of the human-coagulation-factor-XII-targeting reagent in step (II), and selecting the method resulting in the higher activity.

In some such methods, the changed variable in step (II) is the delivery method of introducing the human-coagulationfactor-XII-targeting reagent into the non-human animal. In some such methods, the changed variable in step (II) is the route of administration of introducing the human-coagulation-factor-XII-targeting reagent into the non-human animal. In some such methods, the changed variable in step (II) is the concentration or amount of the human-coagulation-factor-XII-targeting reagent introduced into the non-human animal. In some such methods, the changed variable in step (II) is the form of the human-coagulation-factor-XII-targeting reagent introduced into the non-human animal. In some such methods, the changed variable in step (II) is the human-coagulation-factor-XII-targeting reagent introduced into the non-human animal.

In another aspect, provided are methods making any of the above non-human animals. Some such methods comprise: (a) introducing into a non-human animal embryonic stem (ES) cell: (i) a nuclease agent that targets a target sequence in the endogenous F12 locus; and (ii) a targeting vector comprising a nucleic acid insert comprising the human F12 sequence flanked by a 5' homology arm corresponding to a 5' target sequence in the endogenous F12 locus and a 3' homology arm corresponding to a 3' target sequence in the endogenous F12 locus, wherein the targeting vector recombines with the endogenous F12 locus to produce a genetically modified non-human ES cell comprising in its genome the humanized endogenous F12 locus comprising the human F12 sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the humanized endogenous F12 locus comprising the human F12 sequence. Optionally, the targeting vector is a large targeting vector at least 10 kb in length or in which the sum total of the 5' and 3' homology arms is at least 10 kb in length.

Some such methods comprise: (a) introducing into a non-human animal one-cell stage embryo: (i) a nuclease agent that targets a target sequence in the endogenous F12 locus; and (ii) a targeting vector comprising a nucleic acid insert comprising the human F12 sequence flanked by a 5' homology arm corresponding to a 5' target sequence in the endogenous F12 locus and a 3' homology arm corresponding to a 3' target sequence in the endogenous F12 locus, wherein the targeting vector recombines with the endogenous F12 locus to produce a genetically modified non-human one-cell stage embryo comprising in its genome the humanized endogenous F12 locus comprising the human F12 sequence; (b) gestating the genetically modified non-human animal one-cell stage embryo in a surrogate mother to produce a genetically modified F0 generation non-human animal comprising in its genome the humanized endogenous F12 locus comprising the human F12 sequence.

In some such methods, the nuclease agent comprises a Cas protein and a guide RNA. Optionally, the Cas protein is a Cas9 protein. In some such methods, step (a) further comprises introducing a second guide RNA that targets a second target sequence within the endogenous F12 locus.

Some such methods comprise: (a) introducing into a non-human animal host embryo a genetically modified non-human animal embryonic stem (ES) cell comprising in its genome a humanized endogenous F12 locus in which a segment of the endogenous F12 locus has been deleted and replaced with a corresponding human F12 sequence; and (b) gestating the non-human animal host embryo in a surrogate mother, wherein the surrogate mother produces an F0 progeny genetically modified non-human animal comprising the humanized endogenous F12 locus.

Some such methods comprise: (a) introducing into a non-human animal embryonic stem (ES) cell a targeting vector comprising a nucleic acid insert comprising the human F12 sequence flanked by a 5' homology arm corresponding to a 5' target sequence in the endogenous F12 locus and a 3' homology arm corresponding to a 3' target sequence in the endogenous F12 locus, wherein the targeting vector recombines with the endogenous F12 locus to produce a genetically modified non-human ES cell comprising in its genome the humanized endogenous F12 locus comprising the human F12 sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the humanized endogenous F12 locus comprising the human F12 sequence. Optionally, the targeting vector is a large targeting vector at least 10 kb in length or in which the sum total of the 5' and 3' homology arms is at least 10 kb in length.

Some such methods comprise: (a) introducing into a non-human animal one-cell stage embryo a targeting vector comprising a nucleic acid insert comprising the human F12 sequence flanked by a 5' homology arm corresponding to a 5' target sequence in the endogenous F12 locus and a 3' homology arm corresponding to a 3' target sequence in the endogenous F12 locus, wherein the targeting vector recombines with the endogenous F12 locus to produce a genetically modified non-human one-cell stage embryo comprising in its genome the humanized endogenous F12 locus comprising the human F12 sequence; (b) gestating the genetically modified non-human animal one-cell stage embryo in a surrogate mother to produce a genetically modified F0 generation non-human animal comprising in its genome the humanized endogenous F12 locus comprising the human F12 sequence.

In some such methods, step (a) further comprises introducing a nuclease agent or a nucleic acid encoding the nuclease agent, wherein the nuclease agent targets a target sequence in the endogenous F12 locus. Optionally, the nuclease agent comprises a Cas protein and a guide RNA. Optionally, the Cas protein is a Cas9 protein. Optionally, step (a) further comprises introducing a second guide RNA that targets a second target sequence within the endogenous F12 locus.

In some such methods, the non-human animal is a mouse or a rat. Optionally, the non-human animal is a mouse.

In another aspect, provided are methods assessing expression of a short F12 mRNA isoform in a biological sample. Some such methods comprise: (a) detecting and quantifying RNA transcripts using primers and/or probes against one or more of exons 9-14 of an F12 gene; and (b) detecting and quantifying RNA transcripts using primers and/or probes against one or more of exons 1-6 of the F12 gene wherein the short isoform is detected by primers and/or probes against exons 9-14 but not by primers and/or probes against exons 1-6.

BRIEF DESCRIPTION OF THE FIGURES

FIG. 3 shows an alignment of the human and mouse coagulation factor XII proteins (hF12 and mF12, respectively). The signal peptides are boxed, and the heavy chain and light chain regions are noted.

FIG. 8A is a schematic of UCSC Genome browser analysis showing human and mouse F12 genes and transcripts. Human F12 has a large CpG island consisting of 1364 bases (CpG dinucleotide count=141; 68.9% GC content) spanning exons 8-12 which is lacking in mouse F12, where the CpG island has a much lower CpG count of 19 and consists of 231 bases. GenBank shows 5 human F12 transcripts starting in exon 9, which are absent in mouse F12. Of these 5 transcripts, two are supported by experimental evidence, while three are synthetic. Accession numbers for the F12 transcripts starting in exon 9 are: BC012390, KJ901422, KR710723, KR710724, and BT007350. Data were obtained from the UCSC Genome browser (http://genome.ucsc.edu). The December 2013 (GRCh38/hg38) assembly was used for human data and the December 2011 (GRCm38/mm10) assembly was used for mouse data.

FIGS. 9A-9D show that $FXII_{297-596}$ acquires catalytic activity upon activation by kallikrein and can convert pro-HGF to HGF.

In FIG. 9A, $FXII_{297-596}$ was incubated in the presence of absence of kallikrein (15 nM), and kallikrein activity was inhibited with aprotinin before measuring the activity of $FXII_{297-596}$ with the FXIIa chromogenic substrate S-2302. Signal from $FXII_{297-596}$ pre-incubated with kallikrein is not due to residual kallikrein activity, since no activity is seen in samples where $FXII_{297-596}$ was omitted. Mean±SEM shown.

In FIG. 9B, FXII (1.25 µM) was incubated with cathepsin K (Cath K; 100 nM) or vehicle and the reaction products analyzed by non-reducing SDS-PAGE. FXII cleavage products at ~40 kDa could be due to cleavage between L296 and M297, generating $FXII_{297-596}$. The activity of cathepsin K-cleaved FXII (375 nM FXII, 30 nM cathepsin K) was analyzed by chromogenic substrate assay. Negligible activity was observed for cathepsin K-cleaved FXII in the absence of kallikrein activation, indicating that cathepsin K cleavage alone does not generate active FXII. Cathepsin-cleaved FXII incubated with kallikrein (15 nM) had much higher activity than full length FXII incubated with kallikrein. FXII, kallikrein, and cathepsin K alone had negligible activity. Mean±SEM shown.

In FIG. 9C, pro-HGF 25 µg/mL was cleaved by HGFA, and βFXIIa, but not tPA or thrombin (all at 50 nM).

In FIG. 9D, $FXII_{297-596}$ (225 nM) and FXII (50 nM) were activated with kallikrein (15 nM), and kallikrein activity was inhibited with aprotinin prior to incubation with Pro-HGF (25 µg/mL). Pro-HGF was cleaved by kallikrein-activated $FXII_{297-596}$ and kallikrein-activated FXII (arrows), but not by inactivated kallikrein alone. tPA and HGFA (225 nM) were included as positive and negative controls.

FIG. 10A shows F12 expression in selected human tissues that was obtained from the GTEx portal in December 2018. FIG. 10B shows F12 expression in selected mouse tissues that was obtained from RNAseq analysis of C57BL/6 mouse tissue. The vertical lines across the graph indicate fragments per kilobase of transcript per million mapped reads (FPKM)=1.

DEFINITIONS

Figure 1:
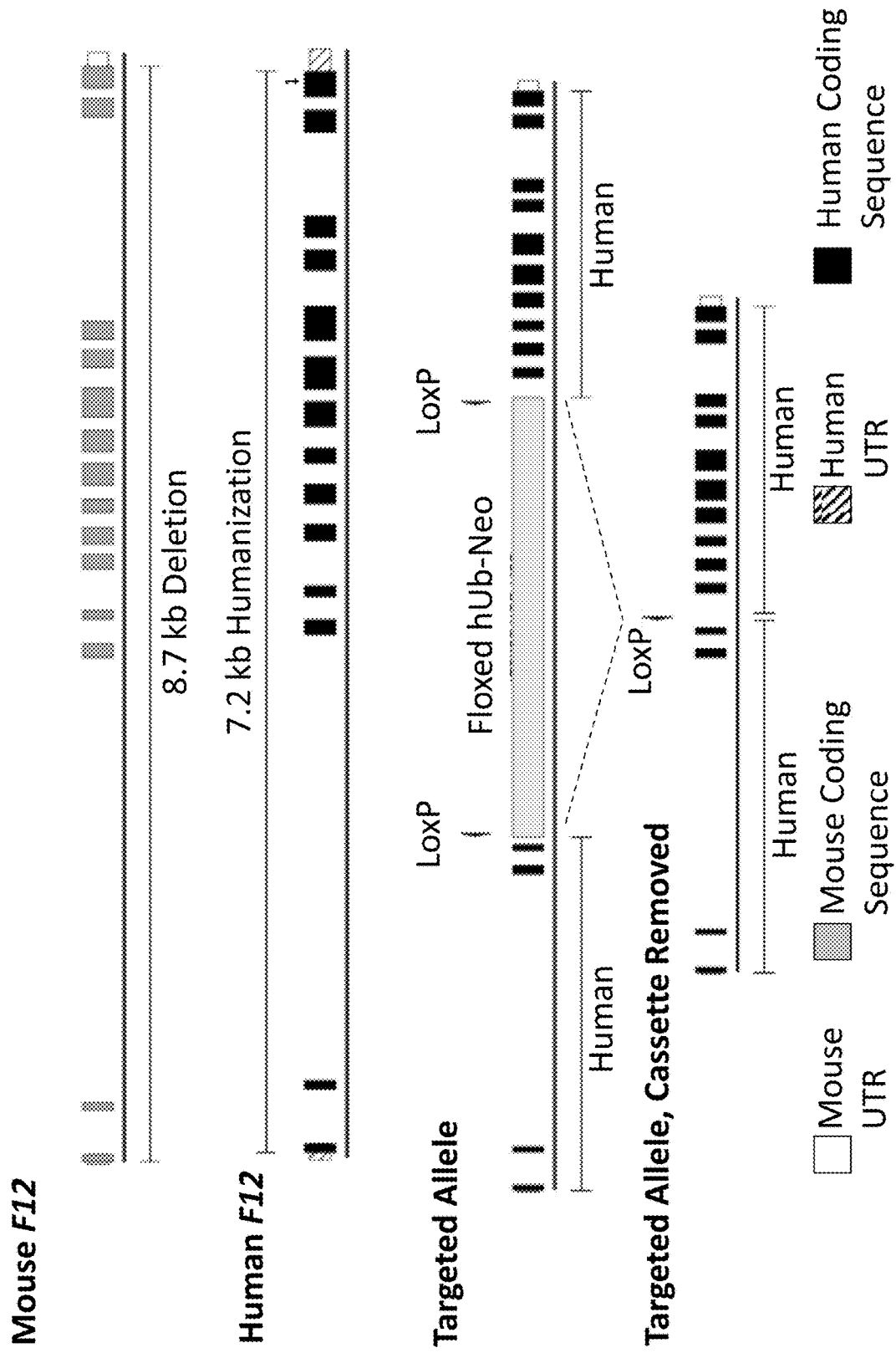
FIG. 1 (not to scale) shows a schematic of the targeting scheme for humanization of the mouse coagulation factor XII (F12) locus. The top portion of the figure shows the endogenous mouse F12 locus and the endogenous human F12 locus, and the bottom portion of the figure shows the humanized locus with or without the self-deleting selection cassette.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to cells, tissues, proteins, and nucleic acids includes cells, tissues, proteins, and nucleic acids that are relatively purified with respect to other bacterial, viral, cellular, or other components that may normally be present in situ, up to and including a substantially pure preparation of the cells, tissues, proteins, and nucleic acids. The term "isolated" also includes cells, tissues, proteins, and nucleic acids that have no naturally occurring counterpart, have been chemically synthesized and are thus substantially uncontaminated by other cells, tissues, proteins, and nucleic acids, or has been separated or purified from most other components (e.g., cellular components) with which they are naturally accompanied (e.g., other cellular proteins, polynucleotides, or cellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous F12 sequence of a non-human animal refers to a native F12 sequence that naturally occurs at the F12 locus in the non-human animal.

"Exogenous" molecules or sequences include molecules or sequences that are not normally present in a cell in that form or location (e.g., genomic locus). Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form and location in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "coagulation factor XII locus" or "F12 locus" may refer to the specific location of an F12 gene, F12 DNA sequence, coagulation-factor-XII-encoding sequence, or F12 position on a chromosome of the genome of an organism that has been identified as to where such a sequence resides. An "F12 locus" may comprise a regulatory element of an F12 gene, including, for example, an enhancer, a promoter, 5' and/or 3' untranslated region (UTR), or a combination thereof.

The term "gene" refers to DNA sequences in a chromosome that may contain, if naturally present, at least one coding and at least one non-coding region. The DNA sequence in a chromosome that codes for a product (e.g., but not limited to, an RNA product and/or a polypeptide product) can include the coding region interrupted with non-coding introns and sequence located adjacent to the coding region on both the 5' and 3' ends such that the gene corresponds to the full-length mRNA (including the 5' and 3' untranslated sequences). Additionally, other non-coding sequences including regulatory sequences (e.g., but not limited to, promoters, enhancers, and transcription factor binding sites), polyadenylation signals, internal ribosome entry sites, silencers, insulating sequence, and matrix attachment regions may be present in a gene. These sequences may be close to the coding region of the gene (e.g., but not limited to, within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1M NaCl solution by using, e.g., Tm=81.5+ 0.41(% G+C), although other known Tm computations take into account nucleic acid structural characteristics.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656, each of which is herein incorporated by reference in its entirety for all purposes) or by using the Gap program (Wisconsin Sequence Analysis Package, Version 8 for Unix, Genetics Computer Group, University Research Park, Madison Wis.), using default settings, which uses the algorithm of Smith and Waterman (1981) *Adv. Appl. Math.* 2:482-489, herein incorporated by reference in its entirety for all purposes.

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original molecule, but with retention of the molecule's basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment," when referring to a protein, means a protein that is shorter or has fewer amino acids than the full-length protein. The term "fragment," when referring to a nucleic acid, means a nucleic acid that is shorter or has fewer nucleotides than the full-length nucleic acid. A fragment can be, for example, when referring to a protein fragment, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A fragment can be, for example, when referring to a nucleic acid fragment, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
| Arginine | Arg | R | Polar | Positive | −4.5 |
| Asparagine | Asn | N | Polar | Neutral | −3.5 |

TABLE 1-continued

Amino Acid Categorizations.

| Aspartic acid | Asp | D | Polar | Negative | −3.5 |
|---|---|---|---|---|---|
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited to, genes encoding beta-galactosidase (lacZ), the bacterial chloramphenicol acetyl-transferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalama1, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) Semin. Cell Dev. Biol. 22(8):886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) Cell 153:910-918; Mandalos et al. (2012) PLoS ONE 7:e45768:1-9; and Wang et al. (2013) Nat. Biotechnol. 31:530-532, each of which is herein incorporated by reference in its entirety for all purposes.

Non-homologous end joining (NHEJ) includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values±5 of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means p≤0.05.

DETAILED DESCRIPTION

I. Overview

Disclosed herein are non-human animal genomes, non-human animal cells, and non-human animals comprising a humanized coagulation factor XII (F12) locus and methods of using such non-human animal cells and non-human animals. Also disclosed herein are humanized non-human animal F12 genes comprising a targeted genetic modification that humanizes the non-human animal F12 genes and nuclease agents and targeting vectors for use in humanizing a non-human animal F12 gene. Non-human animal cells or non-human animals comprising a humanized F12 locus express a human coagulation factor XII protein or a chimeric coagulation factor XII protein comprising one or more fragments of a human coagulation factor XII protein. Such non-human animal cells and non-human animals can be used to assess delivery or efficacy of human-coagulation-factor-XII-targeting agents (e.g., CRISPR/Cas9 genome editing agents or antigen-binding proteins) in vitro, ex vivo, or in vivo and can be used in methods of optimizing the delivery of efficacy of such agents in vitro, ex vivo, or in vivo.

In some of the non-human animal cells and non-human animals disclosed herein, most or all of the human F12 genomic DNA is inserted into the corresponding orthologous non-human animal F12 locus. In some of the non-human animal cells and non-human animals disclosed herein, most or all of the non-human animal F12 genomic DNA is replaced one-for-one with corresponding orthologous human F12 genomic DNA. Compared to non-human animals with cDNA insertions, expression levels should be higher when the intron-exon structure and splicing machinery are maintained because conserved regulator elements are more likely to be left intact, and spliced transcripts that undergo RNA processing are more stable than cDNAs. In contrast, insertion of human F12 cDNA into a non-human animal F12 locus would abolish conserved regulatory elements. Replacing the non-human animal genomic sequence with the corresponding orthologous human genomic sequence or inserting human F12 genomic sequence in the corresponding orthologous non-human F12 locus is more likely to result in faithful expression of the transgene from the endogenous F12 locus. For example, human F12 genomic sequence may have different internal regulatory elements (as compared to mouse F12 genomic sequence) driving expression of a shorter isoform in neurons, a phenotype that is recapitulated in F12 humanized mice. Transgenic non-human animals with transgenic insertion of human-coagulation-factor-XII-coding sequences at a random genomic locus rather than the endogenous non-human-animal F12 locus will also not as accurately reflect the endogenous regulation of F12 expression. A humanized F12 allele resulting from replacing most or all of the non-human animal genomic DNA one-for-one with corresponding orthologous human genomic DNA or inserting human F12 genomic sequence in the corresponding orthologous non-human F12 locus will provide the true human target or a close approximation of the true human target of human-coagulation-factor-XII-targeting reagents (e.g., CRISPR/Cas9 reagents designed to target human F12, or antibodies or small molecules designed to target human coagulation factor XII), thereby enabling testing of the efficacy and mode of action of such agents in live animals as well as pharmacokinetic and pharmacodynamics studies in a setting where the humanized protein and humanized gene are the only versions of coagulation factor XII and F12 present.

II. Non-Human Animals Comprising a Humanized Coagulation Factor XII (F12) Locus

The non-human animal genomes, non-human animal cells, and non-human animals disclosed herein comprise a humanized coagulation factor XII (F12) locus. Cells or non-human animals comprising a humanized F12 locus express a human coagulation factor XII protein or a partially humanized, chimeric coagulation factor XII protein in which one or more fragments of the native coagulation factor XII protein have been replaced with corresponding fragments from human coagulation factor XII.

A. Coagulation Factor XII (F12)

The cells and non-human animals described herein comprise a humanized coagulation factor XII (F12) locus. Coagulation factor XII (also known as Factor XII, FXII, Hageman factor, beta-factor XIIa part 1, beta-factor XIIa part 2, coagulation factor XIIa heavy chain, or coagulation factor XIIa light chain) is encoded by the F12 gene (also known as FXII, HAE3, HAEX, or HAF). Coagulation factor XII is synthesized by hepatocytes in the liver and secreted into the circulation, where it initiates the contact activation system. Although typically thought to be restricted to the circulation, factor XII protein has been found in the brain of Alzheimer's disease and multiple sclerosis patients, and contact system activation has been observed in human brain and cerebrospinal fluid. Coagulation factor XII is a circulating serine protease that initiates the contact activation system. Activation of factor XII on negatively charged surfaces or by plasma kallikrein produces activated factor XII (factor XIIa). Factor XIIa initiates the intrinsic coagulation cascade, which leads to thrombin generation and clot formation. Factor XIIa also converts plasma prekallikrein to kallikrein, which activates the kallikrein-kinin pathway resulting in the release of the vasoactive and proinflammatory peptide bradykinin. In addition to these well-studied functions, factor XIIa has also been shown to activate hepatocyte growth factor (HGF) and the complement system in vitro. Factor XII circulates as a single chain zymogen which, upon cleavage at R353 during activation, becomes an enzymatically active two-chain molecule (αFXIIa). αFXIIa is further processed to βFXIIa, which consists of the light chain containing the catalytic domain, and only a small portion of the heavy chain.

Human F12 maps to 5q35.3 on chromosome 5 (NCBI RefSeq Gene ID 2161; Assembly GRCh38.p12 (GCF_000001405.38); location NC_000005.10 (177402138 . . . 177409576, complement)). The gene has been reported to have 14 exons. The wild type human coagulation factor XII protein has been assigned UniProt accession number P00748. The sequence for one isoform, P00748-1 (identical to NCBI Accession No. NP_000496.2), is set forth in SEQ ID NO: 46. An mRNA (cDNA) encoding this isoform is assigned NCBI Accession No. NM_000505.3 and is set forth in SEQ ID NO: 34. An exemplary coding sequence (CDS) for this isoform is assigned CCDS ID CCDS34302.1 and is set forth in SEQ ID NO: 48. Another exemplary CDS in which position 619 is C in exon 6 (rs17876030; c.619G>C; p.Ala207Pro) is set forth in SEQ ID NO: 13 and encodes the protein set forth in SEQ ID NO: 5. The full-length human coagulation factor XII protein set forth in SEQ ID NO: 5 has 615 amino acids, including a signal peptide (amino acids 1-19), a heavy chain (amino acids 20-372), and a light chain (amino acids 373-615). Similarly, the full-length human coagulation factor XII protein set forth in SEQ ID NO: 46 has 615 amino acids, including a signal peptide (amino acids 1-19), a heavy chain (amino acids 20-372), and a light chain (amino acids 373-615). Delineations between these domains are as designated in UniProt. Reference to human coagulation factor XII or F12 includes the canonical (wild type) forms as well as all allelic forms and isoforms. Any other forms of human coagulation factor XII have amino acids numbered for maximal alignment with the wild type form (SEQ ID NO: 5 or 46), aligned amino acids being designated the same number.

Mouse F12 maps to 13; 13 B1 on chromosome 13 (NCBI RefSeq Gene ID 58992; Assembly GRCm38.p4 (GCF_000001635.24); location NC_000079.6 (55417958 . . . 55426804, complement)). The gene has been reported to have 14 exons. The wild type mouse coagulation factor XII protein has been assigned UniProt accession number Q80YC5. The sequence for mouse coagulation factor XII (identical to NCBI Accession No. NP_067464.2), is set forth in SEQ ID NO: 1. An exemplary mRNA (cDNA) encoding the canonical isoform (SEQ ID NO: 1) is assigned NCBI Accession No. NM_021489.3 and is set forth in SEQ ID NO: 33. An exemplary coding sequence (CDS) (CCDS ID CCDS36675.1) is set forth in SEQ ID NO: 9. The canonical full-length mouse coagulation factor XII protein set forth in SEQ ID NO: 1 has 597 amino acids, including a signal peptide (amino acids 1-19), a heavy chain (amino acids 20-354) and a light chain (amino acids 355-597). Delineations between these domains are as designated in UniProt. Reference to mouse coagulation factor XII or F12 includes the canonical (wild type) forms as well as all allelic forms and isoforms. Any other forms of mouse coagulation factor XII have amino acids numbered for maximal alignment with the wild type form, aligned amino acids being designated the same number.

Coagulation factor XII sequences for many other non-human animals are also known. These include, for example, rat (UniProt accession number D3ZTE0; NCBI RefSeq Gene ID 306761), bovine (UniProt accession number P98140; NCBI RefSeq Gene ID 280789), guinea pig (UniProt accession number Q04962), and pig (UniProt accession number O97507; NCBI RefSeq Gene ID 397474).

B. Humanized F12 Loci

A humanized F12 locus is an F12 locus in which a segment of the endogenous F12 locus has been deleted and replaced with an orthologous human F12 sequence. A humanized F12 locus can be an F12 locus in which the entire F12 gene is replaced with the corresponding orthologous human F12 sequence, or it can be an F12 locus in which only a portion of the F12 gene is replaced with the corresponding orthologous human F12 sequence (i.e., humanized). Alternatively, a humanized F12 locus can be an F12 locus in which a portion of an orthologous human F12 locus is inserted, or it can be an F12 locus in which a portion of the F12 gene is deleted and a portion of the orthologous human F12 locus is inserted. The portion of the orthologous human F12 locus that is inserted can, for example, comprise more of the human F12 locus than is deleted from the endogenous F12 locus. For example, the entire F12 coding sequence at the endogenous F12 locus can be deleted and replaced with the corresponding human F12 sequence. A human F12 sequence corresponding to a particular segment of endogenous F12 sequence refers to the region of human F12 that aligns with the particular segment of endogenous F12 sequence when human F12 and the endogenous F12 are optimally aligned (greatest number of perfectly matched residues). The corresponding orthologous human sequence can comprise, for example, complementary DNA (cDNA) or genomic DNA. Optionally, the corresponding orthologous human F12 sequence is modified to be codon-optimized based on codon usage in the non-human animal. Replaced (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, 3, 4, 5, 6, 7, 8, 9, 10, 11, 12, 13, or all 14 exons of the human F12 gene can be humanized. For example, exons corresponding to all exons (i.e., exons 1-14) of the human F12 gene can be humanized. Likewise, introns corresponding to 1, 2, 3, 4, 5, 6, 7, 8, 9, 10, 11, 12, or all 13 introns of the human F12 gene can be humanized or can remain endogenous. For example, introns corresponding to all of the introns (i.e., introns 1-13) of the human F12 gene can be humanized. Flanking untranslated regions including regulatory sequences can also be humanized or remain endogenous. For example, the 5' untranslated region (UTR), the 3' UTR, or both the 5' UTR and the 3' UTR can be humanized, or the 5' UTR, the 3' UTR, or both the 5' UTR and the 3' UTR can remain endogenous. In a specific example, both the 5' UTR and the 3' UTR remain endogenous. Depending on the extent of replacement by orthologous sequences, regulatory sequences, such as a promoter, can be endogenous or supplied by the replacing human orthologous sequence. For example, the humanized F12 locus can include the endogenous non-human animal F12 promoter (i.e., the human F12 sequence can be operably linked to the endogenous non-human animal promoter).

One or more or all of the regions encoding the signal peptide, the heavy chain, or the light chain can be humanized, or one or more of such regions can remain endogenous. Exemplary coding sequences for a mouse coagulation factor XII signal peptide, heavy chain, and light chain are set forth in SEQ ID NOS: 10-12, respectively. Exemplary coding sequences for a human coagulation factor XII signal peptide, heavy chain, and light chain are set forth in SEQ ID NOS: 14-16, respectively. Another exemplary coding sequence for a human coagulation factor XII heavy chain is set forth in SEQ ID NO: 49.

For example, all or part of the region of the F12 locus encoding the signal peptide can be humanized, and/or all or part of the region of the F12 locus encoding the heavy chain can be humanized, and/or all or part of the region of the F12 locus encoding the light chain can be humanized. Alternatively or additionally, all or part of the region of the F12 locus encoding the signal peptide can remain endogenous, and/or all or part of the region of the F12 locus encoding the heavy chain can remain endogenous, and/or all or part of the region of the F12 locus encoding the light chain can remain endogenous. In one example, all or part of the regions of the F12 locus encoding the signal peptide, heavy chain, and light chain are humanized. Optionally, the CDS of the humanized region of the F12 locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 13 (or degenerates thereof). Optionally, the CDS of the humanized region of the F12 locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 48 (or degenerates thereof). Optionally, the humanized region of the F12 locus comprises a sequence that is at least about 85%, at least about 90%, at least about 95%, at least about 96%, at least about 97%, at least about 98%, at least about 99%, or about 100% identical to SEQ ID NO: 31 and/or 32. Optionally, the humanized F12 locus encodes a protein that comprises, consists essentially of, or consists of a sequence that is at least about 85%, at least about 90%, at least about 95%, at least about 96%, at least about 97%, at least about 98%, at least about 99%, or about 100% identical to SEQ ID NO: 5 or 46. Optionally, the humanized F12 locus comprises, consists essentially of, or consists of a sequence that is at least about 85%, at least about 90%, at least about 95%, at least about 96%, at least about 97%, at least about 98%, at least about 99%, or about 100% identical to SEQ ID NO: 17 or 18. In each case, the humanized coagulation factor XII protein can retain the activity of the native coagulation factor XII protein and/or the human coagulation factor XII protein.

The coagulation factor XII protein encoded by the humanized F12 locus can comprise one or more domains that are from a human coagulation factor XII protein and/or one or more domains that are from an endogenous (i.e., native) coagulation factor XII protein. Exemplary amino acid sequences for a mouse coagulation factor XII signal peptide, heavy chain, and light chain are set forth in SEQ ID NOS: 2-4, respectively. Exemplary amino acid sequences for a human coagulation factor XII signal peptide, heavy chain, and light chain are set forth in SEQ ID NOS: 6-8, respectively. Another exemplary amino acid sequence for a human coagulation factor XII heavy chain is set forth in SEQ ID NO: 47.

The coagulation factor XII protein can comprise one or more or all of a human coagulation factor XII signal peptide, a human coagulation factor XII heavy chain, and a human coagulation factor XII light chain. Alternatively or additionally, the coagulation factor XII protein can comprise one or more domains that are from the endogenous (i.e., native) non-human animal coagulation factor XII protein. For example, the coagulation factor XII protein can comprise a signal peptide from the endogenous (i.e., native) non-human animal coagulation factor XII protein and/or a heavy chain from the endogenous (i.e., native) non-human animal coagulation factor XII protein and/or a light chain from the endogenous (i.e., native) non-human animal coagulation factor XII protein. As one example, the coagulation factor XII protein can comprise a human signal peptide, heavy chain, and light chain.

Domains in a chimeric coagulation factor XII protein that are from a human coagulation factor XII protein can be encoded by a fully humanized sequence (i.e., the entire sequence encoding that domain is replaced with the orthologous human F12 sequence) or can be encoded by a partially humanized sequence (i.e., some of the sequence encoding that domain is replaced with the orthologous human F12 sequence, and the remaining endogenous (i.e., native) sequence encoding that domain encodes the same amino acids as the orthologous human F12 sequence such that the encoded domain is identical to that domain in the human coagulation factor XII protein). Likewise, domains in a chimeric protein that are from the endogenous coagulation factor XII protein cay be encoded by a fully endogenous sequence (i.e., the entire sequence encoding that domain is the endogenous F12 sequence) or can be encoded by a partially humanized sequence (i.e., some of the sequence encoding that domain is replaced with the orthologous human F12 sequence, but the orthologous human F12 sequence encodes the same amino acids as the replaced endogenous F12 sequence such that the encoded domain is identical to that domain in the endogenous coagulation factor XII protein).

As one example, the coagulation factor XII protein encoded by the humanized F12 locus can comprise a human coagulation factor XII signal peptide. Optionally, the human coagulation factor XII signal peptide comprises, consists essentially of, or consists of a sequence that is at least 85%, 90%, 95%, 96%, 97%, 98%, 99%, or 100% identical to SEQ ID NO: 6. Optionally, the coding sequence for the human coagulation factor XII signal peptide comprises, consists essentially of, or consists of a sequence that is at least 85%, 90%, 95%, 96%, 97%, 98%, 99%, or 100% identical to SEQ ID NO: 14. As another example, the coagulation factor XII protein encoded by the humanized F12 locus can comprise a human coagulation factor XII heavy chain. Optionally, the human coagulation factor XII heavy chain comprises, consists essentially of, or consists of a sequence that is at least about 85%, at least about 90%, at least about 95%, at least about 96%, at least about 97%, at least about 98%, at least about 99%, or about 100% identical to SEQ ID NO: 7 or 47. Optionally, the coding sequence for the human coagulation factor XII heavy chain comprises, consists essentially of, or consists of a sequence that is at least about 85%, at least about 90%, at least about 95%, at least about 96%, at least about 97%, at least about 98%, at least about 99%, or about 100% identical to SEQ ID NO: 15 or 49. As another example, the coagulation factor XII protein encoded by the humanized F12 locus can comprise a human light chain. Optionally, the human light chain comprises, consists essentially of, or consists of a sequence that is at least about 85%, at least about 90%, at least about 95%, at least about 96%, at least about 97%, at least about 98%, at least about 99%, or about 100% identical to SEQ ID NO: 8. Optionally, the coding sequence for the human light chain comprises, consists essentially of, or consists of a sequence that is at least about 85%, at least about 90%, at least about 95%, at least about 96%, at least about 97%, at least about 98%, at least about 99%, or about 100% identical to SEQ ID NO: 16. For example, the coagulation factor XII protein encoded by the humanized F12 locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 5 or 46. Optionally, the F12 CDS encoded by the humanized F12 locus can comprise, consist essentially of, or consist of a sequence that is at least about 85%, at least about 90%, at least about 95%, at least about 96%, at least about 97%, at least about 98%, at least about 99%, or about 100% identical to SEQ ID NO: 13 or 48 (or degenerates thereof). In each case, the humanized coagulation factor XII protein can retain the activity of the native coagulation factor XII protein and/or the human coagulation factor XII protein.

Optionally, a humanized F12 locus can comprise other elements. Examples of such elements can include selection cassettes, reporter genes, recombinase recognition sites, or other elements. In one example, an additional element (e.g., a selection cassette) is located an intron of the inserted human sequence at the humanized F12 locus. In another example, an additional element (e.g., a selection cassette) is located 3' of the inserted human sequence at the humanized F12 locus. Alternatively, the humanized F12 locus can lack other elements (e.g., can lack a selection marker or selection cassette). Examples of suitable reporter genes and reporter proteins are disclosed elsewhere herein. Examples of suitable selection markers include neomycin phosphotransferase (neo$_r$), hygromycin B phosphotransferase (hyg$_r$), puromycin-N-acetyltransferase (puro$_r$), blasticidin S deaminase (bsr$_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized F12 locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

One exemplary humanized F12 locus (e.g., a humanized mouse F12 locus) is one in which a region from the start codon through the stop codon is replaced with the corresponding human sequence. See FIG. 1 and SEQ ID NOS: 17 and 18. In one specific example, the human F12 sequence at the humanized endogenous F12 locus comprises a sequence at least about 85%, at least about 90%, at least about 95%, at least about 96%, at least about 97%, at least about 98%, at least about 99%, or about 100% identical to the sequence set forth in SEQ ID NO: 31 or 32. In another specific example, the humanized endogenous F12 locus encodes a protein comprising a sequence at least about 85%, at least about 90%, at least about 95%, at least about 96%, at least about 97%, at least about 98%, at least about 99%, or about 100% identical to the sequence set forth in SEQ ID NO: 5 or 46. In another specific example, the humanized endogenous F12 locus comprises a coding sequence comprising a sequence at least about 85%, at least about 90%, at least about 95%, at least about 96%, at least about 97%, at least about 98%, at least about 99%, or about 100% identical to the sequence set forth in SEQ ID NO: 13 or 48. In another specific example, the humanized endogenous F12 locus comprises a sequence at least about 85%, at least about 90%, at least about 95%, at least about 96%, at least about 97%, at least about 98%, at least about 99%, or about 100% identical to the sequence set forth in SEQ ID NO: 17 or 18.

C. Non-Human Animal Genomes, Non-Human Animal Cells, and Non-Human Animals Comprising a Humanized Coagulation Factor XII (F12) Locus Non-human animal genomes, non-human animal cells, and non-human animals comprising a humanized coagulation factor XII (F12) locus as described elsewhere herein are provided. The genomes, cells, or non-human animals can be male or female. The genomes, cells, or non-human animals can be heterozygous or homozygous for the humanized F12 locus. A diploid organism has two alleles at each genetic locus. Each pair of alleles represents the genotype of a specific genetic locus. Genotypes are described as homozygous if there are two identical alleles at a particular locus and as heterozygous if the two alleles differ. A non-human animal comprising a humanized F12 locus can comprise the humanized endogenous F12 locus in its germline.

The non-human animal genomes or cells provided herein can be, for example, any non-human animal genome or cell comprising an F12 locus or a genomic locus homologous or orthologous to the human F12 locus. The genomes can be from or the cells can be eukaryotic cells, which include, for example, fungal cells (e.g., yeast), plant cells, animal cells, mammalian cells, non-human mammalian cells, and human cells. The term "animal" includes any member of the animal kingdom, including, for example, mammals, fishes, reptiles, amphibians, birds, and worms. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes. Alternatively, the cells can be neuronal cells, such as pyramidal neuronal cells or cortical neuronal cells.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes or neuronal cells.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized F12 locus as described herein can be made by the methods described elsewhere herein. The term "animal" includes any member of the animal kingdom, including, for example, mammals, fishes, reptiles, amphibians, birds, and worms. In a specific example, the non-human animal is a non-human mammal. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 12959/SvEvH, 129S6 (129/SvEvTac), 129S7, 129S8, 129T1, and 129T2. See, e.g., Festing et al. (1999) *Mamm. Genome* 10(8):836, herein incorporated by reference in its entirety for all purposes. Examples of C57BL strains include C57BL/A, C57BL/An, C57BL/GrFa, C57BL/Ka1_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{avl}$ haplotype. Such strains are available from a variety of sources including Harlan Laboratories. The Dark Agouti (DA) rat strain is characterized as having an agouti coat and an $RT1^{avl}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

The non-human animals comprising a humanized F12 locus as described herein can express a short FXII isoform in the brain, such as in neurons in the brain. For example, the short FXII isoform can be encoded by an F12 mRNA detected by probes against exons 11-14 but not by probes against exons 1-6. In a specific example, the short isoform can be $FXII_{297-596}$, a protein containing the proline-rich and catalytic domains of FXII (M297-5596; SEQ ID NO: 74, encoded by SEQ ID NO: 75). The short FXII isoform can, for example, be activated by plasma kallikrein and can, for example, convert pro-HGF to active HGF. The short FXII isoform can also, for example, be activated following cleavage by kallikrein. Activated short FXII isoform can, for example, reciprocally activate prekallikrein to kallikrein. For example, the short FXII isoform can be capable of launching the kallikrein-kinin pathway. For example, short FXII isoform activation can lead to the generation of bradykinin.

The non-human animals comprising a humanized F12 locus as described herein can have activated partial thromboplastin time (aPTT) coagulation times that are not significantly different from aPTT coagulation times in corresponding wild type non-human animals. Likewise, the non-human animals comprising a humanized F12 locus as described herein can have prothrombin time (PT) values that are not significantly different from PT values in corresponding wild type non-human animals.

The non-human animals comprising a humanized F12 locus as described herein can have levels of human coagulation factor XII in the plasma of between about 1 to about 30, between about 1 to about 25, between about 1 to about 20, between about 2 to about 30, between about 2 to about 25, between about 2 to about 20, between about 3 to about 30, between about 3 to about 25, between about 3 to about 20, between about 4 to about 30, between about 4 to about 25, between about 4 to about 20, between about 5 to about 30, between about 5 to about 25, or between about 5 to about 20 µg/mL. For example, the human coagulation factor XII in the non-human animals can be between about 5 to about 18 µg/mL. Alternatively, the non-human animals comprising a humanized F12 locus as described herein can have levels of human coagulation factor XII in the plasma of at least about 1 µg/mL, at least about 2 µg/mL, at least about 3 µg/mL, at least about 4 µg/mL, at least about 5 µg/mL, at least about 6 µg/mL, at least about 7 µg/mL, at least about 8 µg/mL, at least about 9 µg/mL, or at least about 10 µg/mL.

III. Methods of Using Non-Human Animals Comprising a Humanized Coagulation Factor XII (F12) Locus for Assessing Efficacy of Human-Coagulation-Factor-XII-Targeting Reagents In Vivo or Ex Vivo Various methods are provided for using the non-human animals comprising a humanized F12 locus as described elsewhere herein for assessing or optimizing delivery or efficacy of human-coagulation-factor-XII-targeting reagents (e.g., therapeutic molecules or complexes) in vivo or ex vivo. Because the non-human animals comprise a humanized F12 locus, the non-human animals will more accurately reflect the efficacy of a human-coagulation-factor-XII-targeting reagent. Such non-human animals are particularly useful for testing genome-editing reagents designed to target the human F12 gene because the non-human animals disclosed herein comprise humanized endogenous F12 loci rather than transgenic insertions of human F12 sequence at random genomic loci, and the humanized endogenous F12 loci can comprise orthologous human genomic F12 sequence from both coding and non-coding regions rather than an artificial cDNA sequence.

A. Methods of Testing Efficacy of Human-Coagulation-Factor-XII-Targeting Reagents In Vivo or Ex Vivo Various methods are provided for assessing delivery or efficacy of human-coagulation-factor-XII-targeting reagents in vivo using non-human animals comprising a humanized F12 locus as described elsewhere herein. Such methods can comprise: (a) introducing into the non-human animal a human-coagulation-factor-XII-targeting reagent (i.e., administering the human-coagulation-factor-XII-targeting reagent to the non-human animal); and (b) assessing the activity of the human-coagulation-factor-XII-targeting reagent.

The human-coagulation-factor-XII-targeting reagent can be any biological or chemical agent that targets the human F12 locus (the human F12 gene), the human F12 mRNA, or the human coagulation factor XII protein. Examples of human-coagulation-factor-XII-targeting reagents are disclosed elsewhere herein and include, for example, genome-editing agents or antigen-binding proteins. For example, the human-coagulation-factor-XII-targeting reagent can be an F12-targeting nucleic acid (e.g., CRISPR/Cas guide RNAs, short hairpin RNAs (shRNAs), or small interfering RNAs (siRNAs)) or a nucleic acid encoding an F12-targeting protein (e.g., a Cas protein such as Cas9, a ZFN, or a TALEN). Alternatively, the human-F12-targeting reagent can be a coagulation-factor-XII-targeting antibody or antigen-binding protein, or any other large molecule or small molecule that targets human coagulation factor XII. In one example, the human-coagulation-factor-XII-targeting reagent is a genome-editing agent such as a nuclease agent and/or an exogenous donor nucleic acid (e.g., a targeting vector).

Such human-coagulation-factor-XII-targeting reagents can be administered by any delivery method (e.g., AAV, LNP, HDD, or injection) as disclosed in more detail elsewhere herein and by any route of administration. Means of delivering therapeutic complexes and molecules and routes of administration are disclosed in more detail elsewhere herein. In particular methods, the reagents delivered via AAV-mediated delivery. For example, AAV8 can be used to target the liver. In other particular methods, the reagents are delivered by LNP-mediated delivery. In other particular methods, the reagents are delivered by hydrodynamic delivery (HDD). The dose can be any suitable dose. For example, in some methods in which the reagents (e.g., Cas9 mRNA and gRNA) are delivered by LNP-mediated delivery, the dose can be between about 0.01 and about 10 mg/kg, about 0.01 and about 5 mg/kg, between about 0.01 and about 4 mg/kg, between about 0.01 and about 3 mg/kg, between about 0.01 and about 2 mg/kg, between about 0.01 and about 1 mg/kg, between about 0.1 and about 10 mg/kg, between about 0.1 and about 6 mg/kg; between about 0.1 and about 5 mg/kg, between about 0.1 and about 4 mg/kg, between about 0.1 and about 3 mg/kg, between about 0.1 and about 2 mg/kg, between about 0.1 and about 1 mg/kg, between about 0.3 and about 10 mg/kg, between about 0.3 and about 6 mg/kg; between about 0.3 and about 5 mg/kg, between about 0.3 and about 4 mg/kg, between about 0.3 and about 3 mg/kg, between about 0.3 and about 2 mg/kg, between about 0.3 and about 1 mg/kg, about 0.1 mg/kg, about 0.3 mg/kg, about 1 mg/kg, about 2 mg/kg, or about 3 mg/kg. In a specific example, the dose is between about 0.1 and about 6 mg/kg, between about 0.1 and about 3 mg/kg, or between about 0.1 and about 2 mg/kg.

Methods for assessing activity of the human-coagulation-factor-XII-targeting reagent are well-known and are provided elsewhere herein. Assessment of activity can be in any cell type, any tissue type, or any organ type as disclosed elsewhere herein. In some methods, assessment of activity is in plasma. In some methods, assessment of activity is in liver cells. If the coagulation-factor-XII-targeting reagent is a genome editing reagent (e.g., a nuclease agent), such methods can comprise assessing modification of the humanized F12 locus. As one example, the assessing can comprise measuring non-homologous end joining (NHEJ) activity at the humanized F12 locus. This can comprise, for example, measuring the frequency of insertions or deletions within the humanized F12 locus. For example, the assessing can comprise sequencing the humanized F12 locus in one or more cells isolated from the non-human animal (e.g., next-generation sequencing). Assessment can comprise isolating a target organ (e.g., liver) or tissue from the non-human animal and assessing modification of humanized F12 locus in the target organ or tissue. Assessment can also comprise assessing modification of humanized F12 locus in two or more different cell types within the target organ or tissue. Similarly, assessment can comprise isolating a non-target organ or tissue (e.g., two or more non-target organs or tissues) from the non-human animal and assessing modification of humanized F12 locus in the non-target organ or tissue.

Such methods can also comprise measuring expression levels of the mRNA produced by the humanized F12 locus, or by measuring expression levels of the protein encoded by the humanized F12 locus. For example, protein levels can be measured in a particular cell, tissue, or organ type (e.g., liver), or secreted levels can be measured in the plasma or serum. Methods for assessing expression of F12 mRNA or protein expressed from the humanized F12 locus are provided elsewhere herein and are well-known.

As one specific example, if the human-coagulation-factor-XII-targeting reagent is a genome editing reagent (e.g., a nuclease agent), percent editing (e.g., total number of insertions or deletions observed over the total number of sequences read in the PCR reaction from a pool of lysed cells) at the humanized F12 locus can be assessed (e.g., in liver cells).

The various methods provided above for assessing activity in vivo can also be used to assess the activity of human-coagulation-factor-XII-targeting reagents ex vivo as described elsewhere herein.

In some methods, the human-coagulation-factor-XII-targeting reagent is a nuclease agent, such as a CRISPR/Cas nuclease agent, that targets the human F12 gene. Such methods can comprise, for example: (a) introducing into the non-human animal a nuclease agent designed to cleave the human F12 gene (e.g., Cas protein such as Cas9 and a guide RNA designed to target a guide RNA target sequence in the human F12 gene); and (b) assessing modification of the humanized F12 locus.

In the case of a CRISPR/Cas nuclease, for example, modification of the humanized F12 locus will be induced when the guide RNA forms a complex with the Cas protein and directs the Cas protein to the humanized F12 locus, and the Cas/guide RNA complex cleaves the guide RNA target sequence, triggering repair by the cell (e.g., via non-homologous end joining (NHEJ) if no donor sequence is present).

Optionally, two or more guide RNAs can be introduced, each designed to target a different guide RNA target sequence within the human F12 gene. For example, two guide RNAs can be designed to excise a genomic sequence between the two guide RNA target sequences. Modification of the humanized F12 locus will be induced when the first guide RNA forms a complex with the Cas protein and directs the Cas protein to the humanized F12 locus, the second guide RNA forms a complex with the Cas protein and directs the Cas protein to the humanized F12 locus, the first Cas/guide RNA complex cleaves the first guide RNA target sequence, and the second Cas/guide RNA complex cleaves the second guide RNA target sequence, resulting in excision of the intervening sequence.

Additionally or alternatively, an exogenous donor nucleic acid (e.g., targeting vector) capable of recombining with and modifying a human F12 gene is also introduced into the non-human animal. Optionally, the nuclease agent or Cas protein can be tethered to the exogenous donor nucleic acid as described elsewhere herein. Modification of the humanized F12 locus will be induced, for example, when the guide RNA forms a complex with the Cas protein and directs the Cas protein to the humanized F12 locus, the Cas/guide RNA complex cleaves the guide RNA target sequence, and the humanized F12 locus recombines with the exogenous donor nucleic acid to modify the humanized F12 locus. The exogenous donor nucleic acid can recombine with the humanized F12 locus, for example, via homology-directed repair (HDR) or via NHEJ-mediated insertion. Any type of exogenous donor nucleic acid can be used, examples of which are provided elsewhere herein.

B. Methods of Optimizing Delivery or Efficacy of Human-Coagulation-Factor-XII-Targeting Reagent In Vivo or Ex Vivo Various methods are provided for optimizing delivery of human-coagulation-factor-XII-targeting reagents to a cell or non-human animal or optimizing the activity or efficacy of human-coagulation-factor-XII-targeting reagents in vivo. Such methods can comprise, for example: (a) performing the method of testing the efficacy of a human-coagulation-factor-XII-targeting reagents as described above a first time in a first non-human animal or first cell comprising a humanized F12 locus; (b) changing a variable and performing the method a second time in a second non-human animal (i.e., of the same species) or a second cell comprising a humanized F12 locus with the changed variable; and (c) comparing the activity of the human-coagulation-factor-XII-targeting reagents in step (a) with the activity of the human-coagulation-factor-XII-targeting reagents in step (b), and selecting the method resulting in the higher activity.

Methods of measuring delivery, efficacy, or activity of human-coagulation-factor-XII-targeting reagents are disclosed elsewhere herein. For example, such methods can comprise measuring modification of the humanized F12 locus. More effective modification of the humanized F12 locus can mean different things depending on the desired effect within the non-human animal or cell. For example, more effective modification of the humanized F12 locus can mean one or more or all of higher levels of modification, higher precision, higher consistency, or higher specificity.

Higher levels of modification (i.e., higher efficacy) of the humanized F12 locus refers to a higher percentage of cells is targeted within a particular target cell type, within a particular target tissue, or within a particular target organ (e.g., liver). Higher precision refers to more precise modification of the humanized F12 locus (e.g., a higher percentage of targeted cells having the same modification or having the desired modification without extra unintended insertions and deletions (e.g., NHEJ indels)). Higher consistency refers to more consistent modification of the humanized F12 locus among different types of targeted cells, tissues, or organs if more than one type of cell, tissue, or organ is being targeted (e.g., modification of a greater number of cell types within the liver). If a particular organ is being targeted, higher consistency can also refer to more consistent modification throughout all locations within the organ (e.g., the liver). Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

Alternatively, such methods can comprise measuring expression of F12 mRNA or coagulation factor XII protein. In one example, a more effective human-coagulation-factor-XII-targeting agent results in a greater decrease in F12 mRNA or coagulation factor XII protein expression. Alternatively, such methods can comprise measuring coagulation factor XII activity. In one example, a more effective human-coagulation-factor-XII-targeting agent results in a greater decrease in coagulation-factor-XII activity.

The variable that is changed can be any parameter. As one example, the changed variable can be the packaging or the delivery method (e.g., delivery vehicles) by which the human-coagulation-factor-XII-targeting reagent or reagents are introduced into the cell or non-human animal. Examples of delivery methods or delivery vehicles, such as LNP, HDD, and AAV, are disclosed elsewhere herein. For example, the changed variable can be the AAV serotype. Similarly, the administering can comprise LNP-mediated delivery, and the changed variable can be the LNP formulation. As another example, the changed variable can be the route of administration for introduction of the human-coagulation-factor-XII-targeting reagent or reagents into the cell or non-human animal. Examples of routes of administration, such as intravenous, intravitreal, intraparenchymal, and nasal instillation, are disclosed elsewhere herein.

As another example, the changed variable can be the concentration or amount of the human-coagulation-factor-XII-targeting reagent or reagents introduced. As another example, the changed variable can be the concentration or the amount of one human-coagulation-factor-XII-targeting reagent introduced (e.g., guide RNA, Cas protein, exogenous donor nucleic acid, RNAi agent, or ASO) relative to the concentration or the amount another human-coagulation-factor-XII-targeting reagent introduced (e.g., guide RNA, Cas protein, exogenous donor nucleic acid, RNAi agent, or ASO).

As another example, the changed variable can be the timing of introducing the human-coagulation-factor-XII-targeting reagent or reagents relative to the timing of assessing the activity or efficacy of the reagents. As another example, the changed variable can be the number of times or frequency with which the human-coagulation-factor-XII-targeting reagent or reagents are introduced. As another example, the changed variable can be the timing of introduction of one human-coagulation-factor-XII-targeting reagent introduced (e.g., guide RNA, Cas protein, exogenous donor nucleic acid, RNAi agent, or ASO) relative to the timing of introduction of another human-coagulation-factor-XII-targeting reagent introduced (e.g., guide RNA, Cas protein, exogenous donor nucleic acid, RNAi agent, or ASO).

As another example, the changed variable can be the form in which the human-coagulation-factor-XII-targeting reagent or reagents are introduced. For example, a guide RNA can be introduced in the form of DNA or in the form of RNA. A Cas protein (e.g., Cas9) can be introduced in the form of DNA, in the form of RNA, or in the form of a protein (e.g., complexed with a guide RNA). An exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth. Likewise, RNAi agents and ASOs, for example, can comprise various combinations of modifications for stability, to reduce off-target effects, to facilitate delivery, and so forth.

As another example, the changed variable can be the human-coagulation-factor-XII-targeting reagent or reagents that are introduced. For example, if the human-coagulation-factor-XII-targeting reagent comprises a guide RNA, the changed variable can be introducing a different guide RNA with a different sequence (e.g., targeting a different guide RNA target sequence). Similarly, if the human-coagulation-factor-XII-targeting reagent comprises an RNAi agent or an ASO, the changed variable can be introducing a different RNAi agent or ASO with a different sequence. Likewise, if the human-coagulation-factor-XII-targeting reagent comprises a Cas protein, the changed variable can be introducing a different Cas protein (e.g., introducing a different Cas protein with a different sequence, or a nucleic acid with a different sequence (e.g., codon-optimized) but encoding the same Cas protein amino acid sequence. Likewise, if the human-coagulation-factor-XII-targeting reagent comprises an exogenous donor nucleic acid, the changed variable can be introducing a different exogenous donor nucleic acid with a different sequence (e.g., a different insert nucleic acid or different homology arms (e.g., longer or shorter homology arms or homology arms targeting a different region of the human F12 gene)).

In a specific example, the human-coagulation-factor-XII-targeting reagent comprises a Cas protein and a guide RNA designed to target a guide RNA target sequence in a human F12 gene. In such methods, the changed variable can be the guide RNA sequence and/or the guide RNA target sequence. In some such methods, the Cas protein and the guide RNA can each be administered in the form of RNA, and the changed variable can be the ratio of Cas mRNA to guide RNA (e.g., in an LNP formulation). In some such methods, the changed variable can be guide RNA modifications (e.g., a guide RNA with a modification is compared to a guide RNA without the modification).

C. Human-Coagulation-Factor-XII-Targeting Reagents

A human-coagulation-factor-XII-targeting reagent can be any reagent that targets a human F12 gene, a human F12 mRNA, or a human coagulation factor XII protein. For example, it can be a genome-editing reagent such as a nuclease agent that cleaves a target sequence within the human F12 gene and/or an exogenous donor sequence that recombines with a human F12 gene, it can be an antisense oligonucleotide targeting a human F12 mRNA, it can be an antigen-binding protein targeting an epitope of a human coagulation factor XII protein, or it can be a small molecule targeting human coagulation factor XII. Human-coagulation-factor-XII-targeting reagents in the methods disclosed herein can be known human-coagulation-factor-XII-targeting reagents, can be putative human-coagulation-factor-XII-targeting reagents (e.g., candidate reagents designed to target human coagulation factor XII), or can be reagents being screened for human-coagulation-factor-XII-targeting activity.

(1) Nuclease Agents Targeting Human F12 Gene

A human-coagulation-factor-XII-targeting reagent can be a genome editing reagent such as a nuclease agent that cleaves a target sequence within the human F12 gene. A nuclease target sequence includes a DNA sequence at which a nick or double-strand break is induced by a nuclease agent. The target sequence for a nuclease agent can be endogenous (or native) to the cell or the target sequence can be exogenous to the cell. A target sequence that is exogenous to the cell is not naturally occurring in the genome of the cell. The target sequence can also exogenous to the polynucleotides of interest that one desires to be positioned at the target locus. In some cases, the target sequence is present only once in the genome of the host cell.

The length of the target sequence can vary, and includes, for example, target sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break at a desired target sequence can be used in the methods and compositions disclosed herein. A naturally occurring or native nuclease agent can be employed so long as the nuclease agent induces a nick or double-strand break in a desired target sequence. Alternatively, a modified or engineered nuclease agent can be employed. An "engineered nuclease agent" includes a nuclease that is engineered (modified or derived) from its native form to specifically recognize and induce a nick or double-strand break in the desired target sequence. Thus, an engineered nuclease agent can be derived from a native, naturally occurring nuclease agent or it can be artificially created or synthesized. The engineered nuclease can induce a nick or double-strand break in a target sequence, for example, wherein the target sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are well-known. See, e.g., Frendewey et al. (2010) Methods in Enzymology 476:295-307, which is incorporated by reference herein in its entirety for all purposes.

The target sequence of the nuclease agent can be positioned anywhere in or near the F12 locus. The target sequence can be located within a coding region of the F12 gene, or within regulatory regions that influence the expression of the gene. A target sequence of the nuclease agent can be located in an intron, an exon, a promoter, an enhancer, a regulatory region, or any non-protein coding region.

One type of nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) Proc. Natl. Acad. Sci. U.S.A. 107(50):21617-21622; Scholze & Boch (2010) Virulence 1:428-432; Christian et al. Genetics (2010) 186:757-761; Li et al. (2010) Nuc. Acids Res. (2010) 39(1):359-372; and Miller et al. (2011) Nature Biotechnology 29:143-148, each of which is herein incorporated by reference in its entirety.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety. In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TALrepeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2; US20130123484; US20100291048; WO/2011/017293A2; and Gaj et al. (2013) *Trends in Biotechnology*, 31(7):397-405, each of which is herein incorporated by reference.

Another type of nuclease agent is an engineered meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long target sequences, and for tolerating some sequence polymorphisms in their DNA substrates. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples, a naturally occurring variant and/or engineered derivative meganuclease is used. Methods for modifying the kinetics, cofactor interactions, expression, optimal conditions, and/or target sequence specificity, and screening for activity are known. See, e.g., Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346, each of which is herein incorporated by reference in its entirety.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-ScI, F-SceII, F-SuvI, F-TeeI, F-TevI, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can recognize, for example, double-stranded DNA sequences of 12 to 40 base pairs. In some cases, the meganuclease recognizes one perfectly matched target sequence in the genome.

Some meganucleases are homing nucleases. One type of homing nuclease is a LAGLIDADG family of homing nucleases including, for example, I-SceI, I-CreI, and I-DmoI.

Nuclease agents can further comprise CRISPR/Cas systems as described in more detail below.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired target sequence and hence retain nick or double-strand-break-inducing activity. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence.

The nuclease agent may be introduced into a cell or non-human animal by any known means. A polypeptide encoding the nuclease agent may be directly introduced into the cell or non-human animal. Alternatively, a polynucleotide encoding the nuclease agent can be introduced into the cell or non-human animal. When a polynucleotide encoding the nuclease agent is introduced, the nuclease agent can be transiently, conditionally, or constitutively expressed within the cell. The polynucleotide encoding the nuclease agent can be contained in an expression cassette and be operably linked to a conditional promoter, an inducible promoter, a constitutive promoter, or a tissue-specific promoter. Examples of promoters are discussed in further detail elsewhere herein. Alternatively, the nuclease agent can be introduced into the cell as an mRNA encoding the nuclease agent.

A polynucleotide encoding a nuclease agent can be stably integrated in the genome of a cell and operably linked to a promoter active in the cell. Alternatively, a polynucleotide encoding a nuclease agent can be in a targeting vector.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given eukaryotic cell of interest, including a human cell, a non-human cell, a mammalian cell, a rodent cell, a mouse cell, a rat cell or any other host cell of interest, as compared to the naturally occurring polynucleotide sequence.

(2) CRISPR/Cas Systems Targeting Human F12 Gene

A particular type of human-coagulation-factor-XII-targeting reagent can be a Clustered Regularly Interspersed Short Palindromic Repeats (CRISPR)/CRISPR-associated (Cas) system that targets the human F12 gene. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas Proteins and Polynucleotides Encoding Cas Proteins. Cas proteins generally comprise at least one RNA recognition or binding domain that can interact with guide RNAs (gRNAs). Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis*, or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9. Cas9 from *Neisseria meningitidis* (Nme2Cas9) is another exemplary Cas9 protein. See, e.g., Edraki et al. (2019) *Mol. Cell* 73(4):714-726, herein incorporated by reference in its entirety for all purposes. Cas9 proteins from *Streptococcus thermophilus* (e.g., *Streptococcus thermophilus* LMD-9 Cas9 encoded by the CRISPR1 locus (St1Cas9) or *Streptococcus thermophilus* Cas9 from the CRISPR3 locus (St3Cas9)) are other exemplary Cas9 proteins. Cas9 from *Francisella novicida* (FnCas9) or the RHA *Francisella novicida* Cas9 variant that recognizes an alternative PAM (E1369R/E1449H/R1556A substitutions) are other exemplary Cas9 proteins. These and other exemplary Cas9 proteins are reviewed, e.g., in Cebrian-Serrano and Davies (2017) *Mamm. Genome* 28(7):247-261, herein incorporated by reference in its entirety for all purposes. An exemplary Cas9 protein sequence can comprise, consist essentially of, or consist of SEQ ID NO: 35. An exemplary DNA encoding the Cas9 protein can comprise, consist essentially of, or consist of SEQ ID NO: 36.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida*, *Prevotella albensis*, *Lachnospiraceae bacterium* MC2017 1, *Butyrivibrio proteoclasticus*, *Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum*, *Eubacterium eligens*, *Moraxella bovoculi* 237, *Leptospira inadai*, *Lachnospiraceae bacterium* ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A. These and other modified Cas proteins are reviewed, e.g., in Cebrian-Serrano and Davies (2017) *Mamm. Genome* 28(7):247-261, herein incorporated by reference in its entirety for all purposes. Another example of a modified Cas9 protein is xCas9, which is a SpCas9 variant that can recognize an expanded range of PAM sequences. See, e.g., Hu et al. (2018) *Nature* 556:57-63, herein incorporated by reference in its entirety for all purposes.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337(6096): 816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Res.* 39(21):9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of xCas9 are the same as those described above for SpCas9. Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes. Examples of inactivating mutations in the catalytic domains of Nme2Cas9 are also known (e.g., combination of D16A and H588A). Examples of inactivating mutations in the catalytic domains of St1Cas9 are also known (e.g., combination of D9A, D598A, H599A, and N622A). Examples of inactivating mutations in the catalytic domains of St3Cas9 are also known (e.g., combination of D10A and N870A). Examples of inactivating mutations in the catalytic domains of CjCas9 are also known (e.g., combination of D8A and H559A). Examples of inactivating mutations in the catalytic domains of FnCas9 and RHA FnCas9 are also known (e.g., N995A).

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins (e.g., nuclease-active Cas proteins or nuclease-inactive Cas proteins) can also be operably linked to heterologous polypeptides as fusion proteins. For example, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282(8):5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to exogenous donor nucleic acids or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor nucleic acid or labeled nucleic acid can be tethered to the C-terminus, the N-terminus, or to an internal region within the Cas protein. In one example, the exogenous donor nucleic acid or labeled nucleic acid is tethered to the C-terminus or the N-terminus of the Cas protein. Likewise, the Cas protein can be tethered to the 5' end, the 3' end, or to an internal region within the exogenous donor nucleic acid or labeled nucleic acid. That is, the exogenous donor nucleic acid or labeled nucleic acid can be tethered in any orientation and polarity. For example, the Cas protein can be tethered to the 5' end or the 3' end of the exogenous donor nucleic acid or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of a cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

Guide RNAs. A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 37). Any of the DNA-targeting segments disclosed herein can be joined to the 5' end of SEQ ID NO: 37 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGU-CCGUUAUCAACUUGAAAAAGUGGCACC GAGUCG-GUGCUUU (SEQ ID NO: 38). Other examples of tracrRNA sequences comprise, consist essentially of, or consist of (SEQ ID NO: 80)
AAACAGCAUAGCAAGUUAAAAUAAGGCUAGUCCGUUAUCAACUUGAAA AAGUGGCACCGAGUCGGUGCUUUU,
or
(SEQ ID NO: 81)
GUUGGAACCAUUCAAAACAGCAUAGCAAGUUAAAAUAAGGCUAGUCCG

UUAUCAACUUGAAAAAGUGGCACCGAGUCGGUGC.

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339(6121):823-826; Jinek et al. (2012) *Science* 337(6096): 816-821; Hwang et al. (2013) *Nat. Biotechnol.* 31(3):227-229; Jiang et al. (2013) *Nat. Biotechnol.* 31(3):233-239; and Cong et al. (2013) *Science* 339(6121):819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471(7340):602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment joined to a scaffold sequence (i.e., the protein-binding or Cas-binding sequence of the guide RNA). For example, such guide RNAs can have a 5' DNA-targeting segment and a 3' scaffold sequence. Exemplary scaffold sequences comprise, consist essentially of, or consist of: GUUUUAGAGC-UAGAAAUAGCAAGUUAAAAUAAGGCUAGU-CCGUUAUCAACUUGA AAAAGUGGCACCGAGUCGGUGCU (version 1; SEQ ID NO: 39); GUUGGAACCAUUCAAAACAG-CAUAGCAAGUUAAAAUAAGGCUAGU-CCGUUAUCA ACUUGAAAAAGUGGCACCGAGUCG-GUGC (version 2; SEQ ID NO: 40); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 41); and GUUUAAGAGCUAUGCUGGAAACAG- CAUAGCAAGUUUAAAUAAGGCUAGUCCGUU
AUCAACUUGAAAAAGUGGCACCGAGUCGGUGC
(version 4; SEQ ID NO: 42). Other exemplary scaffold sequences comprise, consist essentially of, or consist of:

```
                              (version 5; SEQ ID NO: 82)
GUUUUAGAGCUAGAAAUAGCAAGUUAAAAUAAGGCUAGUCCGUUAUC AACUUGAAAAAGUGGCACCGAGUCGGUGCUUUUUUU;
                              (version 6; SEQ ID NO: 83)
GUUUUAGAGCUAGAAAUAGCAAGUUAAAAUAAGGCUAGUCCGUUAUC AACUUGAAAAAGUGGCACCGAGUCGGUGCUUUU;
or
                              (version 7; SEQ ID NO: 84)
GUUUAAGAGCUAUGCUGGAAACAGCAUAGCAAGUUUAAAUAAGGCUA

GUCCGUUAUCAACUUGAAAAAGUGGCACCGAGUCGGUGC.
```

Guide RNAs targeting any guide RNA target sequence can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of SEQ ID NOS: 39-42 to form a single guide RNA (chimeric guide RNA). Guide RNA versions 1, 2, 3, and 4 as disclosed elsewhere herein refer to DNA-targeting segments (i.e., guide sequences or guides) joined with scaffold versions 1, 2, 3, and 4, respectively. Likewise, any of the DNA-targeting segments disclosed herein can be joined to the 5' end of any one of SEQ ID NOS: 82-84 to form a single guide RNA (chimeric guide RNA). Guide RNA versions 5, 6, and 7 as disclosed elsewhere herein refer to DNA-targeting segments (i.e., guide sequences or guides) joined with scaffold versions 5, 6, and 7, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs. For example, Cas mRNAs can be modified by depletion of uridine using synonymous codons.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Rep.* 22(9):2227-2235, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2'OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) *Nat. Biotech.* 35(12):1179-1187, herein incorporated by reference in its entirety for all purposes. Other examples of modified guide RNAs are provided, e.g., in WO 2018/107028 A1, herein incorporated by reference in its entirety for all purposes. Such chemical modifications can, for example, provide greater stability and protection from exonucleases to guide RNAs, allowing them to persist within cells for longer than unmodified guide RNAs. Such chemical modifications can also, for example, protect against innate intracellular immune responses that can actively degrade RNA or trigger immune cascades that lead to cell death.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis. For example, a guide RNA can be chemically synthesized to include 2'-O-methyl analogs and 3' phosphorothioate internucleotide linkages at the first three 5' and 3' terminal RNA residues.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

Guide RNA Target Sequences. Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CC$N_2$-3', where $N_2$ is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are $GN_{19}NGG$ (SEQ ID NO: 43) or $N_{20}NGG$ (SEQ ID NO: 44). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., $GGN_{20}NGG$; SEQ ID NO: 45) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 43-45, including the 5' G or GG and the 3' GG or NGG. Yet other guide RNA target sequences PAMs can have between 14 and 20 nucleotides in length of SEQ ID NOS: 43-45.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

(3) Exogenous Donor Nucleic Acids Targeting Human F12 Gene

The methods and compositions disclosed herein can utilize exogenous donor nucleic acids to modify the humanized F12 locus following cleavage of the humanized F12 locus with a nuclease agent or independent of cleavage of the humanized F12 locus with a nuclease agent. In such methods using a nuclease agent, the nuclease agent protein cleaves the humanized F12 locus to create a single-strand break (nick) or double-strand break, and the exogenous donor nucleic acid recombines the humanized F12 locus via non-homologous end joining (NHEJ)-mediated ligation or through a homology-directed repair event. Optionally, repair with the exogenous donor nucleic acid removes or disrupts the nuclease target sequence so that alleles that have been targeted cannot be re-targeted by the nuclease agent.

The exogenous donor nucleic acid can target any sequence in the human F12 gene. Some exogenous donor nucleic acids comprise homology arms. Other exogenous donor nucleic acids do not comprise homology arms. The exogenous donor nucleic acids can be capable of insertion into a humanized F12 locus by homology-directed repair, and/or they can be capable of insertion into a humanized F12 locus by non-homologous end joining.

Exogenous donor nucleic acids can comprise deoxyribonucleic acid (DNA) or ribonucleic acid (RNA), they can be single-stranded or double-stranded, and they can be in linear or circular form. For example, an exogenous donor nucleic acid can be a single-stranded oligodeoxynucleotide (ssODN). See, e.g., Yoshimi et al. (2016) *Nat. Commun.* 7:10431, herein incorporated by reference in its entirety for all purposes. Exogenous donor nucleic acids can be naked nucleic acids or can be delivered by viruses, such as AAV. In a specific example, the exogenous donor nucleic acid can be delivered via AAV and can be capable of insertion into a humanized F12 locus by non-homologous end joining (e.g., the exogenous donor nucleic acid can be one that does not comprise homology arms).

An exemplary exogenous donor nucleic acid is between about 50 nucleotides to about 5 kb in length, is between about 50 nucleotides to about 3 kb in length, or is between about 50 to about 1,000 nucleotides in length. Other exemplary exogenous donor nucleic acids are between about 40 to about 200 nucleotides in length. For example, an exogenous donor nucleic acid can be between about 50-60, 60-70, 70-80, 80-90, 90-100, 100-110, 110-120, 120-130, 130-140, 140-150, 150-160, 160-170, 170-180, 180-190, or 190-200 nucleotides in length. Alternatively, an exogenous donor nucleic acid can be between about 50-100, 100-200, 200-300, 300-400, 400-500, 500-600, 600-700, 700-800, 800-900, or 900-1000 nucleotides in length. Alternatively, an exogenous donor nucleic acid can be between about 1-1.5, 1.5-2, 2-2.5, 2.5-3, 3-3.5, 3.5-4, 4-4.5, or 4.5-5 kb in length. Alternatively, an exogenous donor nucleic acid can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. Exogenous donor nucleic acids (e.g., targeting vectors) can also be longer.

In one example, an exogenous donor nucleic acid is an ssODN that is between about 80 nucleotides and about 200 nucleotides in length. In another example, an exogenous donor nucleic acids is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor nucleic acids can include modifications or sequences that provide for additional desirable features (e.g., modified or regulated stability; tracking or detecting with a fluorescent label; a binding site for a protein or protein complex; and so forth). Exogenous donor nucleic acids can comprise one or more fluorescent labels, purification tags, epitope tags, or a combination thereof. For example, an exogenous donor nucleic acid can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5- (and -6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor nucleic acid that has been directly integrated into a cleaved target nucleic acid having protruding ends compatible with the ends of the exogenous donor nucleic acid. The label or tag can be at the 5' end, the 3' end, or internally within the exogenous donor nucleic acid. For example, an exogenous donor nucleic acid can be conjugated at 5' end with the IR700 fluorophore from Integrated DNA Technologies (5'IRDYE®700).

Exogenous donor nucleic acids can also comprise nucleic acid inserts including segments of DNA to be integrated at the humanized F12 locus. Integration of a nucleic acid insert at a humanized F12 locus can result in addition of a nucleic acid sequence of interest to the humanized F12 locus, deletion of a nucleic acid sequence of interest at the humanized F12 locus, or replacement of a nucleic acid sequence of interest at the humanized F12 locus (i.e., deletion and insertion). Some exogenous donor nucleic acids are designed for insertion of a nucleic acid insert at the humanized F12 locus without any corresponding deletion at the humanized F12 locus. Other exogenous donor nucleic acids are designed to delete a nucleic acid sequence of interest at the humanized F12 locus without any corresponding insertion of a nucleic acid insert. Yet other exogenous donor nucleic acids are designed to delete a nucleic acid sequence of interest at the humanized F12 locus and replace it with a nucleic acid insert.

The nucleic acid insert or the corresponding nucleic acid at the humanized F12 locus being deleted and/or replaced can be various lengths. An exemplary nucleic acid insert or corresponding nucleic acid at the humanized F12 locus being deleted and/or replaced is between about 1 nucleotide to about 5 kb in length or is between about 1 nucleotide to about 1,000 nucleotides in length. For example, a nucleic acid insert or a corresponding nucleic acid at the humanized F12 locus being deleted and/or replaced can be between about 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-120 nucleotides in length. Likewise, a nucleic acid insert or a corresponding nucleic acid at the humanized F12 locus being deleted and/or replaced can be between 1-100, 100-200, 200-300, 300-400, 400-500, 500-600, 600-700, 700-800, 800-900, or 900-1000 nucleotides in length. Likewise, a nucleic acid insert or a corresponding nucleic acid at the humanized F12 locus being deleted and/or replaced can be between about 1-1.5, 1.5-2, 2-2.5, 2.5-3, 3-3.5, 3.5-4, 4-4.5, or 4.5-5 kb in length or longer.

The nucleic acid insert can comprise a sequence that is homologous or orthologous to all or part of sequence targeted for replacement. For example, the nucleic acid insert can comprise a sequence that comprises one or more point mutations (e.g., 1, 2, 3, 4, 5, or more) compared with a sequence targeted for replacement at the humanized F12 locus. Optionally, such point mutations can result in a conservative amino acid substitution (e.g., substitution of aspartic acid [Asp, D] with glutamic acid [Glu, E]) in the encoded polypeptide.

Some exogenous donor nucleic acids can encode an exogenous protein not encoded or expressed by a wild type endogenous F12 locus (e.g., can comprise an insert nucleic acid that encodes an exogenous protein).

Donor Nucleic Acids for Non-Homologous-End-Joining-Mediated Insertion. Some exogenous donor nucleic acids are capable of insertion into a humanized F12 locus by non-homologous end joining. In some cases, such exogenous donor nucleic acids do not comprise homology arms. For example, such exogenous donor nucleic acids can be inserted into a blunt end double-strand break following cleavage with a nuclease agent. In a specific example, the exogenous donor nucleic acid can be delivered via AAV and can be capable of insertion into a humanized F12 locus by non-homologous end joining (e.g., the exogenous donor nucleic acid can be one that does not comprise homology arms).

Other exogenous donor nucleic acids have short single-stranded regions at the 5' end and/or the 3' end that are complementary to one or more overhangs created by nuclease-mediated cleavage at the humanized F12 locus. These overhangs can also be referred to as 5' and 3' homology arms. For example, some exogenous donor nucleic acids have short single-stranded regions at the 5' end and/or the 3' end that are complementary to one or more overhangs created by nuclease-mediated cleavage at 5' and/or 3' target sequences at the humanized F12 locus. Some such exogenous donor nucleic acids have a complementary region only at the 5' end or only at the 3' end. For example, some such exogenous donor nucleic acids have a complementary region only at the 5' end complementary to an overhang created at a 5' target sequence at the humanized F12 locus or only at the 3' end complementary to an overhang created at a 3' target sequence at the humanized F12 locus. Other such exogenous donor nucleic acids have complementary regions at both the 5' and 3' ends. For example, other such exogenous donor nucleic acids have complementary regions at both the 5' and 3' ends e.g., complementary to first and second overhangs, respectively, generated by nuclease-mediated cleavage at the humanized F12 locus. For example, if the exogenous donor nucleic acid is double-stranded, the single-stranded complementary regions can extend from the 5' end of the top strand of the donor nucleic acid and the 5' end of the bottom strand of the donor nucleic acid, creating 5' overhangs on each end. Alternatively, the single-stranded complementary region can extend from the 3' end of the top strand of the donor nucleic acid and from the 3' end of the bottom strand of the template, creating 3' overhangs.

The complementary regions can be of any length sufficient to promote ligation between the exogenous donor nucleic acid and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5-10, 10-20, 20-30, 30-40, 40-50, 50-60, 60-70, 70-80, 80-90, 90-100, 100-110, 110-120, 120-130, 130-140, or 140-150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Preferably, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) Cell 154:1380-1389; Mali et al. (2013) Nat. Biotech. 31:833-838; and Shen et al. (2014) Nat. Methods 11:399-404, each of which is herein incorporated by reference in its entirety for all purposes. In such cases, a double-stranded exogenous donor nucleic acid can be designed with single-stranded complementary regions that are complementary to the overhangs created by the nicks within the first and second guide RNA target sequences and by the nicks within the third and fourth guide RNA target sequences. Such an exogenous donor nucleic acid can then be inserted by non-homologous-end-joining-mediated ligation.

Donor Nucleic Acids for Insertion by Homology-Directed Repair. Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the humanized F12 locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25-30, 30-40, 40-50, 50-60, 60-70, 70-80, 80-90, 90-100, 100-150, 150-200, 200-250, 250-300, 300-350, 350-400, 400-450, or 450-500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

When a nuclease agent is used in combination with an exogenous donor nucleic acid, the 5' and 3' target sequences are preferably located in sufficient proximity to the nuclease cleavage site (e.g., within sufficient proximity to a the nuclease target sequence) so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the targeted locus that correspond to the 5' and 3' homology arms of the exogenous donor nucleic acid are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor nucleic acid can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous donor nucleic acid and the nuclease cleavage site can vary. For example, target sequences can be located 5' to the nuclease cleavage site, target sequences can be located 3' to the nuclease cleavage site, or the target sequences can flank the nuclease cleavage site.

(4) Other Human-Coagulation-Factor-XII-Targeting Reagents

The activity of any other known or putative human-coagulation-factor-XII-targeting reagent can also be assessed using the non-human animals disclosed herein. Similarly, any other molecule can be screened for human-coagulation-factor-XII-targeting activity using the non-human animals disclosed herein.

As one example, a human-coagulation-factor-XII-targeting reagent can be an antigen-binding protein targeting an epitope of a human coagulation factor XII protein. The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes). Other human-coagulation-factor-XII-targeting reagents include small molecules targeting a human coagulation factor XII protein.

Other human-coagulation-factor-XII-targeting reagents can include RNAi agents. An "RNAi agent" is a composition that comprises a small double-stranded RNA or RNA-like (e.g., chemically modified RNA) oligonucleotide molecule capable of facilitating degradation or inhibition of translation of a target RNA, such as messenger RNA (mRNA), in a sequence-specific manner. The oligonucleotide in the RNAi agent is a polymer of linked nucleosides, each of which can be independently modified or unmodified. RNAi agents operate through the RNA interference mechanism (i.e., inducing RNA interference through interaction with the RNA interference pathway machinery (RNA-induced silencing complex or RISC) of mammalian cells). While it is believed that RNAi agents, as that term is used herein, operate primarily through the RNA interference mechanism, the disclosed RNAi agents are not bound by or limited to any particular pathway or mechanism of action. RNAi agents disclosed herein comprise a sense strand and an antisense strand, and include, but are not limited to short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to a sequence (i.e., a succession or order of nucleobases or nucleotides, described with a succession of letters using standard nomenclature) in the target RNA.

Other human-coagulation-factor-XII-targeting reagents can include antisense oligonucleotides (ASOs). Single-stranded ASOs and RNA interference (RNAi) share a fundamental principle in that an oligonucleotide binds a target RNA through Watson-Crick base pairing. Without wishing to be bound by theory, during RNAi, a small RNA duplex (RNAi agent) associates with the RNA-induced silencing complex (RISC), one strand (the passenger strand) is lost, and the remaining strand (the guide strand) cooperates with RISC to bind complementary RNA. Argonaute 2 (Ago2), the catalytic component of the RISC, then cleaves the target RNA. The guide strand is always associated with either the complementary sense strand or a protein (RISC). In contrast, an ASO must survive and function as a single strand. ASOs bind to the target RNA and block ribosomes or other factors, such as splicing factors, from binding the RNA or recruit proteins such as nucleases. Different modifications and target regions are chosen for ASOs based on the desired mechanism of action. A gapmer is an ASO oligonucleotide containing 2-5 chemically modified nucleotides (e.g. LNA or 2'-MOE) on each terminus flanking a central 8-10 base gap of DNA. After binding the target RNA, the DNA-RNA hybrid acts substrate for RNase H.

D. Administering Human-Coagulation-Factor-XII-Targeting Reagents to Non-Human Animals or Cells The methods disclosed herein can comprise introducing into a non-human animal or cell various molecules (e.g., human-coagulation-factor-XII-targeting reagents such as therapeutic molecules or complexes), including nucleic acids, proteins, nucleic-acid-protein complexes, protein complexes, or small molecules. "Introducing" includes presenting to the cell or non-human animal the molecule (e.g., nucleic acid or protein) in such a manner that it gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

In some methods, components of a CRISPR/Cas system are introduced into a non-human animal or cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Molecules (e.g., Cas proteins or guide RNAs or RNAi agents or ASOs) introduced into the non-human animal or cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a molecule (e.g., a nucleic acid or protein) into a cell or non-human animal. Methods for introducing molecules into various cell types are known and include, for example, stable transfection methods, transient transfection methods, and virus-mediated methods.

Transfection protocols as well as protocols for introducing molecules into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, sonoporation, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of molecules (e.g., nucleic acids or proteins) into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, N.Y.: Cold Spring Harbor Laboratory Press); see also Meyer et al. (2010) *Proc. Natl. Acad. Sci. U.S.A.* 107:15022-15026 and Meyer et al. (2012) *Proc. Natl. Acad. Sci. U.S.A.* 109:9354-9359.

Other methods for introducing molecules (e.g., nucleic acid or proteins) into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediate AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) Cell Reports 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. See, e.g., Finn et al. (2018) Cell Reports 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino) propoxy)carbonyl)oxy)hexadecanoyl)oxy)propane-1,3-diyl (9Z,9'Z,12Z,127)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl 4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine di stearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-di stearoylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. See, e.g., Finn et al. (2018) *Cell Reports* 22:1-9, herein incorporated by reference in its entirety for all purposes. The Cas9 mRNA can be in a 1:1 ratio by weight to the guide RNA. Another specific example of a suitable LNP contains Dlin-MC3-DMA (MC3), cholesterol, DSPC, and PEG-DMG in a 50:38.5:10:1.5 molar ratio.

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. The Cas9 mRNA can be in a 1:2 ratio by weight to the guide RNA.

The mode of delivery can be selected to decrease immunogenicity. For example, a Cas protein and a gRNA may be delivered by different modes (e.g., bi-modal delivery). These different modes may confer different pharmacodynamics or pharmacokinetic properties on the subject delivered molecule (e.g., Cas or nucleic acid encoding, gRNA or nucleic acid encoding, or exogenous donor nucleic acid/repair template). For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially-derived Cas enzyme being displayed on the surface of the cell by WIC molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyms or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the exogenous donor nucleic acids, guide RNAs, or Cas proteins (or nucleic acids encoding the guide RNAs or Cas proteins) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Measuring Delivery, Activity, or Efficacy of Human-Coagulation-Factor-XII-Targeting Reagents In Vivo or Ex Vivo The methods disclosed herein can further comprise detecting or measuring activity of human-coagulation-factor-XII-targeting reagents. Measuring the activity of such reagents can comprise, for example, measuring coagulation factor XII expression or activity or predicted activity. For example, the assessment can comprise measuring coagulation or thrombin generation. Alternatively, the assessment can comprise measuring the potential for hepatocyte growth factor (HGF)-tyrosine-protein kinase Met (Met) signaling activity (e.g., in neurons), such as assessing conversion of pro-HGF to active HGF.

As one example, if the human-coagulation-factor-XII-targeting reagent is a genome editing reagent (e.g., CRISPR/Cas designed to target the human F12 locus), the measuring can comprise assessing the humanized F12 locus for modifications.

Various methods can be used to identify cells having a targeted genetic modification. The screening can comprise a quantitative assay for assessing modification-of-allele (MOA) of a parental chromosome. See, e.g., US 2004/0018626; US 2014/0178879; US 2016/0145646; WO 2016/081923; and Frendewey et al. (2010) *Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the humanized F12 locus in a non-human animal can be in any cell type from any tissue or organ. For example, the assessment can be in multiple cell types from the same tissue or organ or in cells from multiple locations within the tissue or organ. This can provide information about which cell types within a target tissue or organ are being targeted or which sections of a tissue or organ are being reached by the human-coagulation-factor-XII-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

If the reagent is designed to inactivate the humanized F12 locus, affect expression of the humanized F12 locus, prevent translation of the humanized F12 mRNA, or clear the humanized coagulation factor XII protein, the measuring can comprise assessing humanized F12 mRNA or protein expression. This measuring can be within particular cell types or organs (e.g., the liver or particular cell types or regions within the liver, or the brain or particular cell types or regions with the brain, such as the hippocampal pyramidal layer (pyramidal neurons) and cortical neurons), or it can involve measuring serum or plasma levels of humanized coagulation factor XII protein.

One example of an assay that can be used are the RNASCOPE™ and BASESCOPE™ RNA in situ hybridization (ISH) assays, which are methods that can quantify cell-specific edited transcripts, including single nucleotide changes, in the context of intact fixed tissue. The BASESCOPE™ RNA ISH assay can complement NGS and qPCR in characterization of gene editing. Whereas NGS/qPCR can provide quantitative average values of wild type and edited sequences, they provide no information on heterogeneity or percentage of edited cells within a tissue. The BASESCOPE™ ISH assay can provide a landscape view of an entire tissue and quantification of wild type versus edited transcripts with single-cell resolution, where the actual number of cells within the target tissue containing the edited mRNA transcript can be quantified. The BASESCOPE™ assay achieves single-molecule RNA detection using paired oligo ("ZZ") probes to amplify signal without non-specific background. However, the BASESCOPE™ probe design and signal amplification system enables single-molecule RNA detection with a ZZ probe and it can differentially detect single nucleotide edits and mutations in intact fixed tissue.

Production and secretion of the humanized coagulation factor XII protein can be assessed by any known means. For example, expression can be assessed by measuring levels of the encoded mRNA or levels of the encoded protein in the non-human animal (e.g., measuring plasma or serum levels) using known assays.

Activity of humanized coagulation factor XII protein can be assessed by any known means. Such assays could include, for example, assessing activation of prekallikrein to kallikrein, assessing activation of FXI, assessing activation of pro-HGF to HGF, or assessing activation of the classical complement pathway.

IV. Methods of Making Non-Human Animals Comprising a Humanized F12 Locus

Various methods are provided for making a non-human animal genome, non-human animal cell, or non-human animal comprising a humanized coagulation factor XII (F12) locus as disclosed elsewhere herein. Likewise, various methods are provided for making a humanized coagulation factor XII (F12) gene or locus or for making a non-human animal genome or non-human animal cell comprising a humanized coagulation factor XII (F12) locus as disclosed elsewhere herein. Any convenient method or protocol for producing a genetically modified organism is suitable for producing such a genetically modified non-human animal. See, e.g., Poueymirou et al. (2007) *Nat. Biotechnol.* 25(1): 91-99; U.S. Pat. Nos. 7,294,754; 7,576,259; 7,659,442; 8,816,150; 9,414,575; 9,730,434; and 10,039,269, each of which is herein incorporated by reference in its entirety for all purposes (describing mouse ES cells and the VELOCI-MOUSE® method for making a genetically modified mouse). See also US 2014/0235933 A1, US 2014/0310828 A1, U.S. Pat. Nos. 10,385,359, and 10,329,582, each of which is herein incorporated by reference in its entirety for all purposes (describing rat ES cells and methods for making a genetically modified rat). See also Cho et al. (2009) *Curr. Protoc. Cell. Biol.* 42:19.11.1-19.11.22 (doi: 10.1002/0471143030.cb1911s42) and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted F12 locus.

For example, the method of producing a non-human animal comprising a humanized F12 locus can comprise: (1) modifying the genome of a pluripotent cell to comprise the humanized F12 locus; (2) identifying or selecting the genetically modified pluripotent cell comprising the humanized F12 locus; (3) introducing the genetically modified pluripotent cell into a non-human animal host embryo; and (4) implanting and gestating the host embryo in a surrogate mother. For example, the method of producing a non-human animal comprising a humanized F12 locus can comprise: (1) providing a pluripotent cell (e.g., an embryonic stem (ES) cell such as a mouse ES cell or a rat ES cell) comprising the humanized F12 locus; (2) introducing the genetically modified pluripotent cell into a non-human animal host embryo; and (3) gestating the host embryo in a surrogate mother.

As another example, the method of producing a non-human animal comprising a humanized F12 locus can comprise: (1) modifying the genome of a pluripotent cell (e.g., an embryonic stem (ES) cell such as a mouse ES cell or a rat ES cell) to comprise the humanized F12 locus; (2) identifying or selecting the genetically modified pluripotent cell comprising the humanized F12 locus; (3) introducing the genetically modified pluripotent cell into a non-human animal host embryo; and (4) gestating the host embryo in a surrogate mother. The donor cell can be introduced into a host embryo at any stage, such as the blastocyst stage or the pre-morula stage (i.e., the 4-cell stage or the 8-cell stage). Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized F12 locus (and capable of transmitting the genetic modification through the germline).

The methods can further comprise identifying a cell or animal having a modified target genomic locus. Various methods can be used to identify cells and animals having a targeted genetic modification.

Alternatively, the method of producing the non-human animals described elsewhere herein can comprise: (1) modifying the genome of a one-cell stage embryo to comprise the humanized F12 locus using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The modified cell or one-cell stage embryo can be generated, for example, through recombination by (a) introducing into the cell one or more exogenous donor nucleic acids (e.g., targeting vectors) comprising an insert nucleic acid flanked, for example, by 5' and 3' homology arms corresponding to 5' and 3' target sites (e.g., target sites flanking the endogenous sequences intended for deletion and replacement with the insert nucleic acid), wherein the insert nucleic acid comprises a human F12 sequence to generate a humanized F12 locus; and (b) identifying at least one cell comprising in its genome the insert nucleic acid integrated at the endogenous F12 locus (i.e., identifying at least one cell comprising the humanized F12 locus). Likewise, a modified non-human animal genome or humanized non-human animal F12 gene can be generated, for example, through recombination by (a) contacting the genome or gene with one or more exogenous donor nucleic acids (e.g., targeting vectors) comprising 5' and 3' homology arms corresponding to 5' and 3' target sites (e.g., target sites flanking the endogenous sequences intended for deletion and replacement with an insert nucleic acid (e.g., comprising a human F12 sequence to generate a humanized F12 locus) flanked by the 5' and 3' homology arms), wherein the exogenous donor nucleic acids are designed for humanization of the endogenous non-human animal F12 locus.

Alternatively, the modified pluripotent cell or one-cell stage embryo can be generated by (a) introducing into the cell: (i) a nuclease agent, wherein the nuclease agent induces a nick or double-strand break at a target site within the endogenous F12 locus; and (ii) one or more exogenous donor nucleic acids (e.g., targeting vectors) comprising an insert nucleic acid flanked by, for example, 5' and 3' homology arms corresponding to 5' and 3' target sites (e.g., target sites flanking the endogenous sequences intended for deletion and replacement with the insert nucleic acid), wherein the insert nucleic acid comprises a human F12 sequence to generate a humanized F12 locus; and (c) identifying at least one cell comprising in its genome the insert nucleic acid integrated at the endogenous F12 locus (i.e., identifying at least one cell comprising the humanized F12 locus). Likewise, a modified non-human animal genome or humanized non-human animal F12 gene can be generated by contacting the genome or gene with: (i) a nuclease agent, wherein the nuclease agent induces a nick or double-strand break at a target site within the endogenous F12 locus or gene; and (ii) one or more exogenous donor nucleic acids (e.g., targeting vectors) comprising an insert nucleic acid (e.g., comprising a human F12 sequence to generate a humanized F12 locus) flanked by, for example, 5' and 3' homology arms corresponding to 5' and 3' target sites (e.g., target sites flanking the endogenous sequences intended for deletion and replacement with the insert nucleic acid), wherein the exogenous donor nucleic acids are designed for humanization of the endogenous F12 locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9). See, e.g., US 2013/0309670 and US 2015/0159175, each of which is herein incorporated by reference in its entirety for all purposes. In one example, the nuclease comprises a Cas9 protein and a guide RNA. In another example, the nuclease comprises a Cas9 protein and two or more, three or more, or four or more guide RNAs.

The step of modifying the genome can, for example, utilize exogenous repair templates or donor nucleic acids (e.g., targeting vectors) to modify an F12 locus to comprise a humanized F12 locus disclosed herein. As one example, the targeting vector can be for generating a humanized F12 gene at an endogenous F12 locus (e.g., endogenous non-human animal F12 locus), wherein the targeting vector comprises a nucleic acid insert comprising human F12 sequence to be integrated in the F12 locus flanked by a 5' homology arm targeting a 5' target sequence at the endogenous F12 locus and a 3' homology arm targeting a 3' target sequence at the endogenous F12 locus. Integration of a nucleic acid insert in the F12 locus can result in addition of a nucleic acid sequence of interest in the F12 locus, deletion of a nucleic acid sequence of interest in the F12 locus, or replacement of a nucleic acid sequence of interest in the F12 locus (i.e., deletion and insertion). The homology arms can flank an insert nucleic acid comprising human F12 sequence to generate the humanized F12 locus (e.g., for deleting a segment of the endogenous F12 locus and replacing with an orthologous human F12 sequence).

The exogenous repair templates or donor nucleic acids can be for non-homologous-end-joining-mediated insertion or homologous recombination. Exogenous repair templates or donor nucleic acids can comprise deoxyribonucleic acid (DNA) or ribonucleic acid (RNA), they can be single-stranded or double-stranded, and they can be in linear or circular form. For example, a repair template can be a single-stranded oligodeoxynucleotide (ssODN).

Exogenous donor nucleic acids can also comprise a heterologous sequence that is not present at an untargeted endogenous F12 locus. For example, an exogenous donor nucleic acids can comprise a selection cassette, such as a selection cassette flanked by recombinase recognition sites.

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the F12 locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. In some targeting vectors, the intended mutation in the endogenous F12 locus is included in an insert nucleic acid flanked by the homology arms.

In cells other than one-cell stage embryos, the exogenous donor nucleic acid can be a "large targeting vector" or "LTVEC," which includes targeting vectors that comprise homology arms that correspond to and are derived from nucleic acid sequences larger than those typically used by other approaches intended to perform homologous recombination in cells. See, e.g., US 2004/0018626; WO 2013/163394; U.S. Pat. Nos. 9,834,786; 10,301,646; WO 2015/088643; U.S. Pat. Nos. 9,228,208; 9,546,384; 10,208,317; and US 2019-0112619, each of which is herein incorporated by reference in its entirety for all purposes. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

The methods can further comprise identifying a cell or animal having a modified target genomic locus. Various methods can be used to identify cells and animals having a targeted genetic modification. The screening step can comprise, for example, a quantitative assay for assessing modification-of-allele (MOA) of a parental chromosome. See, e.g., US 2004/0018626; US 2014/0178879; US 2016/0145646; WO 2016/081923; and Frendewey et al. (2010) *Methods Enzymol.* 476:295-307, each of which is herein incorporated by reference in its entirety for all purposes. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more exogenous donor nucleic acids (e.g., targeting vectors) comprising an insert nucleic acid flanked, for example, by 5' and 3' homology arms corresponding to 5' and 3' target sites, wherein the insert nucleic acid comprises a human F12 sequence to generate a humanized F12 locus; and (b) identifying at least one cell comprising in its genome the insert nucleic acid integrated at the endogenous F12 locus (i.e., identifying at least one cell comprising the humanized F12 locus). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized F12 locus; and (b) identifying at least one cell comprising in its genome the insert nucleic acid integrated at the target genomic locus.

Alternatively, the modified pluripotent cell can be generated by (a) introducing into the cell: (i) a nuclease agent, wherein the nuclease agent induces a nick or double-strand break at a target site within the endogenous F12 locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises a human F12 sequence to generate a humanized F12 locus; and (c) identifying at least one cell comprising in its genome the insert nucleic acid integrated at the endogenous F12 locus (i.e., identifying at least one cell comprising the humanized F12 locus). Alternatively, the modified pluripotent cell can be generated by (a) introducing into the cell: (i) a nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized F12 locus; and (c) identifying at least one cell comprising a modification (e.g., integration of the insert nucleic acid) at the target genomic locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized F12 locus using the methods described above for modifying pluripotent cells; (2) selecting the genetically modified embryo; and (3) implanting and gestating the genetically modified embryo into a surrogate mother. Alternatively, the method of producing the non-human animals described elsewhere herein can comprise: (1) modifying the genome of a one-cell stage embryo to comprise the humanized F12 locus using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized F12 locus. It is recognized that depending on the method used to generate the F0 animal, the number of cells within the F0 animal that have the humanized F12 locus will vary. With mice, for example, the introduction of the donor ES cells into a pre-morula stage embryo from a corresponding organism (e.g., an 8-cell stage mouse embryo) via for example, the VELOCIMOUSE® method allows for a greater percentage of the cell population of the F0 mouse to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized F12 locus or can be homozygous for the humanized F12 locus.

V. Methods of Assessing or Using Short F12 Isoform

Various methods of assessing or using the short coagulation factor XII isoform expressed in human neuronal cells are provided. As described in Example 3, the short FXII isoform can be encoded by an F12 mRNA detected by probes against exons 11-14 but not by probes against exons 1-6. In a specific example, the short isoform can be $FXII_{297}$-1-6, (SEQ ID NO: 74, encoded by SEQ ID NO: 75) a protein containing the proline-rich and catalytic domains of FXII (M297-S596).

The assessing can comprise, for example, measuring expression of the short isoform or measuring activity of the short isoform in a biological sample. Expression of the short isoform can be measured at the mRNA level by using primers and/or probes (e.g., for quantitative PCR) against exon 9, 10, 11, 12, 13, or 14, such as probes against exons 11-14. This can be done in comparison to probes against exons 1, 2, 3, 4, 5, or 6, which will not detect the short isoform. Alternatively, expression of the short isoform may be measured at the mRNA level by using primers and/or probes (e.g., for quantitative PCR) against exon 7, 8, 9, 10, 11, 12, 13, or 14, such as probes against exons 11-14. This can be done in comparison to probes against exons 1, 2, 3, 4, 5, or 6, which will not detect the short isoform. Alternatively, expression of the short isoform can be measured at the mRNA level by using primers and/or probes (e.g., for quantitative PCR) against exon 9, 10, 11, 12, 13, or 14, such as probes against exons 11-14. This can be done in comparison to probes against exons 1, 2, 3, 4, 5, 6, 7, or 8 which may not detect the short isoform. For example, such methods can comprise detecting and quantifying RNA transcripts using primers and/or probes against the exons of an F12 gene as described above. This can comprise, for example, reverse transcription PCR (RT-PCR) or quantitative PCR (e.g., RT-qPCR). In RT-qPCR, RNA transcripts are quantified by reverse transcribing them into cDNA first, and then qPCR is subsequently carried out. As in standard PCR, DNA is amplified by 3 repeating steps: denaturation, annealing and elongation. However, in qPCR, fluorescent labeling enables the collection of data as PCR progresses.

Assessing activity of the short isoform can comprise, e.g., measuring hepatocyte growth factor (HGF)-tyrosine-protein kinase Met (Met) signaling activity (e.g., in neurons), such as assessing conversion of pro-HGF to active HGF. Such assays could also include, for example, assessing activation of prekallikrein to kallikrein, assessing activation of FXI, assessing activation of pro-HGF to HGF, or assessing activation of the classical complement pathway.

The assessing (e.g., measuring expression or activity) can be done in any biological sample, such as any organ, tissue type, or cell type. For example, measuring expression can be done in the brain, such as in neurons (e.g., pyramidal neurons or cortical neurons). The organ, tissue, or cell can be from a human, or it can be from a non-human animal (e.g., a non-human animal with a humanized F12 locus as described in detail elsewhere herein).

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Mouse Coagulation Factor XII Protein (Q80YC5-1; NP_067464.2) |
| 2 | Protein | Mouse Coagulation Factor XII Protein Signal Peptide |
| 3 | Protein | Mouse Coagulation Factor XII Protein Heavy Chain |
| 4 | Protein | Mouse Coagulation Factor XII Protein Light Chain |
| 5 | Protein | Human Coagulation Factor XII Protein |
| 6 | Protein | Human Coagulation Factor XII Protein Signal Peptide |
| 7 | Protein | Human Coagulation Factor XII Protein Heavy Chain |
| 8 | Protein | Human Coagulation Factor XII Protein Light Chain |
| 9 | DNA | Mouse F12 CDS (CCDS36675.1) |
| 10 | DNA | Mouse F22 CDS Signal Peptide |
| 11 | DNA | Mouse F12 CDS Heavy Chain |
| 12 | DNA | Mouse F12 CDS Light Chain |
| 13 | DNA | Human F12 CDS |
| 14 | DNA | Human F12 CDS Signal Peptide |
| 15 | DNA | Human F12 CDS Heavy Chain |
| 16 | DNA | Human F12 CDS Light Chain |
| 17 | DNA | MAID7374 (F12 Humanized Region with Neo Self-Deleting Cassette) |
| 18 | DNA | MAID7375 (F12 Humanized Region without Neo Self-Deleting Cassette) |
| 19 | DNA | 7374hTU Fwd |
| 20 | DNA | 7374hTU Probe |
| 21 | DNA | 7374hTU Rev |
| 22 | DNA | 7374hTD Fwd |
| 23 | DNA | 7374hTD Probe |
| 24 | DNA | 7374hTD Rev |
| 25 | DNA | 7374mTU Fwd |
| 26 | DNA | 7374mTU Probe |
| 27 | DNA | 7374mTU Rev |
| 28 | DNA | 7374mTD Fwd |
| 29 | DNA | 7374mTD Probe |
| 30 | DNA | 7374mTD Rev |
| 31 | DNA | Human F12 Sequence in MAID7374 (Part I) |
| 32 | DNA | Human F12 Sequence in MAID7374 (Part II) |
| 33 | DNA | Mouse F12 mRNA (NM_021489.3) |
| 34 | DNA | Human F12 mRNA (NM_000505.3) |

TABLE 2-continued

Description of Sequences.

| SEQ ID NO | Type | Description |
|---|---|---|
| 35 | Protein | Cas9 |
| 36 | DNA | Cas9 |
| 37 | RNA | crRNA Tail |
| 38 | RNA | tracrRNA |
| 39 | RNA | Guide RNA Scaffold v1 |
| 40 | RNA | Guide RNA Scaffold v2 |
| 41 | RNA | Guide RNA Scaffold v3 |
| 42 | RNA | Guide RNA Scaffold v4 |
| 43 | DNA | Guide RNA Target Sequence Plus PAM v1 |
| 44 | DNA | Guide RNA Target Sequence Plus PAM v2 |
| 45 | DNA | Guide RNA Target Sequence Plus PAM v3 |
| 46 | Protein | Human Coagulation Factor XII Protein (P00748-1; NP_000496.2) |
| 47 | Protein | Human Coagulation Factor XII Protein Heavy Chain v2 |
| 48 | DNA | Human F12 CDS (CCDS34302.1) |
| 49 | DNA | Human F12 CDS Heavy Chain v2 |
| 50 | DNA | F12 Exons 1-2 Fwd |
| 51 | DNA | F12 Exons 3-4 Fwd |
| 52 | DNA | F12 Exons 5-6 Fwd |
| 53 | DNA | F12 Exon 7 Fwd |
| 54 | DNA | F12 Exon 9 Fwd |
| 55 | DNA | F12 Exon 11 Fwd |
| 56 | DNA | F12 Exon 14 Fwd |
| 57 | DNA | GAPDH Fwd |
| 58 | DNA | F12 Exons 1-2 Rev |
| 59 | DNA | F12 Exons 3-4 Rev |
| 60 | DNA | F12 Exons 5-6 Rev |
| 61 | DNA | F12 Exon 7 Rev |
| 62 | DNA | F12 Exon 9 Rev |
| 63 | DNA | F12 Exon 11 Rev |
| 64 | DNA | F12 Exon 14 Rev |
| 65 | DNA | GAPDH Rev |
| 66 | DNA | F12 Exons 1-2 Probe |
| 67 | DNA | F12 Exons 3-4 Probe |
| 68 | DNA | F12 Exons 5-6 Probe |
| 69 | DNA | F12 Exon 7 Probe |
| 70 | DNA | F12 Exon 9 Probe |
| 71 | DNA | F12 Exon 11 Probe |
| 72 | DNA | F12 Exon 14 Probe |
| 73 | DNA | GAPDH Probe |
| 74 | Protein | FXII$_{297-596}$ Protein (ORF1 from Example 3) |
| 75 | DNA | FXII$_{297-596}$ DNA (ORF1 from Example 3) |
| 76 | Protein | FXII$_{351-596}$ Protein (ORF2 from Example 3) |
| 77 | DNA | FXII$_{351-596}$ DNA (ORF2 from Example 3) |
| 78 | Protein | FXII$_{527-596}$ Protein (ORF3 from Example 3) |
| 79 | DNA | FXII$_{527-596}$ DNA (ORF3 from Example 3) |
| 80 | RNA | tracrRNA v2 |
| 81 | RNA | tracrRNA v3 |
| 82 | RNA | Guide RNA Scaffold v5 |
| 83 | RNA | Guide RNA Scaffold v6 |
| 84 | RNA | Guide RNA Scaffold v7 |

EXAMPLES

Example 1. Generation of Mice Comprising a Humanized Coagulation Factor XII (F12) Locus A large targeting vector (LTVEC) comprising a 5' homology arm comprising 62.4 kb of the mouse F12 locus (from genome build GRCm38/mm10) and 3' homology arm comprising 107.2 kb of the mouse F12 locus (from genome build GRCm38/mm10) was generated to replace a region of 8.6 kb (8,670 bp) from the mouse F12 gene with 7.2 kb (7,236 bp) of the corresponding human sequence of F12 (from genome build GRCh38/hg38). Information on mouse and human F12 is provided in Table 3. Information on the LTVEC is provided in Table 4. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

TABLE 3

Mouse and Human Coagulation Factor XII (F12).

| | Official Symbol | NCBI Gene ID | Primary Source | RefSeq mRNA ID | UniProt ID | Genomic Assembly | Location |
|---|---|---|---|---|---|---|---|
| Mouse | F12 | 58992 | MGI:1891012 | NM_021489 | Q80YC5 | GRCm38/mm10 | Chr 13 |
| Human | F12 | 2161 | HGNC:3530 | NM_000505 | P00748 | GRCh38/hg38 | Chr 5 |

TABLE 4

Mouse F12 Humanization Targeting Vector.

| | Genome Build | Start | End | Length (bp) |
|---|---|---|---|---|
| 5' Mouse Arm | GRCm38/mm10 | Chr13: 55,426,769 | Chr13: 55,489,207 | 62,439 |
| Human Insert | GRCh38/hg38 | Chr5: 177,402,292 | Chr5: 177,409,527 | 7,236 |
| 3' Mouse Arm | GRCm38/mm10 | Chr13: 55,310,888 | Chr13: 55,418,098 | 107,211 |

Specifically, a region from the ATG start codon through the stop codon was deleted from the mouse F12 locus. A corresponding region of the human F12 from the ATG start codon to the stop codon was inserted in place of the deleted mouse region. A loxP-mPrm1-Crei-pA-hUb1-em7-Neo-pA-loxP cassette (4,766 bp) was included within human intron 4 (81 bp after exon 4 and 220 bp before exon 5). The human F12 region upstream of the self-deleting cassette included 3,874 bp (human ATG to exon 4, and 81 bp of intron 4), and the human F12 region downstream of the self-deleting cassette included 3,362 bp (220 bp of human intron 4, and exon 5 to the stop codon). This is the MAID 7374 allele. See bottom of FIG. 1. After cassette deletion, loxP and cloning sites remained in human F12 intron 4. This is the MAID 7375 allele.

Sequences for the mouse coagulation factor XII signal peptide, heavy chain, and light chain are set forth in SEQ ID NOS: 2-4, respectively, with the corresponding coding sequences set forth in SEQ ID NOS: 10-12, respectively. Sequences for the human coagulation factor XII signal peptide, heavy chain, and light chain are set forth in SEQ ID NOS: 6-8, respectively, with the corresponding coding sequences set forth in SEQ ID NOS: 14-16, respectively. The expected encoded humanized coagulation factor XII protein is identical to the human coagulation factor XII protein. See FIG. 1. An alignment of the mouse and human coagulation factor XII proteins is provided in FIG. 3. The mouse and human F12 coding sequences are set forth in SEQ ID NOS: 9 and 13, respectively. The mouse and human coagulation factor XII protein sequences are set forth in SEQ ID NOS: 1 and 5, respectively. The sequences for the expected humanized ALB coding sequence and the expected humanized coagulation factor XII protein are set forth in SEQ ID NOS: 13 and 5, respectively.

Figure 2:
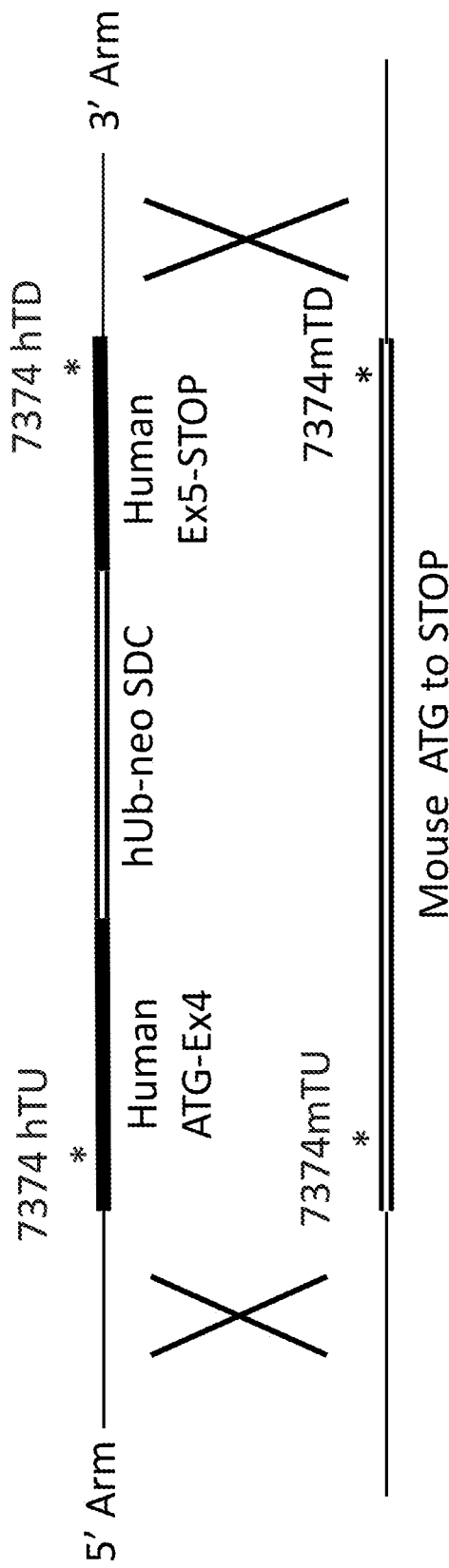
FIG. 2 (not to scale) shows a schematic of the TAQMAN® assays for screening humanization of the mouse F12 locus. Gain-of-allele (GOA) assays include 7374 hU and 7374 hD. Loss-of-allele (LOA) assays include 7374 mTU and 7374 mTD.

To generate the mutant allele, the large targeting vector described above was introduced into F1H4 mouse embryonic stem cells. F1H4 mouse ES cells were derived from hybrid embryos produced by crossing a female C57BL/6NTac mouse to a male 12956/SvEvTac mouse. See, e.g., US 2015-0376651 and WO 2015/200805, each of which is herein incorporated by reference in its entirety for all purposes. Following antibiotic selection, colonies were picked, expanded, and screened by TAQMAN®. See FIG. 2. Loss-of-allele assays were performed to detect loss of the endogenous mouse allele, and gain-of-allele assays were performed to detect gain of the humanized allele using the primers and probes set forth in Table 5.

TABLE 5

Screening Assays.

| Assay | Description | Primer/Probe | Sequence |
|---|---|---|---|
| 7374hTU | Upstream Human Insertion | Fwd | TCGGTGGCAGGCTATGACTTATAG (SEQ ID NO: 19) |
| | | Probe (FAM) | CAGTTCCCTGCCTTCTTCTCTCCC (SEQ ID NO: 20) |
| | | Rev | GGCTTCCCAAGGTGGAATCTAC (SEQ ID NO: 21) |
| 7374hTD | Downstream Human Insertion | Fwd | AAGGGCATGAGTGGGTTTACAAG (SEQ ID NO: 22) |
| | | Probe (Cal) | CGCCTGGAGCAGCTTTGTCCATC (SEQ ID NO: 23) |
| | | Rev | ACACAGAGCGCCTTCTTCACA (SEQ ID NO: 24) |
| 7374mTU | Upstream Mouse LOA | Fwd | GTTCCTGCCTTCTCTCTCCTA (SEQ ID NO: 25) |
| | | Probe (FAM) | TAGGCTCCACCATGGAAAGACTCCA (SEQ ID NO: 26) |
| | | Rev | CCCATCAGGTGCGTCCTTA (SEQ ID NO: 27) |

TABLE 5-continued

Screening Assays.

| Assay | Description | Primer/Probe | Sequence |
|---|---|---|---|
| 7374mTD | Downstream Mouse LOA | Fwd<br>Probe (Cal)<br>Rev | TCGCTGCTCCAACTCTAACG (SEQ ID NO: 28)<br>ACGCCATTCTCCCTGGGATGCTT (SEQ ID NO: 29)<br>ATCGGTGCCTCCCTCCAAGAAG (SEQ ID NO: 30) |

Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) Methods Enzymol. 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

F0 mice were generated from the modified ES cells using the VELOCIMOUSE® method. Specifically, mouse ES cell clones selected by the MOA assay described above were injected into 8-cell stage embryos using the VELOCIMOUSE® method. See, e.g., U.S. Pat. Nos. 7,576,259; 7,659,442; 7,294,754; US 2008/0078000; and Poueymirou et al. (2007) Nat. Biotechnol. 25(1):91-99, each of which is herein incorporated by reference in its entirety for all purposes. In the VELOCIMOUSE® method, targeted mouse embryonic stem (ES) cells are injected through laser-assisted injection into pre-morula stage embryos, e.g., eight-cell-stage embryos, which efficiently yields F0 generation mice that are fully ES-cell-derived.

Figures 4, 5:
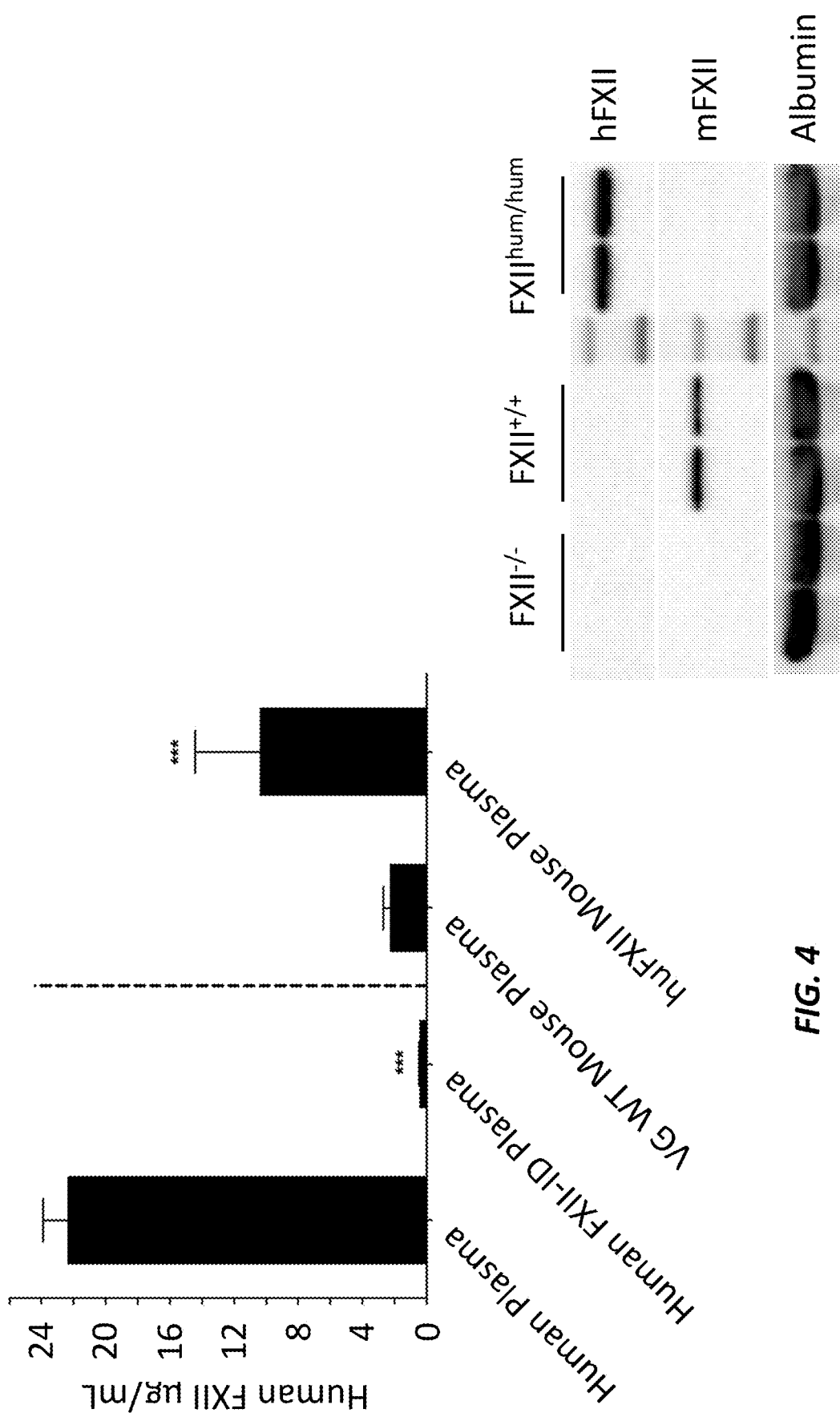
FIG. 4 shows human coagulation factor XII levels in plasma samples from humanized F12 mice and wild type (VG WT) mice. Pooled normal human plasma was used as a positive control, and human FXII-ID (FXII-immunodepleted) plasma was used as a negative control. Student's t-test; *** for p<0.001 vs. normal human plasma for tested human plasma or vs. wild type for mouse plasma.
FIG. 5 shows western blot analysis of plasma samples from wild type mice ($FXII^{+/+}$), F12 knockout mice ($FXII^{-/-}$), and humanized F12 ($FXII^{hum/hum}$) mice. Expression of mouse coagulation factor XII and human coagulation factor XII was measured. Albumin was used as a loading control.

Example 2. Validation of Mice Comprising a Humanized Coagulation Factor XII (F12) Locus To validate the humanized F12 mice, human coagulation factor XII levels were measured in plasma samples from cassette-deleted humanized F12 mice using a human coagulation factor XII ELISA kit (hFXII Total Antigen ELISA kit Molecular Innovations Cat #HFXIIKT-TOT). Human coagulation factor XII was detected at levels of 23.6 µg/mL in normal human plasma and at 5-18 µg/mL in plasma from humanized F12 mice. A small amount was detected in wild type mouse plasma, perhaps due to some minimal cross-reactivity with mouse coagulation factor XII. See FIG. 4.

Western blot analysis (protocol provided in Example 3) of plasma samples was also done to measure mouse coagulation factor XII and human coagulation factor XII expression in wild type mice and humanized F12 mice. Western blot analysis of plasma shows presence of mouse factor XII and lack of human factor XII in wild type ($FXII^{+/+}$) mouse plasma and presence of human factor XII and lack of mouse factor XII in humanized F12 ($FXII^{hum/hum}$) mouse plasma. Neither human nor mouse factor XII was detected in F12 knockout mouse plasma. See FIG. 5.

To further validate the humanized F12 mice, two functional plasma assays were performed: (1) activated partial thromboplastin time (aPTT) and (2) prothrombin time (PT). The aPTT test evaluates all clotting factors of the intrinsic and common pathways of the coagulation cascade by measuring time for a clot to form after the addition of calcium and ellagic acid, whereas the PT test evaluates all clotting factors of the extrinsic and common pathways of the coagulation cascade by measuring time for a clot to form after the addition of calcium and tissue factor.

Figure 6:
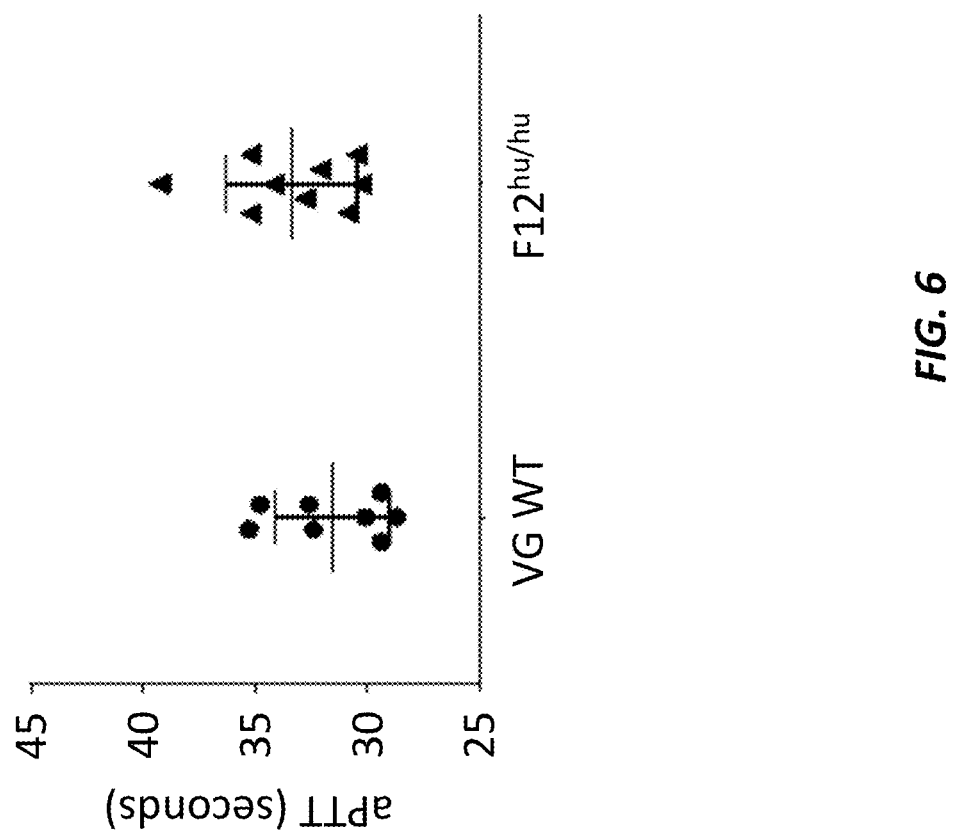
FIG. 6 shows activated partial thromboplastin time (aPTT) results in wild type and humanized F12 mice.

No significant differences were observed in aPTT coagulation times between wild type mice and humanized F12 mice. See FIG. 6. Similarly, PT values were not significantly different between wild type mice and humanized F12 mice, with each having values of 9-11 seconds (data not shown).

Coagulation Assay: PT—Prothrombin Time

This assay is used as a pre-surgical screen to detect potential bleeding problems. It is sensitive to deficiencies in the extrinsic coagulation system (Factor II, V, VII, and X; normal human plasma PT is ~10-13 sec). The instrument used is the Start4 Hemostasis analyzer (Diagnostica Stago). The reagent used is TriniCLOT PT Excel 6 mL (Stago T1106). An exemplary procedure is as follows:

1. Turn on the analyzer. The machine will automatically perform "self-check" and warm up. The assay will be performed only at 37° C.
2. Press the "1" key on the keyboard for the "Test Mode," confirm with the enter key, and press the "1" key for PT test and then confirm with the enter key.
3. Enter the patient ID # or the sample # to display on the working screen.
4. Place cuvette-strips in the incubation area for pre-warming at 37° C.
5. Dispense a ball to each cuvette in the cuvette-strips.
6. Dispense 50 µL of plasma sample (control, patient's or drug treatment sample) in each cuvette (do not generate bubbles).
7. Optionally add 5 µL of 2× serial diluted inhibitors in plasma (only when testing drug dose response) and incubate the mixture at 37° C. for 5 min.
8. Start the timer corresponding to the incubation column (press the timer key) for an incubation of 180 sec. When the instrument beeps, quickly transfer the cuvette-strip to the test-column.
9. Prime the Finnpipette with the start reagents (PT reagent pre-warmed at 37° C.).
10. On the Test-Column, activate the Finnpipette by pressing the pipette control key (the ball starts moving back and forth in the cuvette) and then dispense the pre-warmed 100 µL it of PT reagent to each cuvette.
11. When the clot is formed, the ball will stop moving and the clotting time will be recorded (the result will be printed out after all four clotting times on the same cuvette-strip were done).

Modified aPTT: Activated Partial Thromboplastin Time

This assay is used to detect abnormalities in the intrinsic coagulation system, and sensitive to deficiencies of Factors VIII, IX, X, XI, and XII (aPTT at 28-34 sec in normal human plasma). The instrument used is the Start4 Hemostasis analyzer (Diagnostica Stago, Manual Ref 0931079A). The reagents used are as follows: APTT-XL Ellagic Acid ACTCV 4 mL (Thermo Scientific, Cat #95059-804), $CaCl_2$ 0.02M 10 mL (Thermo Scientific, Cat #95059-808), or TriniCLOT aPTT S 10 mL (Stago T1201). An exemplary procedure is as follows:

1. Turn on the analyzer. The machine will automatically perform "self-check" and warm up. The assay will be performed only at 37° C.
2. Press the "1" key on the keyboard for the "Test Mode," confirm with the enter key, and press the "2" key for APTT test and then confirm with the enter key.
3. Enter the patient ID # or the sample # to display on the working screen.
4. Place cuvette-strips in the incubation area for pre-warming at 37° C.
5. Dispense a ball to each cuvette in the cuvette-strip. There are 4 cuvettes connected on each cuvette-strip.
6. Dispense 50 µL of plasma sample (control, patient's or drug treatment sample) in each cuvette (pipette plasma slowly, do not generate bubbles) and warmed at 37° C. for 1 min.
7. Optionally add 5 µL of 2× serial diluted inhibitors in plasma (only when testing drug dose response) and incubate the mixture at 37° C. for 5 min.
8. Add 50 µL it of trigger (i.e., ellagic acid or Kaolin) to each cuvette.
9. Start the timer corresponding to the incubation column (press the timer key) for an incubation of 300 seconds and then quickly transfer the cuvette-strip to the test-column.
10. Prime the Finnpipette with the start reagents (0.02M of $CaCl_2$ pre-warmed at 37° C.).
11. On the Test-Column, activate the Finnpipette by pressing the pipette control key (the ball starts moving back and forth in the cuvette) and then dispense the pre-warmed 50 µL of $CaCl_2$ to each cuvette.
12. When the clot is formed, the ball will stop moving and the clotting time will be recorded. The result will be printed out automatically after all four cuvettes' clotting times were recorded.

Example 3. Difference in Human vs. Mouse F12 Genomic Sequence May Drive Expression of Human Short Isoform, a Phenotype that is Recapitulated in Humanized F12 Mice Coagulation factor XII (FXII) is synthesized by hepatocytes in the liver and secreted into the circulation, where it initiates the contact activation system. Although typically thought to be restricted to the circulation, FXII protein has been found in the brain of Alzheimer's disease and multiple sclerosis patients, and contact system activation has been observed in human brain and cerebrospinal fluid. However, the source of FXII protein in the brain has not been elucidated and its potential role in the brain is unknown. Using in situ hybridization and RNAseq, we show that a shorter FXII isoform is expressed by neurons in human and FXII humanized mouse brain, with the highest expression observed in pyramidal neurons. This shorter F12 mRNA transcript contains an open reading frame coding for the portion of FXII spanning its proline-rich and catalytic domains. A recombinant version of this shorter FXII protein is activated by plasma kallikrein and converts pro-hepatocyte growth factor (HGF) to active HGF. HGF-Met signaling plays a role in neuronal development and survival, and its dysregulation has been implicated in neurodevelopmental disorders and neurodegeneration. We show here for the first time that a short isoform of F12 mRNA is produced locally in the brain and raise the possibility that brain-derived FXII may be involved in HGF-Met signaling in neurons.

Coagulation factor XII (FXII) is a circulating serine protease that initiates the contact activation system. Activation of FXII on negatively charged surfaces or by plasma kallikrein produces activated FXII (FXIIa). FXIIa initiates the intrinsic coagulation cascade, which leads to thrombin generation and clot formation. FXIIa also converts plasma prekallikrein to kallikrein, which activates the kallikrein-kinin pathway resulting in the release of the vasoactive and proinflammatory peptide bradykinin. In addition to these well-studied functions, FXIIa has also been shown to activate hepatocyte growth factor (HGF) and the complement system in vitro. See, e.g., Shimomura et al. (1995) *Eur. J. Biochem.* 229:257-261, Peek et al. (2002) *J. Biol. Chem.* 277:47804-47809, and Ghebrehiwet et al. (1981) *J. Exp. Med.* 153:665-676, each of which is herein incorporated by reference in its entirety for all purposes. FXII circulates as a single chain zymogen which, upon cleavage at R353 during activation, becomes an enzymatically active two-chain molecule (αFXIIa). αFXIIa is further processed to αFXIIa, which consists of the light chain containing the catalytic domain, and only a small portion of the heavy chain.

FXII is synthesized by hepatocytes in the liver and secreted into the circulation. Although typically thought to be restricted to the circulation, FXII protein has been found colocalized with Aβ plaques in the brain of Alzheimer's disease (AD) patients and in brain lesions of multiple sclerosis (MS) patients. See, e.g., Yasuhara et al. (1994) *Brain Res.* 654:234-240 and Gobel et al. (2016) *Nat. Commun.* 7:11626, each of which is herein incorporated by reference in its entirety for all purposes. Since the blood-brain barrier (BBB) typically prevents movement of circulating proteins into the brain parenchyma, FXII should not enter the healthy human brain. Therefore, FXII observed in the brain of AD and MS patients could be coming from the circulation through a dysfunctional BBB or may be synthesized locally. Whether the source of FXII protein previously found in the brain is peripheral or local has not been well-characterized. See, e.g., Yasuhara et al. (1994) *Brain Res.* 654:234-240 and Gobel et al. (2016) *Nat. Commun.* 7:11626, each of which is herein incorporated by reference in its entirety for all purposes.

FXII in the brain may trigger local activation of the contact system, which has been observed in human brain and cerebrospinal fluid. See, e.g., Ashby et al. (2012) *Neurobiol. Aging* 33:1345-1355 and Bergamaschini et al. (2001) *Mech. Ageing Dev.* 122:1971-1983, each of which is herein incorporated by reference in its entirety for all purposes. Brain FXII could also activate HGF, which plays a role in neuronal development and survival through its receptor Met, or the complement system, which mediates synaptic integrity and plasticity. See, e.g., Kato (2017) *Biomed. Rep.* 7:495-503, Wright and Harding (2015) *J. Alzheimers Dis.* 45:985-1000, and Hammond et al. (2018) *Annu. Rev. Cell Dev. Biol.* 34:523-544, each of which is herein incorporated by reference in its entirety for all purposes. Leakage of FXII from the periphery would likely occur pathologically, while local F12 mRNA synthesis in the brain could be a mechanism for physiological activation of these systems in the brain. Here, we show that a novel F12 mRNA transcript potentially coding for a βFXIIa-like protein is expressed by neurons in the human brain, and that this putative brain FXII protein can be activated by plasma kallikrein and converts pro-HGF to active HGF.

Figure 7A:
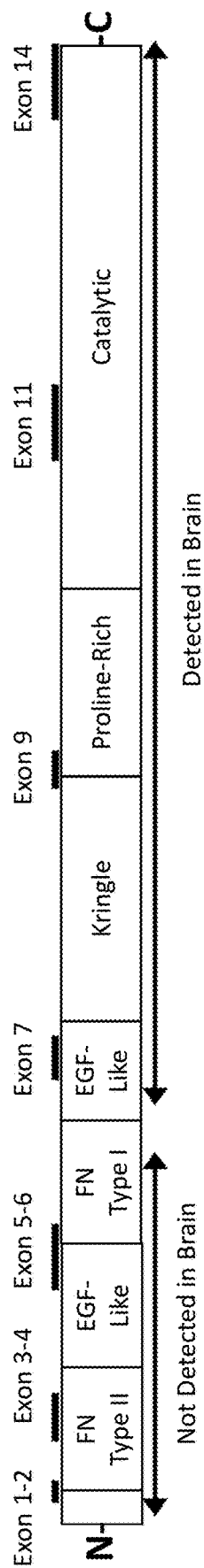
FIG. 7A is a schematic showing localization of qPCR probes relative to FXII protein domains. The line under each probe represents the region of F12 mRNA amplified.
Figure 7B:
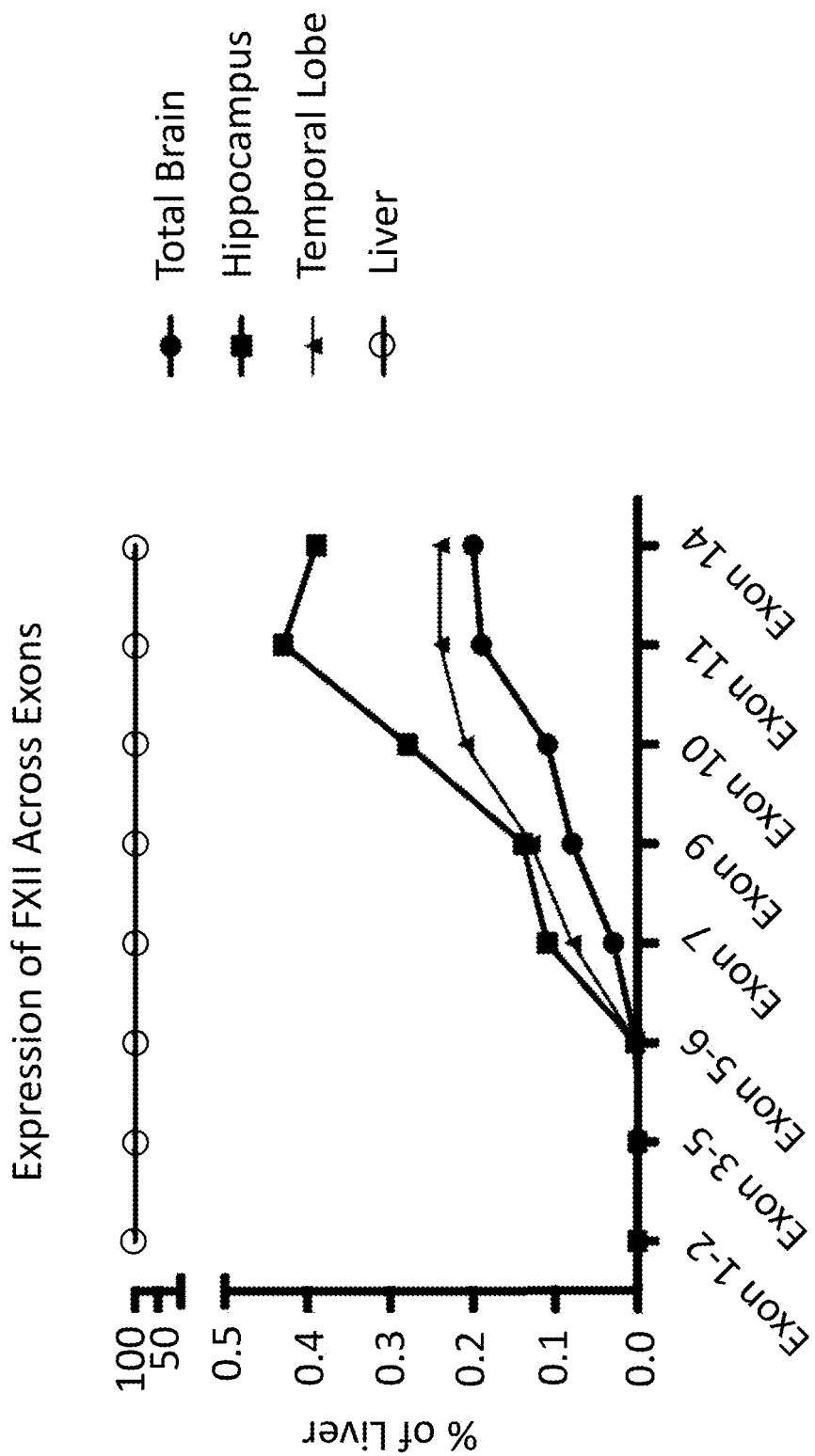
FIG. 7B shows results of qPCR analysis demonstrating expression of all F12 mRNA regions in liver but only expression of exons 7-14 in total brain, hippocampus, and temporal lobe. F12 expression is normalized to GAPDH and plotted as percentage of liver levels.

Published studies show conflicting results regarding the expression of F12 in the brain. One study using PCR primers spanning exons 7-9 detected brain F12 mRNA (Yasuhara et al. (1994) *Brain Res.* 654:234-240, herein incorporated by reference in its entirety for all purposes), while another using primers within exons 3-5 showed virtually no F12 signal (Neth et al. (2001) *Thromb. Haemost.* 85:1043-1047, herein incorporated by reference in its entirety for all purposes). To investigate whether the discrepancy between these two studies could be due to the exon(s) chosen for detection, we designed qPCR probes against seven regions within F12 (exons 1-2, exons 3-4, exons 5-6, exon 7, exon 9, exon 11, and exon 14; FIG. 7A and Table 6). We found that while all probes detected F12 in human liver, only probes against exons 7, 9, 11, and 14 detected F12 in human brain (FIG. 7B).

with the most abundant F12 mRNA signal was the hippocampal pyramidal layer, with some signal in granule cells of the dentate gyms (data not shown). RNAscope signal outside of hematoxylin-stained cell nuclei suggests that the probe is not detecting pre-mRNA but rather mature mRNA. Due to difficulties in obtaining human brain tissue with consistently high RNA quality suitable for RNAscope analysis, we turned to mouse tissue to further study F12 expression in the brain.

To investigate the distribution of F12 mRNA in mouse brain, we performed RNAscope analysis on wild type mice ($FXII^{+/+}$), using F12 knockout mice ($FXII^{-/-}$) that do not produce factor XII protein as a control. As expected, both the exon 1-6 and exon 11-14 probes detected F12 in wild type mouse liver (data not shown). Similar to human brain, only the probe against exons 11-14 detected F12 mRNA in wild type mouse brain (data not shown), while no signal was detected in brain or liver from $FXII^{-/-}$ mice, confirming the probe's specificity for F12. The amount of signal from the

TABLE 6 qPCR Primers and Probes.

| Probe Target | Forward Primer | Reverse Primer | Probe Sequence |
|---|---|---|---|
| F12 Exons 1-2 | TGGACCAACGGACGGAT G (SEQ ID NO: 50) | CCCAAGGTGGAATCGAA AGTG (SEQ ID NO: 58) | CATGAGGGCTCTGCTGCTC CTGG (SEQ ID NO: 66) |
| F12 Exons 3-4 | TGCCACTTCCCCTTCCAG (SEQ ID NO: 51) | GTAGCACACCAGGGCTG AG (SEQ ID NO: 59) | ACCACCGGCAGCTGTACC ACAAAT (SEQ ID NO: 67) |
| F12 Exons 5-6 | ACTGTCTCTGTCCACAAC ACC (SEQ ID NO: 52) | CGGAGAAGCTGAGGCTC AAAG (SEQ ID NO: 60) | TCACTGGAAACCACTGCC AGAAAGAGA (SEQ ID NO: 68) |
| F12 Exon 7 | ACCAACCCGTGCCTCCAT (SEQ ID NO: 53) | GCAGAAGGCTCCGGTGT AG (SEQ ID NO: 61) | CTGCCTAGAGGTGGAGGG CCACC (SEQ ID NO: 69) |
| F12 Exon 9 | GTGGTGCTTCGTGCTGAA C (SEQ ID NO: 54) | GTTGGGGTCTGGCACTGT G (SEQ ID NO: 62) | CGACCGGCTGAGCTGGGA GTACT (SEQ ID NO: 70) |
| F12 Exon 11 | AGGATCTGACGGTGGTGC TC (SEQ ID NO: 55) | GTAGCTGACGGGCGAGA AG (SEQ ID NO: 63) | CCAGGAACGCCGTAACCA CAGCT (SEQ ID NO: 71) |
| F12 Exon 14 | ACACCGATGTGGCCTACT AC (SEQ ID NO: 56) | ACTGCGGAATCACCAAG GA (SEQ ID NO: 64) | CTGGATCCGGGAGCACAC CGTTT (SEQ ID NO: 72) |
| GAPDH | CCAGGTGGTCTCCTCTGA CT (SEQ ID NO: 57) | GCTTGACAAAGTGGTCGT TGA (SEQ ID NO: 65) | TCAACAGCGACACCCACT CCTC (SEQ ID NO: 73) |

Figure 7C:
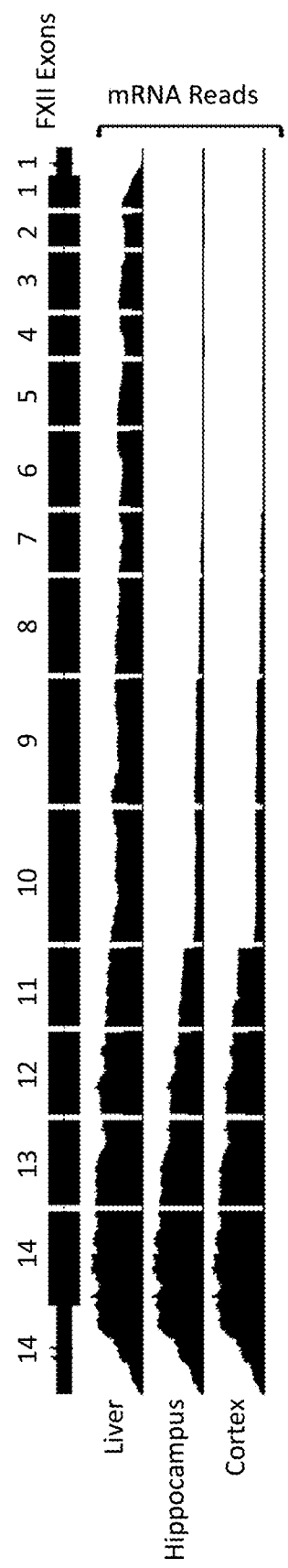
FIG. 7C shows RNAseq data from the GTEx Portal show full F12 mRNA coverage from exon 1 through exon 14 in human liver but only coverage from exon 7 through 14 in human hippocampus and cortex. F12 exons are ordered from right to left as the gene is located on the minus strand. Data were obtained from the GTEx Portal in December 2018.
Figure 10A:
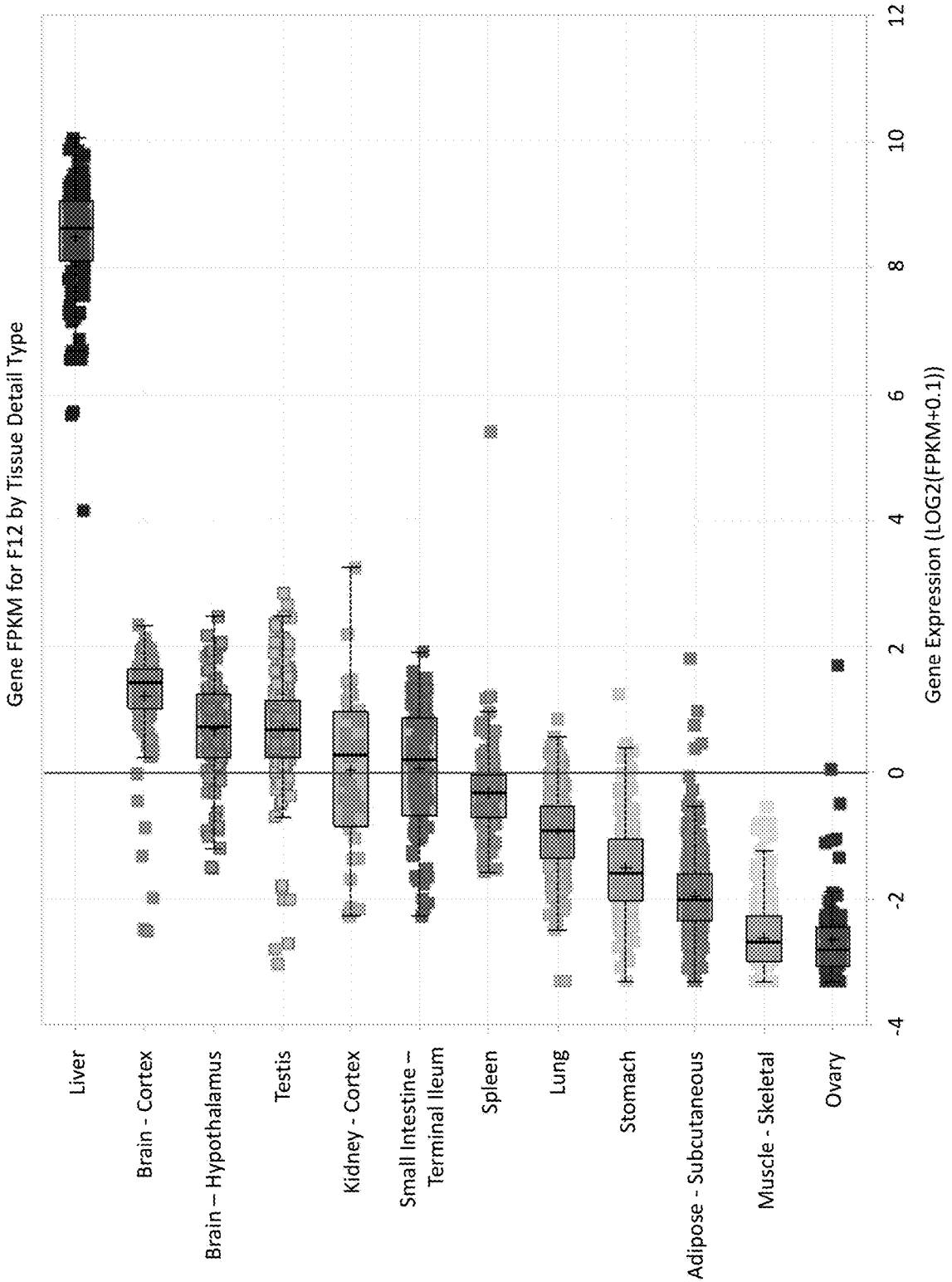
FIGS. 10A-10B show RNAseq data from human and mouse tissues.

Our results are supported by RNAseq data available through the Genotype-Tissue Expression (GTEx) Project (G.T. Consortium, The Genotype-Tissue Expression (GTEx) project, *Nat. Genet.*, 45 (2013) 580-585, herein incorporated by reference in its entirety for all purposes). The data show high F12 mRNA expression in the liver, with much lower expression in other tissues. Outside of the liver, some of the highest levels of F12 expression are found in brain regions (FIG. 10A). As expected, exon-by-exon analysis of F12 mRNA reads in human liver shows coverage for all 14 exons. However, F12 mRNA reads in human cortex and hippocampus only have coverage between exon 7 and exon 14 (FIG. 7C).

Figure 10B:
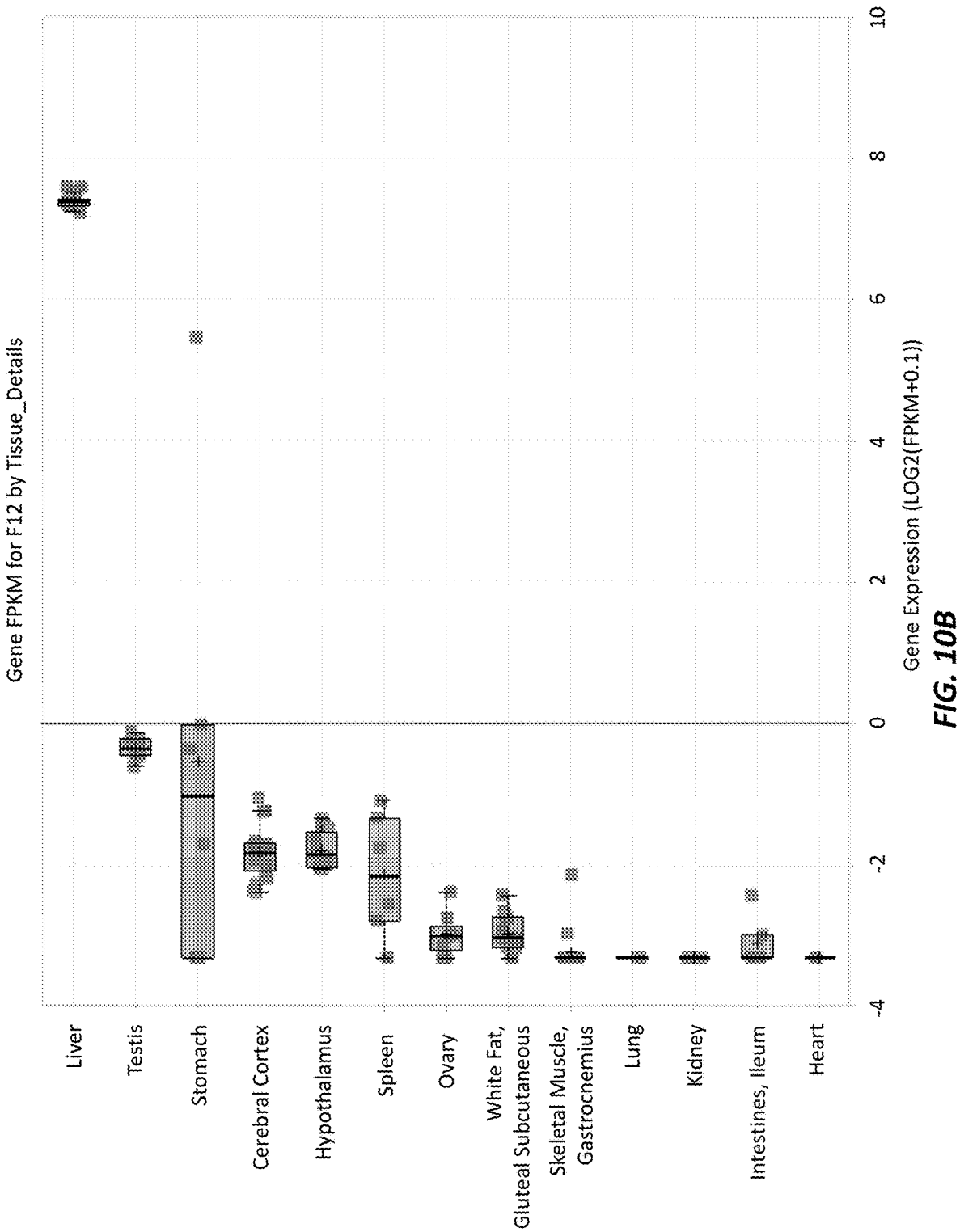

We next used RNA in situ hybridization to investigate the distribution of F12 mRNA in human hippocampus. For this purpose, two RNAscope probes against F12 were designed: one against exons 1-6, and one against exons 11-14. In agreement with our qPCR results and public GTEx data, F12 mRNA was only detected by the probe against exons 11-14 in the human hippocampus (data not shown). The region F12 exon 11-14 probe in mouse brain appeared less abundant than what was observed in human brain, prompting us to compare extra-hepatic F12 mRNA expression levels in mouse versus human tissues. Compared to the significant extra-hepatic expression of F12 in humans, where several tissues including brain had detectable F12 mRNA levels (FIG. 10A), expression of F12 in mice was not detected outside the liver (FIG. 10B). These data support the F12 mRNA levels detected by RNAscope in wild type mouse brain compared to human brain and suggest that the F12 mRNA levels found in mouse brain by RNAscope are not sufficient to be detected in bulk tissue by RNAseq.

To investigate whether differential expression of short F12 mRNA in human versus mouse brain is due to specific elements within the human F12 gene or to more general inter-species differences, we next analyzed F12 humanized mice ($FXII^{hum/hum}$), which only produce human factor XII. Full-length human F12 mRNA was detected by both probes in $FXII^{hum/hum}$ mouse liver (data not shown), while only the probe against human F12 exons 11-14 produced signal in the FXII$^{hum/hum}$ brain. Compared to wild type mice, FXII$^{hum/hum}$ mouse brain had much higher signal, suggesting that human F12 may have distinct regulatory features compared to mouse F12 that favor its expression in the brain. Similar to the pattern observed in human brain, expression of F12 in the brain of FXII$^{hum/hum}$ mice appeared to be mostly neuronal, with intense signal in the hippocampal pyramidal layer and cortical neurons (data not shown). Little to no signal was observed in the corpus callosum, which is mostly composed of glia, and in ependymal cells lining the lateral ventricle (data not shown).

To further investigate the potential neuronal expression of F12, we combined RNAscope technology with immunofluorescence using the probe against F12 exons 11-14 and the neuronal marker NeuN in consecutive sections of FXII$^{hum/hum}$ mouse brain. We observed an overlap in the distribution of NeuN immunofluorescence and F12 RNAscope signal in consecutive brain sections (data not shown), suggesting that F12 is mainly expressed in neurons. The strongest expression of F12 was detected in pyramidal neurons of the CA2/CA3 region of the hippocampus (data not shown).

Since the expression of F12 appears to be mainly neuronal, we next investigated whether F12 mRNA could be detected in primary neurons and neuronal cell lines by RNAseq. Indeed, F12 mRNA was expressed in iPS-derived human neurons (5.82 [1.65-7.38] FPKM) but was not detectable in mouse primary cortical neurons (data not shown). Similar to human brain tissue, exon-by-exon mRNA read analysis showed that human iPS neurons expressed a shorter isoform of F12 mRNA (data not shown). This intriguing difference in brain F12 mRNA expression between humans and mice prompted us to look at differences in the F12 gene between the species.

Our results raise the possibility that the human F12 genomic sequence may have different internal regulatory elements driving expression of the shorter isoform in neurons. Indeed, data available through the UCSC Browser (Kent et al. (2002) *Genome Res.* 12:996-1006, herein incorporated by reference in its entirety for all purposes) show that while multiple regulatory elements are located in the region spanning exons 7-10 in both the human and mouse F12 genes, a unique feature of human F12 is a large CpG island spanning exons 8-12. CpG islands are areas of the genome often associated with transcription start sites and are characterized by elevated G and C base composition and higher CpG dinucleotide frequency. In many cases, the presence of CpG islands at sites not associated with known transcripts led to the discovery of novel transcripts (Deaton et al. (2011) *Genes Dev.* 25:1010-1022, herein incorporated by reference in its entirety for all purposes). Thus, the presence of a large CpG island in the human but not mouse F12 sequence may underlie its increased transcription in human brain.

Figure 8B:
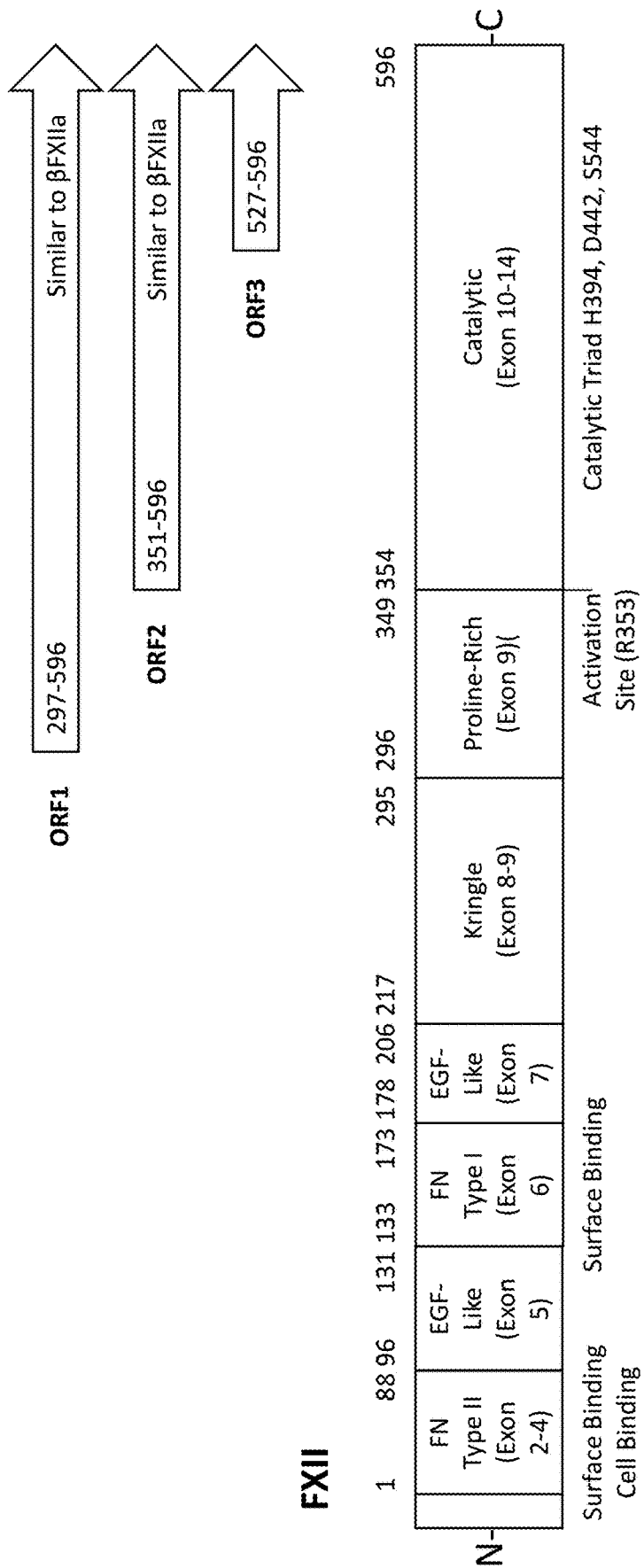
FIG. 8B shows F12 mRNA found in brain codes for three open reading frames (ORFs), with ORFs 1 and 2 coding for proteins similar to βFXIIa (N335-S596).

We next examined the F12 mRNA sequence detected in human brain for the presence of open reading frames (ORFs) to predict the putative protein(s) that would be translated. We found three ORFs, defined by the presence of start and stop codons in frame with full-length F12, in the human neuronal F12 sequence (FIG. 8B). Of these three ORFs, only ORFs 2 and 3 are conserved in mice, with poor amino acid sequence alignment in the ORF 1 region. Interestingly, GENBANK® (Benson et al. (2013) *Nucleic Acids Res.* 41:D36-42, herein incorporated by reference in its entirety for all purposes) lists five short human F12 mRNAs starting in exon 9, which correspond to ORF 1, while no human F12 mRNAs starting in exon 10 (corresponding to ORF 2), have been identified. No mouse F12 mRNAs starting at exon 9 or 10 have been described (FIG. 8A). The ATG found in human exon 9 is not conserved in mice. Taken together, these data support higher transcription of a short F12 isoform starting in exon 9 and coding for ORF 1 in humans, and identify differences in sequence and regulatory elements in human and mouse F12 genes that may help explain lower expression of short F12 mRNA in the mouse brain.

Here, we show that F12 mRNA is expressed in neurons in the human and FXII$^{hum/hum}$ mouse brain using qPCR, RNAscope, and RNAseq. Using RNAscope, we identified neurons as the primary cell type expressing short F12 mRNA in the brain and confirmed its expression in iPS-derived glutamatergic neurons by RNAseq. Intriguingly, we observed much higher levels of F12 mRNA in FXII$^{hum/hum}$ mouse and human brain compared to wild type mouse brain by RNAscope. This inter-species difference was further supported by RNAseq data showing negligible expression of F12 in mouse brain compared to human brain. Analysis of regulatory elements in human and mouse F12 genes suggested that the expression of a human F12 transcript starting in exon 9 may be due to a large CpG island spanning exons 8-12 found in human but not mouse F12.

To determine the possible functional role of the short brain FXII isoform, we evaluated the three predicted ORFs in the brain F12 transcript (FIG. 8B). Translation of ORF 1 would result in a protein containing the proline-rich and catalytic domains of FXII (M297-S596; SEQ ID NOS: 74 (protein) and 75 (DNA)). Translation of ORF 2 would result in a protein comprising the catalytic domain and three additional residues from the heavy chain (M351-5596; SEQ ID NOS: 76 (protein) and 77 (DNA)). ORF 3 would generate a protein that includes a portion of the catalytic domain that does not contain the catalytic triad (M527-5596; SEQ ID NOS: 78 (protein) and 79 (DNA)). Because the protein resulting from ORF 2 would have an unpaired cysteine (C467), likely leading to instability, and due to the lack of an intact catalytic domain in the protein resulting from ORF 3, we decided to focus on the protein that would be generated from ORF 1 (FXII$_{297-596}$). This choice was further supported by the presence of F12 transcripts in GENBANK® starting in ORF 1 but not ORFs 2 and 3 (FIG. 8A).

Figure 9A:
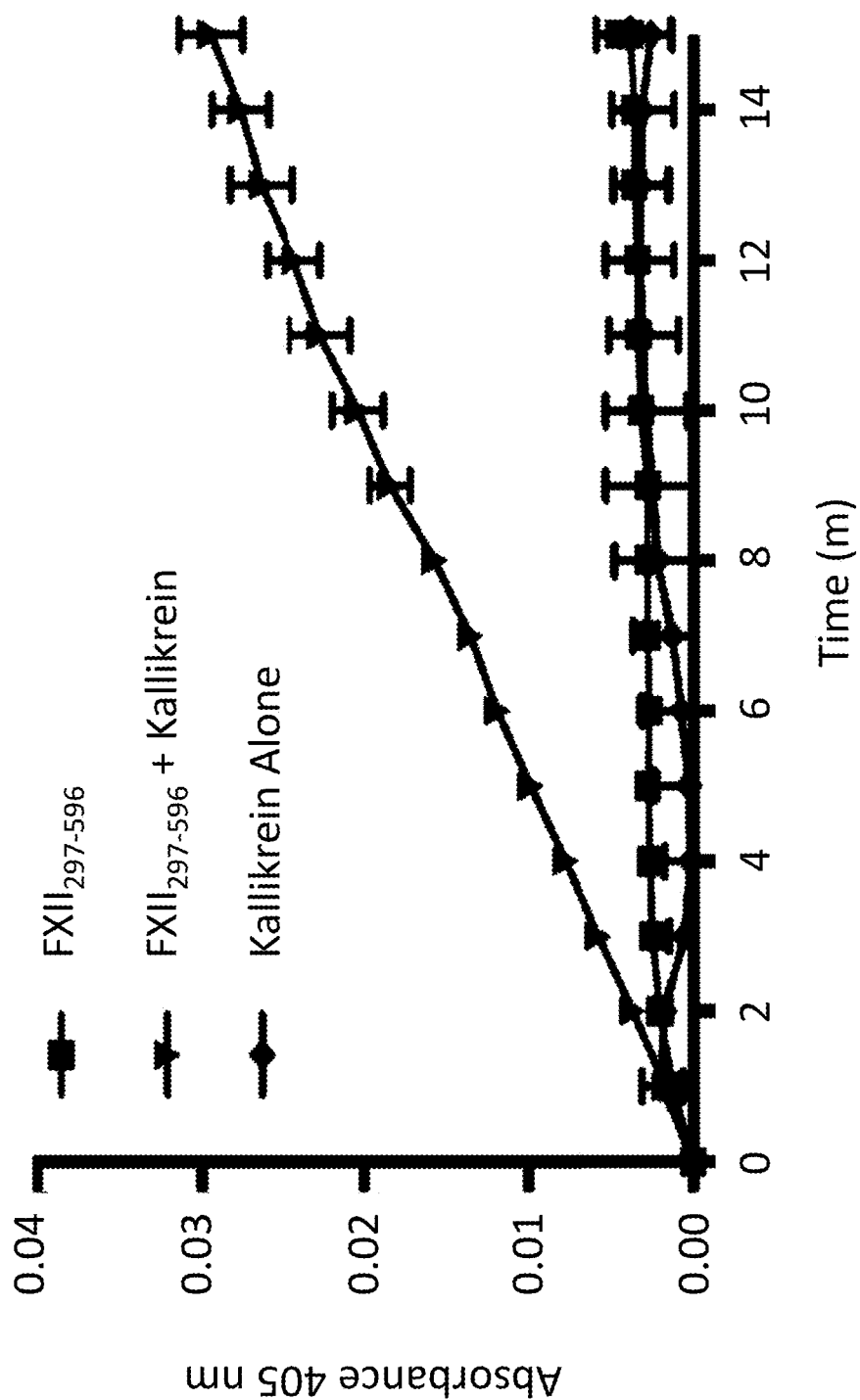
Figure 11:
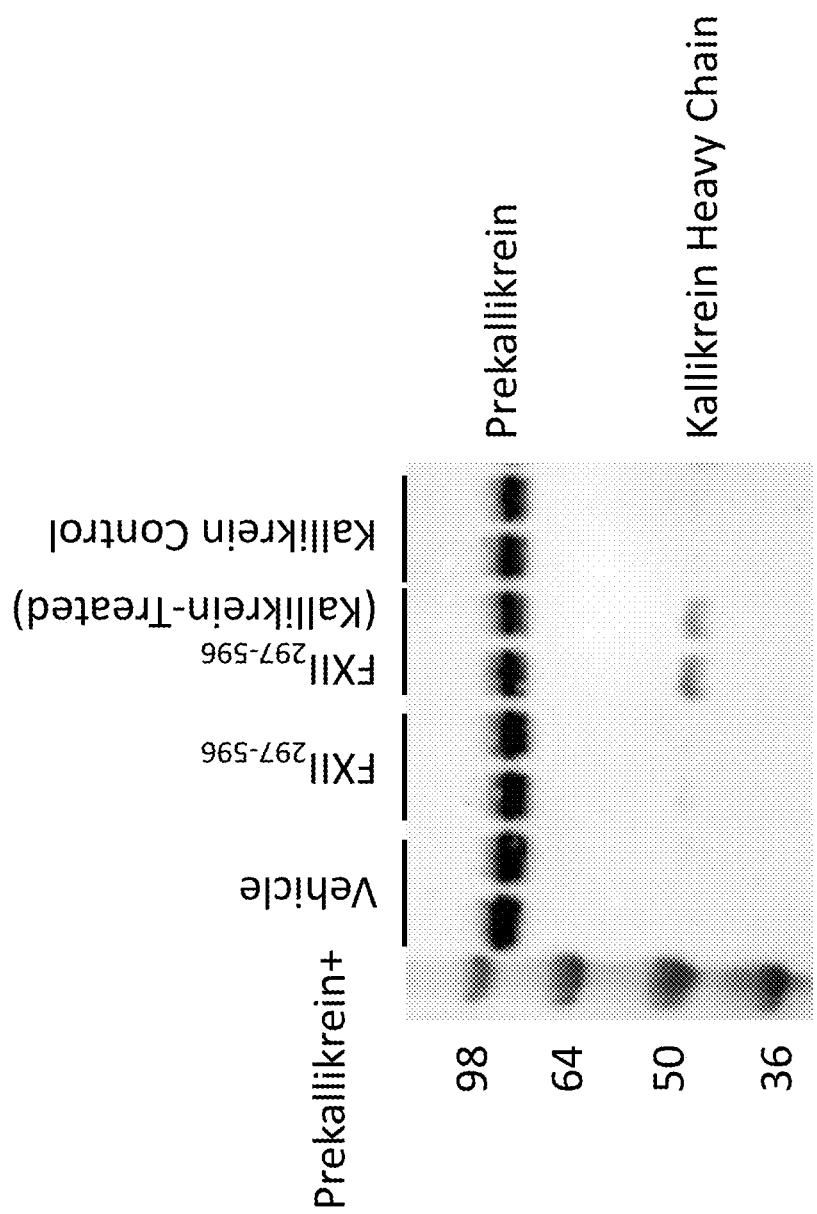
FIG. 11 shows $FXII_{297-596}$ (225 nM) was activated with kallikrein (15 nM), and kallikrein activity was inhibited with aprotinin prior to incubation with prekallikrein (200 nM). Prekallikrein was cleaved by kallikrein-activated $FXII_{297-596}$, but not by inactivated kallikrein alone. Kallikrein heavy chain was not observed in the kallikrein control lane due to the low levels of kallikrein used to activate $FXII_{297}$-596.

We evaluated whether the putative neuronal FXII isoform (FXII$_{297-596}$) could activate the pathways triggered by full length FXII. Cleavage at R353 by plasma kallikrein is required for activation of full-length FXII and results in separation of the heavy and light chains. We tested whether recombinant human FXII$_{297-596}$, which lacks a large portion of the heavy chain, requires cleavage by plasma kallikrein for enzymatic activity. As shown in FIG. 8B, no enzymatic activity was observed when FXII$_{297-596}$ was incubated with the FXIIa substrate S-2302 in the absence of kallikrein, while FXII$_{297-596}$ acquired enzymatic activity following pre-incubation with kallikrein (FIG. 9A). All reactions were treated with the kallikrein inhibitor aprotinin prior to addition of the chromogenic substrate to ensure that enzymatic activity was not a result of kallikrein-mediated cleavage of the substrate. These results suggested that, similar to full-length FXII, the putative brain FXII isoform is activated following cleavage by kallikrein. We next examined whether activated FXII$_{297-596}$ can reciprocally activate prekallikrein to kallikrein. While no cleavage of prekallikrein was observed with non-activated FXII$_{297-596}$, activated FXII$_{297-596}$ converted prekallikrein to kallikrein as seen through the generation of kallikrein heavy chain (FIG. 11). Thus, FXII$_{297-596}$ is capable of launching the kallikrein-kinin pathway, suggesting that FXII$_{297-596}$ activation can lead to the generation of bradykinin.

It was recently shown that cleavage of FXII within its proline-rich domain, which releases a portion of the heavy chain, increases the susceptibility of FXII to activation by kallikrein at R353. See, e.g., de Maat et al. (2019) *J. Thromb. Haemost.* 17:183-194, herein incorporated by reference in its entirety for all purposes. We hypothesized that FXII$_{297-596}$, in which the heavy chain N-terminal to the proline rich domain is missing, would essentially be pre-cleaved, and could therefore be susceptible to activation by levels of kallikrein that would not activate full-length FXII. Because the recombinant FXII$_{297-596}$ used in this study was produced in *E. coli* and lacked glycosylation, we were unable to directly compare its susceptibility to activation to that of full-length FXII purified from human plasma. We therefore sought to enzymatically generate a protein similar to FXII$_{297-596}$ from full-length FXII. Analysis of putative cleavage sites in the FXII amino acid sequence using Prosper software (Song et al. (2012) *PLoS One* 7:e50300, herein incorporated by reference in its entirety for all purposes) revealed a cathepsin K cleavage site between L296 and M297, which would generate a truncated FXII protein identical to the isoform potentially expressed in the brain (FXII$_{297-596}$).

Figure 9B:
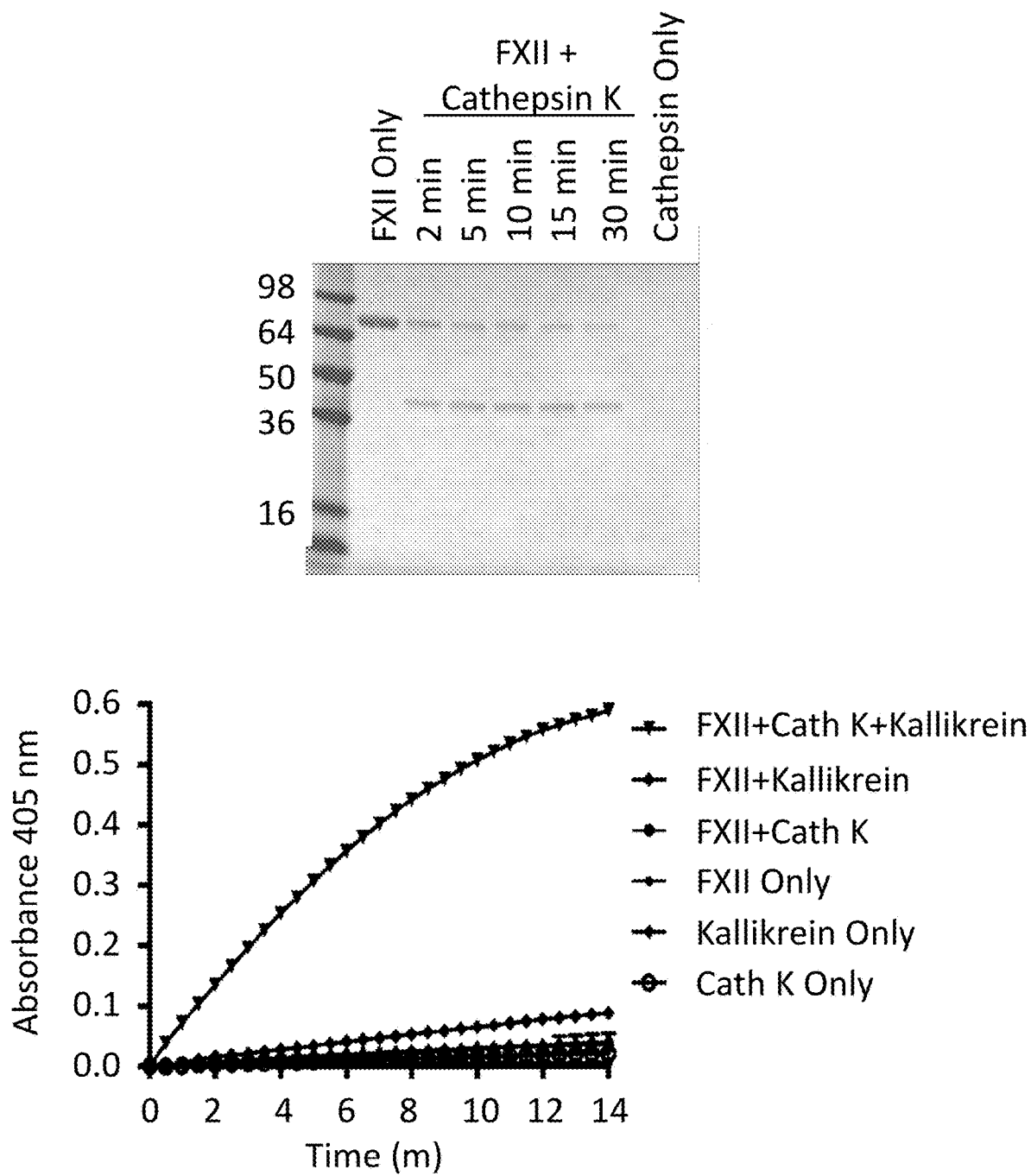

As shown in FIG. 9B, incubation of full-length FXII with cathepsin K generated stable FXII fragments with sizes supporting cleavage between L296 and M297, which would yield two fragments of ~35 kDa that would be expected to run at ~40 kDa due to glycosylation. We next compared enzymatic activity of full-length FXII and the truncated FXII generated by cathepsin K cleavage. As expected, full-length FXII and cathepsin K-cleaved FXII had negligible activity on their own, but cathepsin K-cleaved FXII had dramatically increased activity compared to full-length FXII when incubated with plasma kallikrein (FIG. 9B). Our results agree with a recent study showing cathepsin K acting synergistically with kallikrein to activate FXII (de Maat et al. (2019) *J. Thromb. Haemost.* 17:183-194, herein incorporated by reference in its entirety for all purposes) and suggest that the putative brain FXII$_{297}$-596 isoform, which is similar to cathepsin-K cleaved FXII, might have increased susceptibility to activation by plasma kallikrein and possibly other proteases.

In addition to activating prekallikrein and the intrinsic coagulation pathway, FXIIa has been shown to convert pro-HGF to active HGF. See, e.g., Shimomura et al. (1995) *Eur. J. Biochem.* 229:257-261 and Peek et al. (2002) *J. Biol. Chem.* 277:47804-47809, each of which is herein incorporated by reference in its entirety for all purposes. We confirmed the ability of hepatocyte growth factor activator (HGFA) and βFXIIa to cleave pro-HGF (FIG. 9C). Furthermore, we found that kallikrein-activated FXII$_{297-596}$ cleaved pro-HGF to the active two-chain form (FIG. 9D), suggesting that brain FXII could contribute to local HGF activation. This ability to activate pro-HGF is specific, since other serine proteases found in the brain such as thrombin and tissue plasminogen activator did not convert pro-HGF to HGF (FIGS. 9C and 9D).

Accumulating evidence suggests that expression of coagulation and contact system proteins occurs outside the liver, especially under pathological conditions. See, e.g., Ashby et al. (2012) *Neurobiol. Aging* 33:1345-1355, Yin et al. (2010) *Am. J. Pathol.* 176:1600-1606, and Takano et al. (2003) *Brain Res.* 978:72-82, each of which is herein incorporated by reference in its entirety for all purposes. A role for extra-hepatic FXII expression is also emerging: recent studies have shown that FXII is expressed in lung fibroblasts (Jablonska et al. (2010) *J. Biol. Chem.* 285: 11638-11651, herein incorporated by reference in its entirety for all purposes) and that neutrophil-expressed FXII contributes to neutrophil activation and migration to sites of inflammation (Stavrou et al. (2018) *J. Clin. Invest.* 128:944-959, herein incorporated by reference in its entirety for all purposes). Here, we show for the first time that F12 mRNA is expressed in neurons in the human and FXII$^{hum/hum}$ mouse brain using qPCR, RNAscope, and RNAseq. Previous studies have produced conflicting results regarding F12 expression in human brain. Using primers spanning exons 7 to 9, one group detected F12 mRNA (Yasuhara et al. (1994) *Brain Res.* 654:234-240, herein incorporated by reference in its entirety for all purposes), while qPCR performed using primers and a probe within exons 3-5 showed virtually no F12 signal (Neth et al. (2001) *Thromb. Haemost.* 85:1043-1047, herein incorporated by reference in its entirety for all purposes). These studies used different methods and are therefore not directly comparable; however, Yasuhara et al. concluded that F12 mRNA is found in the brain, whereas Neth et al. concluded that F12 mRNA is exclusively found in the liver. Our results help resolve this discrepancy, since we found that F12 mRNA corresponding to exons 7-14 but not exons 1-6 is found in the brain (FIG. 7C), thereby supporting both reports.

Using RNAscope, we identified neurons as the primary cell type expressing short F12 mRNA in the brain and confirmed its expression in iPS-derived glutamatergic neurons by RNAseq. Intriguingly, we observed much higher levels of F12 mRNA in FXII$^{hum/hum}$ mouse and human brain compared to WT mouse brain by RNAscope. This interspecies difference was further supported by RNAseq data showing negligible expression of F12 in mouse brain compared to human brain. Analysis of regulatory elements in human and mouse F12 genes suggested that the expression of a human F12 transcript starting in exon 9 may be due to a large CpG island spanning exons 8-12 found in human but not mouse F12. The functional significance of this divergence between human and mouse neurons is unknown.

Recent work has suggested functional implications for a potential brain FXII protein spanning FXII$_{297-596}$. FXII activation can be achieved by sub-threshold levels of plasma kallikrein when FXII is first processed by other enzymes like elastase or cathepsin K. See, e.g., de Maat et al. (2019) *J. Thromb. Haemost.* 17:183-194, herein incorporated by reference in its entirety for all purposes. Cleavage of the FXII heavy chain is thought to uncover the FXII activation cleavage site (R353-V354), allowing for its more efficient activation in solution. See, e.g., de Maat et al. (2019) *J. Thromb. Haemost.* 17:183-194, herein incorporated by reference in its entirety for all purposes. Based on in silico analysis, the putative neuronal FXII$_{297-596}$ can be generated by cleavage of full-length FXII with cathepsin K. While the exact cathepsin K cleavage site on FXII remains to be shown, our results with cathepsin K-cleaved FXII suggest that the putative neuronal FXII isoform might be activated by low levels of kallikrein. In this regard, plasma prekallikrein mRNA and protein have been found in various brain regions (Ashby et al. (2012) *Neurobiol. Aging* 33:1345-1355 and Neth et al. (2001) *Thromb. Haemost.* 85:1043-1047, each of which is herein incorporated by reference in its entirety for all purposes), and at levels comparable (Cerf and Raidoo (2000) *Metab. Brain Dis.* 15:315-323, herein incorporated by reference in its entirety for all purposes) to what we used in this study. Furthermore, plasma prekallikrein expression was localized to hippocampal neurons (Cerf and Raidoo (2000) *Metab. Brain Dis.* 15:315-323, herein incorporated by reference in its entirety for all purposes), the cells in which we found highest levels of short F12 mRNA, suggesting that activation of neuronal FXII may occur in vivo. In addition, our results raise the possibility that the neuronal FXII isoform might have increased susceptibility to activation by other proteases, perhaps produced by neurons or other brain cells, which would not activate full-length FXII.

Activation of pro-HGF to HGF is necessary for its signaling through the Met receptor. While a role for HGF-Met signaling in neurons has been established (Kato (2017) *Biomed. Rep.* 7:495-503 and Tyndall and Walikonis (2006) *Cell Cycle* 5:1560-1568, each of which is herein incorporated by reference in its entirety for all purposes), how pro-HGF is activated in the brain has not been well-characterized. HGFA is the main HGF activator in the circulation. See, e.g., Itoh et al. (2004) *Gastroenterology* 127:1423-1435, herein incorporated by reference in its entirety for all purposes. Since HGFA knockout mice have no developmental abnormalities (Itoh et al. (2004) *Gastroenterology* 127:1423-1435, herein incorporated by reference in its entirety for all purposes) while HGF knockout mice are embryonic lethal (Uehara et al. (1995) *Nature* 373:702-705, herein incorporated by reference in its entirety for all purposes), other HGF activators likely participate in HGF activation in tissues. Interestingly, FXII is a homolog of HGFA (Ponczek et al. (2008) *J. Thromb. Haemost.* 6:1876-1883, herein incorporated by reference in its entirety for all purposes) and has been shown to convert pro-HGF to active HGF in vitro. See, e.g., Shimomura et al. (1995) *Eur. J Biochem.* 229:257-261 and Peek et al. (2002) *J. Biol. Chem.* 277:47804-47809, each of which is herein incorporated by reference in its entirety for all purposes. We hypothesize that the putative neuronal FXII may participate in the conversion of pro-HGF to active HGF in the brain, contributing to neuronal HGF-Met signaling.

Neuronal Met signaling has been implicated in a variety of physiological processes, including neurite outgrowth, dendritic arborization, long-term potentiation, and memory. See, e.g., Kato (2017) *Biomed. Rep.* 7:495-503, Wright and Harding (2015) *J. Alzheimers Dis.* 45:985-1000, and Tyndall and Walikonis (2006) *Cell Cycle* 5:1560-1568, each of which is herein incorporated by reference in its entirety for all purposes. We observed enriched expression of F12 mRNA in hippocampal and neocortical pyramidal neurons, raising the possibility that activation of HGF by putative neuronal FXII could occur in these cells. Interestingly, deletion of Met in neurons arising from the dorsal pallium (which include hippocampal and neocortical neurons) results in deficits in spontaneous alternation and in hypoactivity (Thompson and Levitt (2015) *J. Neurodev. Disord.* 7:35, herein incorporated by reference in its entirety for all purposes), supporting the importance of HGF-Met signaling in cells found to express F12 mRNA. Further investigation into the function of the short FXII isoform may shed light on its role in these cell populations.

In addition to the insights on the role of neuronal HGF-Met signaling derived from in vitro and animal studies, accumulating evidence suggests that dysregulation in HGF-Met signaling contributes to neurodevelopmental disorders and neurodegeneration in humans. See, e.g., Eagleson et al. (2017) *Biol. Psychiatry* 81:424-433, Peng et al. (2013) *Int. Rev. Neurobiol.* 113:135-165, and Wright and Harding (2015) *J. Alzheimers Dis.* 45:985-1000, each of which is herein incorporated by reference in its entirety for all purposes. In particular, expression of Met protein is decreased in the hippocampal neurons of AD patients (Hamasaki et al. (2014) *Neuropathology* 34:284-290, herein incorporated by reference in its entirety for all purposes), while HGF protein levels are increased in AD brain (Fenton et al. (1998) *Brain Res.* 779:262-270, herein incorporated by reference in its entirety for all purposes). Whether neuronal FXII levels are altered in AD or other disease states and whether neuronal FXII plays a role in disease processes are open questions. Future studies will shed light on the details of neuronal FXII expression and on the role of the neuronal FXII isoform in physiological and pathological activation of HGF and contact pathways in the brain.

Materials and Methods qPCR. Total RNA from human liver, human whole brain, hippocampus, temporal lobe, and cortex were from Clontech (Takara Bio USA; Mountain View, Calif.). mRNA was reverse-transcribed into cDNA using SuperScript® VILO™ Master Mix (Invitrogen by Life Technologies; Waltham, Mass.). cDNA was diluted to 0.5-5 ng/µL, and 2.5-25 ng cDNA input was amplified with the SensiFAST Hi-ROX MasterMix (Bioline; Taunton, Mass.) using the ABI 7900HT Sequence Detection System (Applied Biosystems; Foster City, Calif.). Primers and probes against human F12 and GAPDH used are shown in Table 5. Data are presented as % of target gene expression seen in control tissue ($2^{-(\Delta\Delta Ct)}$*100).

Human Brain Tissue. For RNAscope analysis, two sources of human brain tissue were used. Fresh-frozen hippocampal brain tissue from the Harvard Brain Tissue Resource Center (Belmont, Mass.) was sliced at 10 µm, mounted onto VWR superfrost slides, and stored at −80° C. Pre-mounted 5 µm formalin fixed, paraffin-embedded human hippocampus sections were from Abcam (Cambridge, Mass.).

Plasma Collection. For plasma collection, blood was drawn from the vena cava using sodium citrate primed needles. Blood was spun at 1500×g at room temperature for 10 minutes, and platelet-poor plasma was collected and stored at −80° C. For tissue collection, mice were transcardially perfused with 0.9% saline. Brains and livers were removed, frozen on dry ice in Optimal Cutting Temperature compound, and stored at −80° C. Ten µm sections were mounted onto Superfrost plus slides (VWR; Radnor, Pa.) and stored at −80° C.

In Situ RNA Hybridization. In situ RNA hybridization was performed using the RNAscope 2.5 HD system RED (Advanced Cell Diagnostics; Newark, Calif.) following the manufacturer's protocol for fresh-frozen or formalin-fixed, paraffin-embedded tissue. The probes (ACDbio Catalog Nos. 313901 (PPIB (human)), 313911 (PPIB (mouse)), 310043 (DAPB), 493191 (F12 exon 1-6 (human)), 473781 (F12 exon 11-14 (human)), 493201 (F12 exon 1-6 (mouse)), and 483971 (F12 exon 11-14 (mouse))) were used in a single-plex manual RNAscope assay, and colorimetric signal from the RNAscope probes was captured with a 40× objective using an Aperio slide scanner (Leica Microsystems; Buffalo Grove, Ill.). To confirm that tissue was suitable for RNA analysis, a probe against a ubiquitously expressed gene (cyclophilin B; PPIB) was used as a positive control, and a probe against the bacterial gene (4-hydroxy-tetrahydrodipicolinate reductase; DapB) was used as a negative control. Due to the high specificity of RNAscope probes, separate RNAscope probes specific for mouse and human F12 were designed.

Immunofluorescence/RNAscope. Immunofluorescence and RNAscope were performed on consecutive sections of FXII$^{hum/hum}$ mouse brain. RNAscope was run as described above using the probe against F12 exons 11-14, except the tissue was counterstained with DAPI and images were acquired using a 20× objective with Ex/Em of 590/617 for RNAscope RED and 358/461 for DAPI on a Zeiss AxioScan Z.1 slide scanner (Carl Zeiss Microscopy; Thornwood, N.Y.). RNAscope signal was pseudocolored white using Halo software (Indica Labs; Corrales, N.Mex.). For immunofluorescence, tissue was post-fixed with 4% paraformaldehyde (Electron Microscopy Sciences; Hatfield, Pa.) in phosphate buffer and blocked with 3% donkey serum (Jackson Laboratory; Bar Harbor, Me.) containing 0.25% Triton-X (Sigma Aldrich; St. Louis, Mo.) in PBS. Slides were then incubated with NeuN antibody (Abcam; Cat #Ab177487) diluted 1:500 in blocking buffer overnight at 4° C., then with Alexa-488 conjugated secondary antibody (ThermoFisher) and DAPI (ThermoFisher) diluted in 3% donkey serum for 1 hour at room temperature. After washing in PBS, slides were coverslipped using Aqua-Mount mounting medium (ThermoFisher). Images were acquired using a 20× objective with Ex/Em of 490/525 for Alexa-488 and 358/461 for DAPI on an AxioScan Z.1 slide scanner.

FXIIa Activity Assay. To measure FXII$_{297}$-596 activation by plasma kallikrein, recombinant human FXII$_{297-596}$ (Proteintech; Rosemont, Ill.) was incubated with 15 nM plasma kallikrein (Molecular Innovations; Novi, Mich.) for 18 hrs at 37° C. in 20 mM HEPES containing 140 mM NaCl, pH 7.4 (HEPES-buffered saline; HBS). Kallikrein activity was then inhibited using 100 KIU/mL aprotinin (Sigma-Aldrich; St. Louis, Mo.), and FXIIa activity was measured using the chromogenic substrate S-2302 (H-D-Pro-Phe-Arg-pNA·2HCl; Diapharma; West Chester, Ohio) at a concentration 0.8 mM. Assays were performed at 37° C. in flat-bottom 96-well polystyrene MaxiSorp plates (Thermo Fisher). Enzyme activity was detected as change in absorbance at 405 nm using a Spectramax i3X microplate reader (Molecular Devices; Downingtown, Pa.).

Cathepsin K-cleaved FXII was generated by incubation of FXII (1.25 uM; Molecular Innovations) with Cathepsin K (100 nM; Enzo Life Sciences) in HBS. Reactions were stopped by adding non-reducing sample buffer and heating at 100° C. for 5 min. FXII fragments were separated by SDS-PAGE and visualized by Coommassie Blue staining. Proteolytic activity of cathepsin K-cleaved FXII was analyzed by incubating FXII (375 nM) with cathepsin K (30 nM) or vehicle with plasma kallikrein (15 nM) for 15 min. Kallikrein activity was then inhibited with aprotinin, and FXIIa activity measured with the S-2302 chromogenic substrate.

To analyze plasma prekallikrein cleavage, FXII$_{297-596}$ (300 nM) was first incubated with plasma kallikrein (15 nM) or vehicle at 37° C. for 18 hrs. Kallikrein activity was then inactivated using aprotinin (100 KIU/mL; Sigma). Prekallikrein purified from human plasma (200 nM; Molecular Innovations) was incubated with kallikrein- or vehicle-activated FXII$_{297-596}$ (225 nM) or FXII (225 nM) at 37° C. for 2 hrs in HBS. Reactions were stopped by adding reducing sample buffer. SDS-PAGE was performed as described above and blots were analyzed with an antibody against human prekallikrein (Abcam; Cat #ab1006).

Western Blot. Plasma from FXII$^{-/-}$, FXII$^{+/+}$, and FXII$^{hum/hum}$ mice was analyzed under reducing conditions by western blot. SDS-PAGE was performed using 4-20% Tris-Glycine gels (Invitrogen), the gels transferred onto 0.2 μm PVDF membranes (BioRad; Hercules, Calif.), and analyzed with antibodies against mouse factor XII (CloudClone Corp; Katy, Tex.; Cat #PAA677Mu01), human factor XII (Abcam; Cat #Ab196670), and albumin (Thermo Scientific Pierce; Waltham, Mass.; Cat #PA1-29335).

To analyze HGF activation, FXII$_{297}$-596 (300 nM) was first incubated with plasma kallikrein (15 nM) or vehicle at 37° C. for 18 hrs. Kallikrein activity was then inactivated using aprotinin (100 KIU/mL; Sigma). Recombinant human pro-HGF (25 μg/mL; R&D Systems; Minneapolis, Minn.) was incubated with kallikrein- or vehicle-activated FXII$_{297}$-596 (225 nM), recombinant human hepatocyte growth factor activator (225 nM; Sino Biological; Wayne, Pa.), two-chain tissue plasminogen activator (225 nM; Oxford Biomedical Research; Rochester Hills, Mich.), or βFXIIa (50 nM; Molecular Innovations) at 37° C. for 5 hrs in HBS. Reactions were stopped by adding reducing sample buffer. SDS-PAGE was performed as described above and blots were analyzed with an antibody against human HGF (R&D Systems; Cat #AF-294-SP).

Cell Culture. Human iPS glutamatergic neurons (iCell® Glutaneurons; Cellular Dynamics; Madison, Wis.) were cultured according to the manufacturer's instructions and differentiation was validated by RNAseq. Cells showed high expression of two well-known neuronal markers, Microtubule Associated Protein 2 (MAP2) and vesicular glutamate transporter VGLUT2 (SCL17A6) and low expression of GFAP (astrocyte marker) and NES (marker of neural stem cells and proliferating endothelial cells) (data not shown). SH-SY5Y human neuroblastoma cells and Neuro-2a mouse neuroblastoma cells from American Type Tissue Collection (ATCC; Manassas, Va.) were cultured in EMEM (Irvine Scientific; Santa Ana, Calif.) containing L-glutamate, penicillin, streptomycin, and 10% fetal bovine serum (ThermoFisher). Primary cortical neurons from C57BL/6 mice (Lonza) were cultured according to the manufacturer's instructions.

RNAseq. The protocols for RNA extraction and sequencing library preparation were similar to those described previously (Atanasio et al. (2016) Sci. Rep. 6:23204, herein incorporated by reference in its entirety for all purposes). Strand-specific RNA-seq libraries were prepared from 500 ng RNA using KAPA stranded mRNA-Seq Kit (KAPA Biosystems). The libraries were amplified by twelve-cycle PCR. Sequencing was performed on Illumina HiSeq®2000 (Illumina) by multiplexed single-read run (for iPS human neurons, mouse primary neurons, and mouse tissue), or paired-read run (for SH-SY5Y and Neuro-2A cell lines). The resulting FASTQ files were analyzed via FastQC to ensure sufficient data quality. The reads were mapped to human genome (hg19) or mouse genome (mm10) using commercial software ArrayStudio (OmicSoft) with two mismatches allowed. In our samples, 83%-90% reads were uniquely mapped. Gene expressions were derived from raw sequencing reads using OmicSoft ArrayStudio RNASeq analysis pipeline (Qiagen Inc.). For each gene, reads uniquely mapped to the exons of the gene were identified and counted. The resulting read counts were summarized at gene level as the raw expression.

We claim:

1. A non-human animal comprising in its genome a humanized endogenous F12 locus in which a segment of the endogenous F12 locus from the start codon to the stop codon comprising both coding sequence and non-coding sequence has been deleted and replaced with a corresponding human F12 sequence from the start codon to the stop codon comprising both coding sequence and non-coding sequence, and
wherein the non-human animal expresses a short human coagulation factor XII isoform in the brain.

2. The non-human animal of claim 1, wherein the humanized endogenous F12 locus comprises an endogenous F12 promoter, wherein the human F12 sequence is operably linked to the endogenous F12 promoter.

3. The non-human animal of claim 1, wherein the humanized endogenous F12 locus comprises an endogenous F12 3' untranslated region that has not been deleted and replaced with the corresponding human F12 sequence.

4. The non-human animal of claim 1, wherein the humanized endogenous F12 locus comprises an endogenous F12 5' untranslated region that has not been deleted and replaced with the corresponding human F12 sequence.

5. The non-human animal of claim 1, wherein:
(i) the human F12 sequence at the humanized endogenous F12 locus comprises a sequence at least 90%, 95%, 96%, 97%, 98%, 99%, or 100% identical to the sequence set forth in SEQ ID NO: 31 or 32; and/or
(ii) the humanized endogenous F12 locus encodes a protein comprising a sequence at least 90%, 95%, 96%, 97%, 98%, 99%, or 100% identical to the sequence set forth in SEQ ID NO: 5 or 46; and/or
(iii) the humanized endogenous F12 locus comprises a coding sequence comprising a sequence at least 90%, 95%, 96%, 97%, 98%, 99%, or 100% identical to the sequence set forth in SEQ ID NO: 13 or 48; and/or
(iv) the humanized endogenous F12 locus comprises a sequence at least 90%, 95%, 96%, 97%, 98%, 99%, or 100% identical to the sequence set forth in SEQ ID NO: 17 or 18.

6. The non-human animal of claim 1, wherein the humanized endogenous F12 locus comprises a selection cassette or a reporter gene within an intron of the corresponding human F12 sequence, or wherein the humanized endogenous F12 locus does not comprise a selection cassette or a reporter gene.

7. The non-human animal of claim 1, wherein the non-human animal is homozygous for the humanized endogenous F12 locus.

8. The non-human animal of claim 1, wherein the non-human animal comprises the humanized endogenous F12 locus in its germline.

9. The non-human animal of claim 1, wherein the non-human animal is a mammal.

10. The non-human animal of claim 9, wherein the non-human animal is a rat or mouse.

11. The non-human animal of claim 10, wherein the non-human animal is the mouse.

12. The non-human animal of claim 1, wherein:
   (i) the short human coagulation factor XII isoform is encoded by an F12 mRNA detected by probes against exons 11-14 of human F12 but not by probes against exons 1-6 of human F12; and/or
   (ii) the short human coagulation factor XII isoform is $FXII_{297-596}$; and/or
   (iii) the short human coagulation factor XII isoform is expressed in neurons in the brain; and/or
   (iv) the short human coagulation factor XII isoform can be activated by plasma kallikrein and converts pro-HGF to active HGF.

13. The non-human animal of claim 1, wherein the non-human animal has an activated partial thromboplastin time (aPTT) that is not significantly different from an aPTT in a corresponding wild type non-human animal and/or wherein the non-human animal has a prothrombin time (PT) that is not significantly different from an PT in a corresponding wild type non-human animal.

14. The non-human animal of claim 1, wherein the non-human has human coagulation factor XII plasma levels of at least about 5 μg/mL.

15. A method of assessing the activity of a human-coagulation-factor-XII-targeting reagent in vivo, comprising:
   (a) administering the human-coagulation-factor-XII-targeting reagent to the non-human animal of claim 1; and
   (b) assessing the activity of the human-coagulation-factor-XII-targeting reagent in the non-human animal.

16. A method of optimizing the activity of a human-coagulation-factor-XII-targeting reagent in vivo, comprising:
   (I) performing the method of claim 15 a first time in a first non-human animal comprising in its genome a humanized endogenous F12 locus;
   (II) changing a variable and performing the method of step (I) a second time with the changed variable in a second non-human animal comprising in its genome a humanized endogenous F12 locus; and
   (III) comparing the activity of the human-coagulation-factor-XII-targeting reagent in step (I) with the activity of the human-coagulation-factor-XII-targeting reagent in step (II), and selecting the method resulting in the higher activity.

17. A method of making the non-human animal of claim 1, comprising:
   (I) (a) modifying the genome of a pluripotent non-human animal cell to comprise in its genome a humanized endogenous F12 locus in which a segment of the endogenous F12 locus has been deleted and replaced with a corresponding human F12 sequence, wherein a region of the endogenous F12 locus comprising both coding sequence and non-coding sequence has been deleted and replaced with a corresponding human F12 sequence comprising both coding sequence and non-coding sequence, and wherein the region of the endogenous F12 locus from the start codon to the stop codon has been deleted and replaced with the corresponding human F12 sequence;
   (b) identifying or selecting the genetically modified pluripotent non-human animal cell comprising in its genome the humanized endogenous F12 locus;
   (c) introducing the genetically modified pluripotent non-human animal cell into a non-human animal host embryo; and
   (d) gestating the non-human animal host embryo in a surrogate mother, wherein the surrogate mother produces an F0 progeny genetically modified non-human animal comprising in its genome the humanized endogenous F12 locus, wherein the F0 progeny genetically modified non-human animal expresses the short human coagulation factor XII isoform in the brain; or
   (II) (a) modifying the genome of a non-human animal one-cell stage embryo to comprise in its genome the humanized endogenous F12 locus, wherein a region of the endogenous F12 locus comprising both coding sequence and non-coding sequence has been deleted and replaced with a corresponding human F12 sequence comprising both coding sequence and non-coding sequence, and wherein the region of the endogenous F12 locus from the start codon to the stop codon has been deleted and replaced with the corresponding human F12 sequence;
   (b) selecting the genetically modified non-human animal one-cell stage embryo comprising in its genome the humanized endogenous F12 locus; and
   (c) gestating the genetically modified non-human animal one-cell stage embryo in a surrogate mother, wherein the surrogate mother produces an F0 progeny genetically modified non-human animal comprising in its genome the humanized endogenous F12 locus, wherein the F0 progeny genetically modified non-human animal expresses the short human coagulation factor XII isoform in the brain.

* * * * *